US012735699B2

(12) United States Patent
Kalmeijer et al.

(10) Patent No.: US 12,735,699 B2
(45) Date of Patent: Sep. 15, 2026

(54) COMPOSITIONS AND METHODS FOR TREATMENT OF HEPATITIS D VIRUS INFECTION

(71) Applicant: GlaxoSmithKline Intellectual Property (No.3) Limited, Stevenage (GB)

(72) Inventors: Ronald Cornelis Marie Kalmeijer, Titusville, NJ (US); Michael Biermer, Berlin (DE); Oliver Lenz, Sint-Katelijne-Waver (BE); Maria Gloria Beumont, Titusville, NJ (US); Heather Lynn Davis, Schilde (BE); Thomas Naoki Kakuda, San Francisco, CA (US)

(73) Assignee: GlaxoSmithKline Intellectual Property (No.3) Limited, Stevenage (GB)

( * ) Notice: Subject to any disclaimer, the term of this patent is extended or adjusted under 35 U.S.C. 154(b) by 1480 days.

(21) Appl. No.: 17/304,479

(22) Filed: Jun. 22, 2021

(65) Prior Publication Data

US 2021/0403908 A1 Dec. 30, 2021

Related U.S. Application Data

(60) Provisional application No. 62/705,318, filed on Jun. 22, 2020.

(51) Int. Cl.

| | |
|---|---|
| ***C07H 21/04*** | (2006.01) |
| ***A61K 31/713*** | (2006.01) |
| ***A61K 45/06*** | (2006.01) |
| ***A61M 5/31*** | (2006.01) |
| ***A61P 31/14*** | (2006.01) |
| ***C12N 15/113*** | (2010.01) |

(52) U.S. Cl.

CPC .......... *C12N 15/113* (2013.01); *A61K 31/713* (2013.01); *A61K 45/06* (2013.01); *A61M 5/3137* (2013.01); *A61P 31/14* (2018.01); *A61M 2005/3139* (2013.01); *A61M 2205/586* (2013.01); *C12N 2310/14* (2013.01); *C12N 2320/31* (2013.01); *C12N 2320/35* (2013.01)

(58) Field of Classification Search

CPC .......................... C12N 15/113; C12N 2310/14

See application file for complete search history.

(56) References Cited

U.S. PATENT DOCUMENTS

| | | | | |
|---|---|---|---|---|
| 4,522,811 A | | 6/1985 | Eppstein | |
| 4,695,623 A | | 9/1987 | Stabinsky | |
| 4,897,471 A | | 1/1990 | Stabinsky | |
| 7,157,559 B2 | | 1/2007 | Brady | |
| 11,590,156 B2 | * | 2/2023 | Li | A61K 31/7088 |

FOREIGN PATENT DOCUMENTS

| | | |
|---|---|---|
| WO | 2000053722 | 9/2000 |
| WO | 20080022309 | 2/2008 |
| WO | 2011104169 | 9/2011 |
| WO | 2012083185 | 6/2012 |
| WO | 2016077349 | 5/2016 |
| WO | 2017019891 | 2/2017 |
| WO | 2018027106 A2 | 2/2018 |
| WO | 2020163747 A1 | 8/2020 |

OTHER PUBLICATIONS

Varunok et al., "Evaluation of pharmacokinetics, user handling, and tolerability of peginterferon alfa-2a (40 kDa) delivered via a disposable autoinjector device", Patient Preference and Adherence, vol. 5, pp. 587-599 (2011).

Durantel David et al, "New antiviral targets for innovative treatment concepts for hepatitis B virus and hepatitis delta virus", Journal of Hepatology, Elsevier, Amsterdam, NL, (Apr. 12, 2016), vol. 64, No. 1.

Petersen Jörg et al., "Aiming for cure in HBV and HDV infection", Journal of Hepatology, vol. 65, issue 4 (Oct. 2016) pp. 835-848.

Zhimin Guo et al, "Therapeutic Strategies and New Intervention Points in Chronic Hepatitis Delta Virus Infection", International Journal of Molecular Sciences, (Aug. 18, 2015), vol. 16, No. 8, pp. 19537-19552.

* cited by examiner

*Primary Examiner* — Amy Rose Hudson

(57) ABSTRACT

Described are RNA interference (RNAi) agents for treating a Hepatitis D Virus (HDV) infection in a subject in need thereof.

11 Claims, No Drawings

Specification includes a Sequence Listing.

SEQUENCE LISTING

<160> NUMBER OF SEQ ID NOS: 19

<210> SEQ ID NO 1
<211> LENGTH: 21
<212> TYPE: RNA
<213> ORGANISM: Artificial Sequence
<220> FEATURE:
<223> OTHER INFORMATION: HBV RNAi Agent antisense strand modified sequence

<400> SEQUENCE: 1
agaaaauuga gagaagucca c 21

<210> SEQ ID NO 2
<211> LENGTH: 21
<212> TYPE: RNA
<213> ORGANISM: Artificial Sequence
<220> FEATURE:
<223> OTHER INFORMATION: HBV RNAi Agent antisense strand modified sequence

<400> SEQUENCE: 2
agaaaauuga gagaagucca c 21

<210> SEQ ID NO 3
<211> LENGTH: 23
<212> TYPE: RNA
<213> ORGANISM: Artificial Sequence
<220> FEATURE:
<223> OTHER INFORMATION: HBV RNAi Agent antisense strand modified sequence

<400> SEQUENCE: 3
agaaaauuga gagaagucca cuu 23

<210> SEQ ID NO 4
<211> LENGTH: 22
<212> TYPE: RNA
<213> ORGANISM: Artificial Sequence
<220> FEATURE:
<223> OTHER INFORMATION: HBV RNAi Agent antisense strand modified sequence

<400> SEQUENCE: 4
agaaaauuga gagaagucca cc 22

<210> SEQ ID NO 5
<211> LENGTH: 21
<212> TYPE: RNA
<213> ORGANISM: Artificial Sequence
<220> FEATURE:
<223> OTHER INFORMATION: HBV RNAi Agent antisense strand unmodified sequence

<400> SEQUENCE: 5
agaaaauuga gagaagucca c 21

<210> SEQ ID NO 6
<211> LENGTH: 23
<212> TYPE: RNA
<213> ORGANISM: Artificial Sequence
<220> FEATURE:
<223> OTHER INFORMATION: HBV RNAi Agent antisense strand unmodified sequence

<400> SEQUENCE: 6
agaaaauuga gagaagucca cuu 23

<210> SEQ ID NO 7
<211> LENGTH: 22
<212> TYPE: RNA
<213> ORGANISM: Artificial Sequence
<220> FEATURE:
<223> OTHER INFORMATION: HBV RNAi Agent antisense strand unmodified
sequence

<400> SEQUENCE: 7
agaaaauuga gagaagucca cc 22

<210> SEQ ID NO 8
<211> LENGTH: 21
<212> TYPE: RNA
<213> ORGANISM: Artificial Sequence
<220> FEATURE:
<223> OTHER INFORMATION: HBV RNAi Agent antisense strand modified
sequence

<400> SEQUENCE: 8
uaccaauuua ugccuacagc g 21

<210> SEQ ID NO 9
<211> LENGTH: 21
<212> TYPE: RNA
<213> ORGANISM: Artificial Sequence
<220> FEATURE:
<223> OTHER INFORMATION: HBV RNAi Agent antisense strand unmodified
sequence

<400> SEQUENCE: 9
uaccaauuua ugccuacagc g 21

<210> SEQ ID NO 10
<211> LENGTH: 21
<212> TYPE: RNA
<213> ORGANISM: Artificial Sequence
<220> FEATURE:
<223> OTHER INFORMATION: HBV RNAi Agent sense strand modified sequence

<400> SEQUENCE: 10
guggacuucu cucaauuuuc u 21

<210> SEQ ID NO 11
<211> LENGTH: 21
<212> TYPE: RNA
<213> ORGANISM: Artificial Sequence
<220> FEATURE:
<223> OTHER INFORMATION: HBV RNAi Agent sense strand modified sequence

<400> SEQUENCE: 11
guggacuucu cucaauuuuc u 21

<210> SEQ ID NO 12
<211> LENGTH: 22
<212> TYPE: RNA
<213> ORGANISM: Artificial Sequence
<220> FEATURE:
<223> OTHER INFORMATION: HBV RNAi Agent sense strand modified sequence

<400> SEQUENCE: 12
gguggacuuc ucucaauuuu cu 22

<210> SEQ ID NO 13
<211> LENGTH: 21

```
<212> TYPE: RNA
<213> ORGANISM: Artificial Sequence
<220> FEATURE:
<223> OTHER INFORMATION: HBV RNAi Agent sense strand modified sequence

<400> SEQUENCE: 13

guggacuucu cucaauuuuc u                                              21


<210> SEQ ID NO 14
<211> LENGTH: 21
<212> TYPE: RNA
<213> ORGANISM: Artificial Sequence
<220> FEATURE:
<223> OTHER INFORMATION: HBV RNAi Agent sense strand unmodified sequence

<400> SEQUENCE: 14

guggacuucu cucaauuuuc u                                              21


<210> SEQ ID NO 15
<211> LENGTH: 22
<212> TYPE: RNA
<213> ORGANISM: Artificial Sequence
<220> FEATURE:
<223> OTHER INFORMATION: HBV RNAi Agent sense strand unmodified sequence

<400> SEQUENCE: 15

gguggacuuc ucucaauuuu cu                                             22


<210> SEQ ID NO 16
<211> LENGTH: 21
<212> TYPE: RNA
<213> ORGANISM: Artificial Sequence
<220> FEATURE:
<223> OTHER INFORMATION: HBV RNAi Agent sense strand modified sequence

<400> SEQUENCE: 16

cgcuguaggc auaaauuggu a                                              21


<210> SEQ ID NO 17
<211> LENGTH: 21
<212> TYPE: RNA
<213> ORGANISM: Artificial Sequence
<220> FEATURE:
<223> OTHER INFORMATION: HBV RNAi Agent sense strand modified sequence

<400> SEQUENCE: 17

cgcuguaggc auaaauuggu a                                              21


<210> SEQ ID NO 18
<211> LENGTH: 21
<212> TYPE: RNA
<213> ORGANISM: Artificial Sequence
<220> FEATURE:
<223> OTHER INFORMATION: HBV RNAi Agent sense strand modified sequence

<400> SEQUENCE: 18

cgcuguaggc auaaauuggu a                                              21
```

-continued

```
<210> SEQ ID NO 19
<211> LENGTH: 21
<212> TYPE: RNA
<213> ORGANISM: Artificial Sequence
<220> FEATURE:
<223> OTHER INFORMATION: HBV RNAi Agent sense strand unmodified sequence

<400> SEQUENCE: 19

cgcuguaggc auaaauuggu a                                             21
```

COMPOSITIONS AND METHODS FOR TREATMENT OF HEPATITIS D VIRUS INFECTION

CROSS REFERENCE TO RELATED APPLICATION

This application claims priority to U.S. Provisional Application No. 62/705,318, filed Jun. 22, 2020, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "065814_44US2_Sequence_Listing" and a creation date of Jun. 11, 2021 and having a size of 5 kb. The sequence listing submitted via EFS-Web is part of the specification and is herein incorporated by reference in its entirety.

FIELD OF INVENTION

The present disclosure relates generally to compositions and kits comprising a RNA interference (RNAi) component and/or an anti-HBV agent and/or anti-HDV agent, more particularly an anti-HBV agent, wherein the anti-HBV agent is a nucleos(t)ide analog (NUC) or an interferon (IFN) and their use for treating hepatitis D virus infection.

BACKGROUND

The hepatitis D virus (HDV) is a small, spherical virus. It has an outer coat containing three kinds of hepatitis B virus (HBV) envelope proteins (i.e., large, medium, and small hepatitis B surface antigens) and host lipids surrounding an inner nucleocapsid. The nucleocapsid contains single-stranded, circular RNA and about 200 molecules of hepatitis D antigen (HDAg) for each genome. The central region of HDAg has been shown to bind RNA. Several interactions are also mediated by a coiled-coil region at the amino-terminus of HDAg.

The hepatitis D circular genome is unique among animal viruses because of the high GC nucleotide content. The HDV genome exists as a negative sense, single-stranded, closed circular RNA. The nucleotide sequence is 70% self-complementary, allowing the genome to form a partially double-stranded, rod-like RNA structure. With a genome of approximately 1700 nucleotides, HDV is the smallest virus known to infect animals.

Infection with HDV leads to a chronic liver disease for which no effective treatment is approved. HDV infection only occurs in the context of co-infection with HBV as it requires the presence of HBsAg for HDV to form infectious virus particles.

There is a high unmet medical need for patients co-infected with HBV and HDV since co-infection is associated with earlier development of liver cirrhosis, increased risk for development of hepatocellular carcinoma (HCC) and increased liver-related and overall mortality. At present, there are no drugs approved for the treatment of chronic HDV infection. The currently available therapeutic options for hepatitis D are suboptimal and untreated patients have a rapid progression of disease.

The disclosures of all publications, patents, patent applications and published patent applications referred to herein are hereby incorporated herein by reference in their entirety.

BRIEF SUMMARY

Provided herein is a method of treating a Hepatitis D Virus (HDV) infection in a subject in need thereof, preferably a human subject in need thereof, wherein the method comprises administering to the subject an effective amount of a pharmaceutical composition comprising an RNAi component having:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is administered to the subject via intravenous or subcutaneous injection. In certain embodiments, the RNAi component is administered once monthly (or Q4W), once every two months (or Q8W), or once every three months (or Q12W), more particularly once monthly. In certain embodiments, the RNAi component is administered in a dose of about 40-200 mg, more particularly 100 mg, 150 mg, or 200 mg, more particularly 100 mg.

Also provided herein is a pharmaceutical composition for use in the treatment of a Hepatitis D Virus infection in a subject in need thereof, preferably a human subject in need thereof, wherein the pharmaceutical composition comprises an effective amount of an RNAi component, wherein the RNAi component comprises:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is formulated for administration to the subject via intravenous or subcutaneous injection. In certain embodiments, the RNAi component is formulated for administration once monthly (or Q4W), once every two months (or Q8W), or once every three months (or Q12W), more particularly once monthly. In certain embodiments, the RNAi component is administered in a dose of about 40-200 mg, more particularly 100 mg, 150 mg, or 200 mg, more particularly 100 mg.

Another general aspect of the application relates to a combination or a kit comprising:

(1) a pharmaceutical composition comprising an effective amount of an RNAi component having:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19; and (2) a pharmaceutical composition comprising an effective amount of an anti-HBV agent and/or an anti-HDV agent, more particularly an anti-HBV agent, wherein the anti-HBV agent is a nucleos(t)ide analog (NUC) or an interferon (IFN), wherein the combination or kit is for use in treating a Hepatitis D Virus (HDV) infection in a subject in need thereof, preferably a human subject in need thereof.

Another general aspect of the application relates to a combination or a kit comprising:

(1) a pharmaceutical composition comprising an effective amount of an RNAi component having:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19; and (2) a pharmaceutical composition comprising an effective amount of an anti-HBV agent and/or an anti-HDV agent, more particularly an anti-HDV agent, wherein the anti-HDV agent is an HDV entry inhibitor and/or a farnesyl transferase inhibitor, wherein the combination or kit is for use in treating a Hepatitis D Virus (HDV) infection in a subject in need thereof, preferably a human subject in need thereof.

Also provided herein is an effective amount of an RNAi component and optionally an anti-HBV agent and/or an anti-HDV agent, more particularly optionally an anti-HBV agent, wherein the anti-HBV agent is a nucleos(t)ide analog (NUC) or an interferon (IFN), in the manufacture of a medicament for treating a Hepatitis D Virus (HDV) infection in a subject in need thereof, preferably a human subject in need thereof, wherein:

(a) the RNAi component comprises:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19; and (b) the nucleoside analog or nucleotide analog is preferably entecavir, tenofovir disoproxil fumarate, tenofovir alafenamide, lamivudine, telbivudine, or a combination thereof, wherein the RNAi component is for administration to the subject in need thereof via intravenous or subcutaneous injection. In certain embodiments, the RNAi component is for administration once monthly (or Q4W), once every two months (or Q8W), or once every three months (or Q12W), more particularly once monthly administration. In certain embodiments, the RNAi component is administered in a dose of about 40-200 mg, more particularly 100 mg, 150 mg, or 200 mg, more particularly 100 mg.

In any of the methods or other disclosures herein, the treatment further comprises administering an effective amount of an anti-HBV agent and/or an anti-HDV agent, more particularly an effective amount of an anti-HBV agent, wherein the anti-HBV agent is a nucleos(t)ide analog (NUC) or an interferon (IFN), more particularly an effective amount of a nucleoside analog or a nucleotide analog. In some embodiments, the nucleoside analog or nucleotide analog can, for example, be entecavir, tenofovir disoproxil fumarate, tenofovir alafenamide, lamivudine, telbivudine, or a combination thereof, more particularly entecavir, tenofovir disoproxil fumurate, tenofovir alafenamide, or a combination thereof.

In any of the methods or other disclosures herein, the at least one other anti-Hepatitis B Virus (HBV) agent or compound is at least one anti-HBV agent or compound other than the RNAi component of the application, more particularly other than an anti-HBV siRNA, more particularly at least one anti-HBV agent selected from the group consisting of Direct Acting Antivirals (such as nucleos(t)ide analogs, more particularly entecavir, tenofovir disoproxil fumarate, tenofovir alafenamide, lamivudine, telbivudine, or a combination thereof), cytokines (such as interferon, more particularly interferon alpha, interferon lambda, pegylated interferon, pegylated interferon alpha), HBV DNA polymerase inhibitors; Immunomodulators; Toll-like receptor modulators (e.g., Toll-like receptor 7 modulators; Toll-like receptor 8 modulators; Toll-like receptor 3 modulators; Toll like receptor 9 modulators); Interferon alpha receptor ligands; Hyaluronidase inhibitors; Modulators of IL-10; HBsAg inhibitors; Cyclophilin inhibitors; HBV Prophylactic vaccines; HBV Therapeutic vaccines; HBV viral entry inhibitors; Endonuclease modulators; Inhibitors of ribonucleotide reductase; Hepatitis B virus E antigen inhibitors; HBV antibodies targeting the surface antigens of the hepatitis B virus; HBV antibodies; CCR2 chemokine antagonists; Thymosin agonists; Cytokines, such as IL12; Capsid Assembly Modulators, Nucleoprotein inhibitors (HBV core or capsid protein inhibitors); Nucleic Acid Polymers (NAPs); Stimulators of retinoic acid-inducible gene 1; Stimulators of NOD2; Hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, CTLA-4 inhibitors; Agonists of co-stimulatory receptors that are expressed on immune cells (more particularly T cells), such as CD27 and CD28; BTK inhibitors; Other drugs for treating HBV; IDO inhibitors; Arginase inhibitors; and KDM5 inhibitors.

In any of the methods or other disclosures herein, the at least one other anti-HDV agent or compound is at least one anti-HDV agent or compound other than the RNAi component of the application, more particularly an HDV entry inhibitor (e.g., Myrrcludex (bulevirtide)) and/or a farnesyl transferase inhibitor (e.g., Lonafarnib). In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component. In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component, and is stopped once the administration of the RNAi component starts.

In any of the methods or other disclosures herein, the nucleos(t)ide analog (NUC) or interferon (IFN) is not administered prior to the RNAi component. In some embodiments, the RNAi component is administered prior to or concurrently with the nucleos(t)ide analog (NUC) or interferon (IFN).

In any of the methods or other disclosures herein, the subject comprises a HDV/Hepatitis B Virus (HBV) co-infection. In some embodiments, the subject further comprises cirrhosis, more particularly compensated cirrhosis. In some embodiments, the subject is a patient without cirrhosis.

In any of the methods or other disclosures herein, in one variation the first or the second RNAi agent comprises at least one modified nucleotide or at least one modified internucleoside linkage. In another variation, substantially all of the nucleotides in the first and the second RNAi agents are modified nucleotides. In a further variation, the first or the second RNAi agent further comprises a targeting ligand that is conjugated to the first or the second RNAi agent. In one aspect, the targeting ligand comprises N-acetyl-galactosamine. In a particular aspect, the targeting ligand is selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s. In one variation, the targeting ligand is (NAG25), (NAG25)s, (NAG31), (NAG31)s, (NAG37), or (NAG37)s. In another variation, the targeting ligand is conjugated to the sense strand of the first or the second RNAi agent. In another variation, the targeting ligand is conjugated to the 5' terminus of the sense stand of the first or the second RNAi agent. In still another variation, the first and the second RNAi agents independently comprise a duplex selected from the group consisting of: an antisense strand comprising SEQ ID NO: 1 and a sense strand comprising SEQ ID NO: 10; an antisense strand comprising SEQ ID NO:2 and a sense strand comprising SEQ ID NO: 11; an antisense strand comprising SEQ ID NO: 3 and a sense strand comprising SEQ ID NO: 11; an antisense strand comprising SEQ ID NO: 4 and a sense strand comprising SEQ ID NO: 12; an antisense strand comprising SEQ ID NO: 8 and a sense strand comprising SEQ ID NO: 16; an antisense strand comprising SEQ ID NO: 8 and a sense strand comprising SEQ ID NO: 17; an antisense strand comprising SEQ ID NO:2 and a sense strand comprising SEQ ID NO: 13; and an antisense strand comprising SEQ ID NO: 8 and a sense strand comprising SEQ ID NO: 18. In a particular variation, the first and the second RNAi agents are each independently conjugated to a targeting ligand comprising N-acetyl-galactosamine, and the first and the second RNAi agents independently comprise a duplex selected from the group consisting of: an antisense strand comprising SEQ ID NO:2 and a sense strand comprising SEQ ID NO: 11; an antisense strand comprising SEQ ID NO: 4 and a sense strand comprising SEQ ID NO: 12; an antisense strand comprising SEQ ID NO: 8 and a sense strand comprising SEQ ID NO: 16; an antisense strand comprising SEQ ID NO:2 and a sense strand comprising SEQ ID NO: 13; and an antisense strand comprising SEQ ID NO: 8 and a sense strand comprising SEQ ID NO: 18. In still another variation, the ratio of the first RNAi agent to the second RNAi agent by weight is in the range of about 1:2 to about 5:1. In another variation, the ratio of the first RNAi agent to the second RNAi agent by weight is about 2:1. In certain aspects, the first and the second RNAi agents are each independently conjugated to (NAG37)s, the first RNAi agent comprises an antisense strand comprising SEQ ID NO: 2 and a sense strand comprising SEQ ID NO: 11, and the second RNAi agent comprises an antisense strand comprising SEQ ID NO: 8 and a sense strand comprising SEQ ID NO: 16.

In any of the methods or other disclosures herein, the RNAi component is contained in a syringe, for example a glass syringe, and wherein the syringe is optionally suitable for self-administration of the RNAi component by the patient or for administration of the RNAi component to the patient by an untrained personnel.

In any of the methods or other disclosures herein, the syringe is suitable for self-administration of the RNAi component by the patient, and wherein the syringe is placed in an ergonomic shell or grip to stabilize the syringe for self-injection by the patient, or is provided in an autoinjector device.

Other aspects, features and advantages of the invention will be apparent from the following disclosure, including the detailed description of the invention and its preferred embodiments and the appended claims.

DETAILED DESCRIPTION

The following description is presented to enable a person of ordinary skill in the art to make and use the various embodiments. Descriptions of specific compositions, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications, and publications cited herein are incorporated by reference as if set forth fully herein.

It must be noted that as used herein and in the appended claims, the singular forms "a," "an," and "the," include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1 mg/mL to 10 mg/mL includes 0.9 mg/mL to 11 mg/mL. As used herein, the use of a numerical range expressly includes all possible subranges, all individual numerical values within that range, including integers within such ranges and fractions of the values unless the context clearly indicates otherwise.

By "optional" or "optionally" is meant that the event described subsequent thereto may or may not happen. This term encompasses the cases that the event may or may not happen.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

The pharmaceutically acceptable salts according to the invention may be prepared from the parent compound containing acidic or basic group through conventional chemical procedures. Generally, such salts can be prepared through the reaction of the compounds in the form of free acid or base with stoichiometric appropriate base or acid in water, organic solvent or the mixture thereof. Typically, nonaqueous medium like ether, ethyl acetate, ethanol, isopropanol, acetonitrile etc. are preferable.

The terms "patient" and "subject" refer to an animal, such as a mammal, bird, or fish. In some embodiments, the patient or subject is a mammal. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human. In some embodiments, the patient or subject is a human, for example a human that has been or will be the object of treatment, observation or experiment. The compounds, compositions, and methods described herein can be useful in both human therapy and veterinary applications.

The term "therapeutically effective amount" or "effective amount" refers to that amount of a RNAi component, nucleos(t)ide analog (NUC), or pharmaceutical composition disclosed and/or described herein that is sufficient to affect treatment, as defined herein, when administered to a subject in need of such treatment. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount can be ascertained experimentally, for example by assaying blood concentration of the compound, or theoretically, by calculating bioavailability by one of ordinary skill in the art in view of the present disclosure.

In particular embodiments of the application, a therapeutically effective amount refers to the amount of a composition or therapeutic combination which is sufficient to achieve one, two, three, four, or more of the following effects: (i) reduce or ameliorate the severity of an HDV infection or a symptom associated therewith; (ii) reduce the duration of an HDV infection or symptom associated therewith; (iii) prevent the progression of an HDV infection or symptom associated therewith; (iv) cause regression of an HDV infection or symptom associated therewith; (v) prevent the development or onset of an HDV infection, or symptom associated therewith; (vi) prevent the recurrence of an HDV infection or symptom associated therewith; (vii) reduce hospitalization of a subject having an HDV infection; (viii) reduce hospitalization length of a subject having an HDV infection; (ix) increase the survival of a subject with an HDV infection; (x) eliminate an HDV infection in a subject; (xi) inhibit or reduce HDV replication in a subject; and/or (xii) enhance or improve the prophylactic or therapeutic effect(s) of another therapy.

A therapeutically effective amount can also be an amount of the pharmaceutical composition sufficient to decrease a serum HDV RNA level, more particularly, sufficient to decrease a serum HDV RNA level to an undetectable serum HDV RNA level. Alternative or complementary examples of target indexes include, but are not limited to, a serum ALT concentration of 40 U/L or lower if the subject is a male subject or of 30 U/L or lower if the subject is a female subject, or a relative reduction (from baseline (or from level at start of treatment)) of serum ALT concentration by at least 40%, more particularly by at least 50%; a HBeAg-negative serum; a serum HBsAg level of 100 IU/mL or lower, more particularly of 10 IU/mL or lower, more particularly HBsAg seroclearance; and HBs seroconversion. As used herein, the term "serum ALT" can encompass ALT from any blood product or component, e.g., blood ALT or plasma ALT.

As used herein, the terms and phrases "in combination," "in combination with," "co-delivery," and "administered together with" in the context of the administration of two or more therapies or components to a subject refers to simultaneous administration or subsequent administration of two or more therapies or components, such as two vectors, e.g., DNA plasmids, peptides, or a therapeutic combination and an adjuvant. "Simultaneous administration" can be administration of the two or more therapies or components at least within the same day. When two components are "administered together with" or "administered in combination with," they can be administered in separate compositions sequentially within a short time period, such as 24, 20, 16, 12, 8 or 4 hours, or within 1 hour, or they can be administered in a single composition at the same time. "Subsequent administration" can be administration of the two or more therapies or components in the same day or on separate days. The use of the term "in combination with" does not restrict the order in which therapies or components are administered to a subject. For example, a first therapy or component (e.g. an RNAi component) can be administered prior to (e.g., 5 minutes to one hour before), concomitantly with or simultaneously with, or subsequent to (e.g., 5 minutes to one hour after) the administration of a second therapy or component (e.g., a nucleos(t)ide analog (NUC) or interferon (INF)). In some embodiments, a first therapy or component (e.g. an RNAi component) and a second therapy or component (e.g., a nucleos(t)ide analog (NUC) or IFN) are administered in the same composition. In other embodiments, a first therapy or component (e.g. an RNAi component) and a second therapy or component (e.g., a nucleos(t)ide analog (NUC) or IFN) are administered in separate compositions, such as two separate compositions.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. For example, while embodiments of RNAi component described herein may contain particular components arranged in a particular order, those having ordinary skill in the art will appreciate that the concepts disclosed herein may equally apply to other components arranged in other orders that can be used in RNAi of the application. The application contemplates use of any of the applicable components in any combination that can be used the application, whether or not a particular combination is expressly described. The invention generally relates to a therapeutic combination comprising one or more HBV RNAi and a nucleos(t)ide analog (NUC) or interferon (INF).

Combination

Provided herein is a combination of an effective amount of an RNAi component and an effective amount of at least one anti-Hepatitis B Virus (HBV) agent and/or at least one anti-HDV agent, more particularly at least one anti-HBV agent, wherein the anti-HBV agent is selected from a nucleos(t)ide analog (NUC) or an interferon.

RNAi Component

In one aspect, the RNAi component comprises one or more RNAi agents. Each RNAi agent disclosed herein includes at least a sense strand and an antisense strand. The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. The sense and antisense strands can be either the same length or different lengths. The HBV RNAi agents disclosed herein have been designed to include antisense strand sequences that are at least partially complementary to a sequence in the HBV genome that is conserved across the majority of known serotypes of HBV. The RNAi agents described herein, upon delivery to a cell expressing HBV, inhibit the expression of one or more HBV genes in vivo or in vitro.

An RNAi agent includes a sense strand (also referred to as a passenger strand) that includes a first sequence, and an antisense strand (also referred to as a guide strand) that includes a second sequence. A sense strand of the HBV RNAi agents described herein includes a core stretch having at least about 85% identity to a nucleotide sequence of at least 16 consecutive nucleotides in an HBV mRNA. In some embodiments, the sense strand core nucleotide stretch having at least about 85% identity to a sequence in an HBV mRNA is 16, 17, 18, 19, 20, 21, 22, or 23 nucleotides in length. An antisense strand of an HBV RNAi agent comprises a nucleotide sequence having at least about 85% complementary over a core stretch of at least 16 consecutive nucleotides to a sequence in an HBV mRNA and the corresponding sense strand. In some embodiments, the antisense strand core nucleotide sequence having at least about 85% complementarity to a sequence in an HBV mRNA or the corresponding sense strand is 16, 17, 18, 19, 20, 21, 22, or 23 nucleotides in length.

In some embodiments, the RNAi component comprises a first RNAi agent comprising an antisense strand comprising a nucleotide sequence of any one of the following: SEQ ID NO:1, SEQ ID NO:2, SEQ ID NO:3, SEQ ID NO: 4, SEQ ID NO: 5, SEQ ID NO:6, and SEQ ID NO:7, and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15, or a second RNAi agent comprising an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19. In some embodiments, the RNAi component comprises a first RNAi agent comprising an antisense strand comprising a nucleotide sequence of any one of the following: SEQ ID NO:1, SEQ ID NO:2, SEQ ID NO:3, SEQ ID NO: 4, SEQ ID NO: 5, SEQ ID NO:6, and SEQ ID NO:7, and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15, and a second RNAi agent comprising an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19.

In some embodiments, the first and the second RNAi agents disclosed herein comprise any of the sequences in Table 1.

TABLE 1

Exemplary sequences for first and second RNAi agents

| Antisense | | Sense | |
|---|---|---|---|
| SEQ ID NO | Unmodified sequence (5' → 3') | SEQ ID NO | Unmodified sequence (5' → 3') |
| 5 | AGAAAAUUGAGAGAAGUCCAC | 14 | GUGGACUUCUCUCAAUUUUCU |
| 6 | AGAAAAUUGAGAGAAGUCCACUU | 14 | GUGGACUUCUCUCAAUUUUCU |
| 7 | AGAAAAUUGAGAGAAGUCCACC | 15 | GGUGGACUUCUCUCAAUUUUCU |
| 9 | UACCAAUUUAUGCCUACAGCG | 19 | CGCUGUAGGCAUAAAUUGGUA |

Targeting Group

In some embodiments, the RNAi agents are delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors or Dynamic Polyconjugates (DPCs) (see, for example WO 2000/053722, WO 2008/0022309, WO 2011/104169, and WO 2012/083185, each of which is incorporated herein by reference). In some embodiments, an RNAi agent is delivered to target cells or tissues by covalently linking the RNAi agent to a targeting group. In some embodiments, the targeting group can include a cell receptor ligand, such as an asialoglycoprotein receptor (ASGPr) ligand. In some embodiments, an ASGPr ligand includes or consists of a galactose derivative cluster. In some embodiments, a galactose derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer.

A targeting group can be linked to the 3' or 5' end of a sense strand or an antisense strand of an RNAi agent. In some embodiments, a targeting group is linked to the 3' or 5' end of the sense strand. In some embodiments, a targeting group is linked to the 5' end of the sense strand. In some embodiments, a targeting group is linked to the RNAi agent via a linker.

In some embodiments, the RNAi component comprises a combination or cocktail of a first and a second RNAi agent having different nucleotide sequences. In some embodiments, the first and the second RNAi agents are each separately and independently linked to targeting groups. In some embodiments, the first and the second RNAi agents are each linked to targeting groups comprised of N-acetyl-galactosamines. In some embodiments, when the first and the second RNAi agents are included in a composition, each of the RNAi agents is linked to the same targeting group. In some embodiments, when the first and the second RNAi agents are included in a composition, each of the RNAi agents is linked to different targeting groups, such as targeting groups having different chemical structures.

In some embodiments, targeting groups are linked to the first and the second RNAi agents without the use of an additional linker. In some embodiments, the targeting group is designed having a linker readily present to facilitate the linkage to the first or the second RNAi agent. In some embodiments, when the first and the second RNAi agents are included in a composition, the first and the second RNAi agents may be linked to the targeting groups using the same linkers. In some embodiments, when the first and the second RNAi agents are included in a composition, the first and the second RNAi agents are linked to the targeting groups using different linkers.

Examples of targeting groups and linking groups are provided in Table 2. The non-nucleotide group can be covalently linked to the 3' and/or 5' end of either the sense strand and/or the antisense strand. In some embodiments, the first or second RNAi agent contains a non-nucleotide group linked to the 3' and/or 5' end of the sense strand. In some embodiments, a non-nucleotide group is linked to the 5' end of the first or second RNAi agent sense strand. A non-nucleotide group may be linked directly or indirectly to the first or second RNAi agent via a linker/linking group. In some embodiments, a non-nucleotide group is linked to the first or second RNAi agent via a labile, cleavable, or reversible bond or linker.

Targeting groups and linking groups include the following, for which their chemical structures are provided below in Table 2: (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed above, as well as other targeting or linking groups, conjugated to the 5' and/or 3' end of the sequence.

TABLE 2

Structures Representing Various Modified Nucleotides, Targeting Groups, And Linking Groups

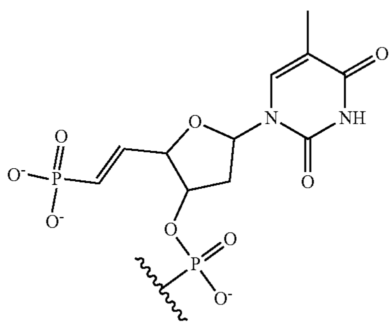 [SMILES: *P(=O)([O-])OC1CC(n2cc(C)c(=O)[nH]c2=O)OC1/C=C/P(=O)([O-])[O-]]

vpdT

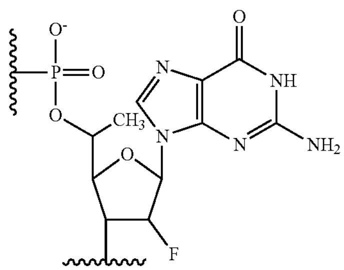 [SMILES: *C1C(F)C(n2cnc3c(=O)[nH]c(N)nc32)OC1C(C)OP(*)(=O)[O-]]

5Me-Gf

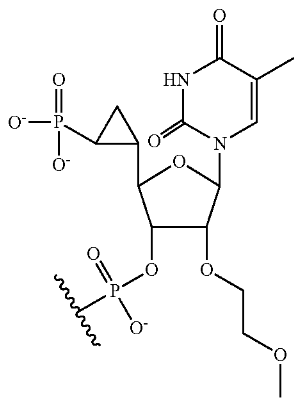 [SMILES: *P(=O)([O-])OC1C(C2CC2P(=O)([O-])[O-])OC(n2cc(C)c(=O)[nH]c2=O)C1OCCOC]

cPrpTM

TABLE 2-continued
| Structures Representing Various Modified Nucleotides, Targeting Groups, And Linking Groups |
| --- |
| 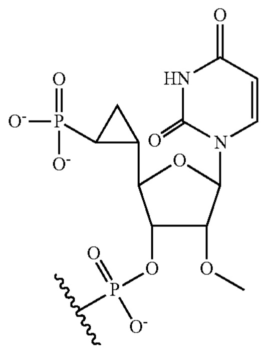 [SMILES: *P(=O)([O-])OC1C(C2CC2P(=O)([O-])[O-])OC(n2ccc(=O)[nH]c2=O)C1OC] |
| cPrpu |
| 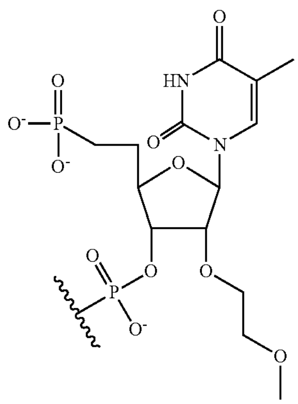 [SMILES: *P(=O)([O-])OC1C(CCP(=O)([O-])[O-])OC(n2cc(C)c(=O)[nH]c2=O)C1OCCOC] |
| epTM |
| 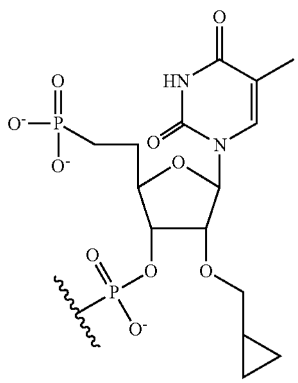 [SMILES: *P(=O)([O-])OC1C(CCP(=O)([O-])[O-])OC(n2cc(C)c(=O)[nH]c2=O)C1OCC1CC1] |
| epTcPr |

TABLE 2-continued
Structures Representing Various Modified Nucleotides, Targeting Groups, And Linking Groups
When positioned internally on oligonucleotide:
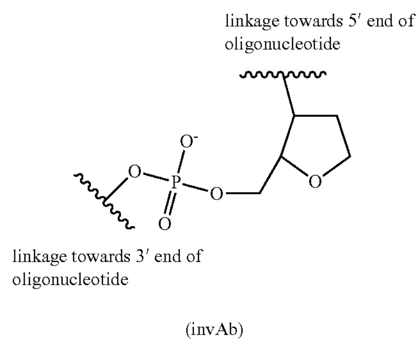
(invAb)
When positioned internally on oligonucleotide:
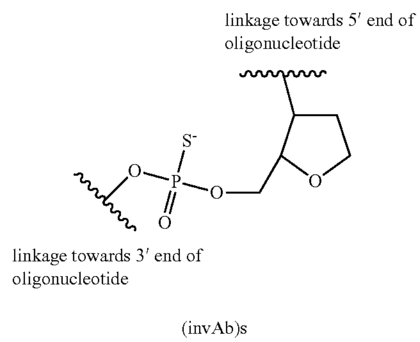
(invAb)s
When positioned at the 3' terminal end of oligonucleotide:
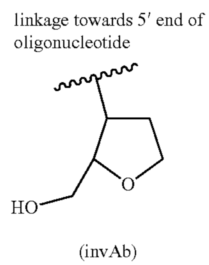
(invAb)
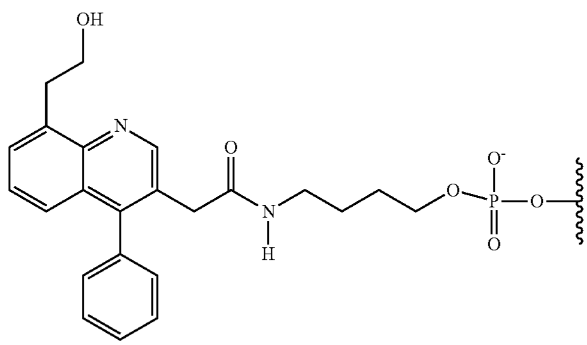 [SMILES: *OP(=O)([O-])OCCCCNC(=O)Cc1cnc2c(CCO)cccc2c1-c1ccccc1]
(PAZ)

TABLE 2-continued
| Structures Representing Various Modified Nucleotides, Targeting Groups, And Linking Groups |
|---|
| 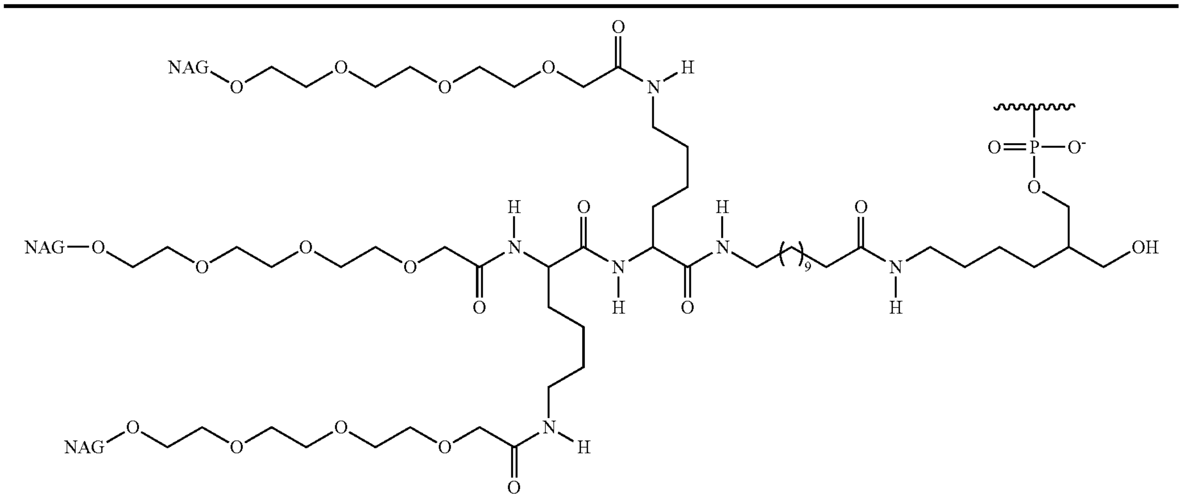 |
| (NAG13) |
| 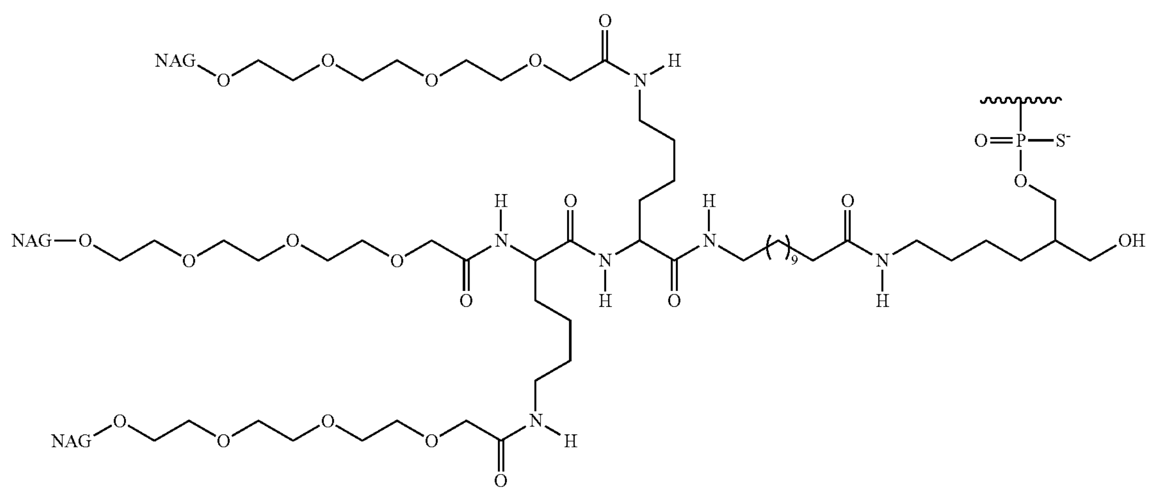 |
| (NAG13)s |
| 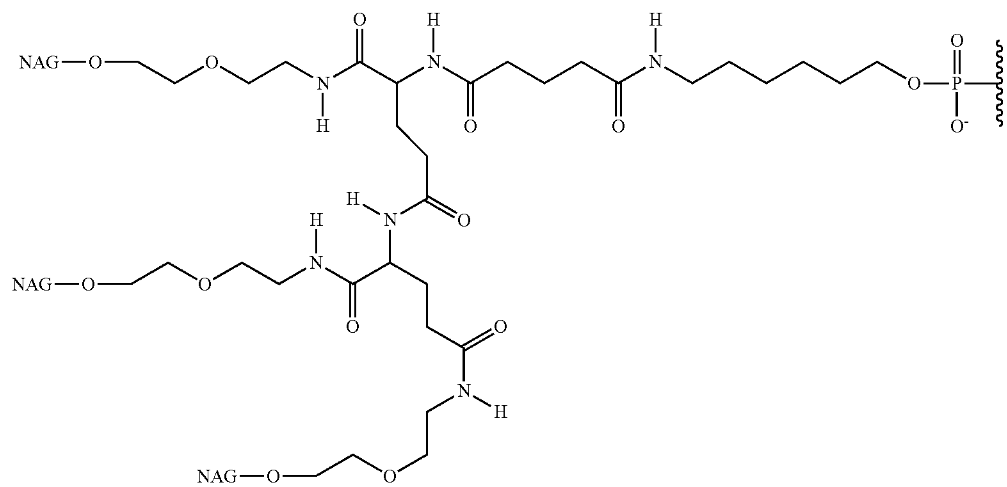 |
| (NAG18) |

TABLE 2-continued
| Structures Representing Various Modified Nucleotides, Targeting Groups, And Linking Groups |
|---|
| 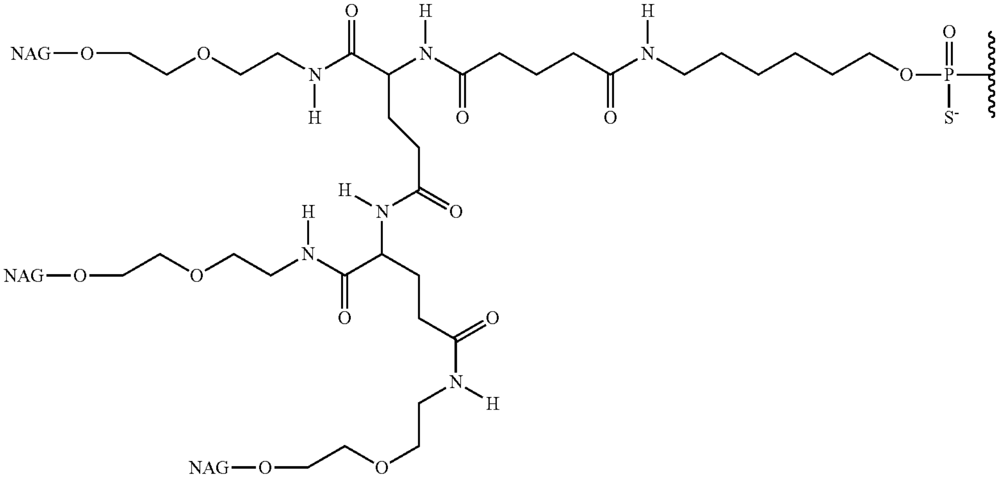 |
| (NAG18)s |
| 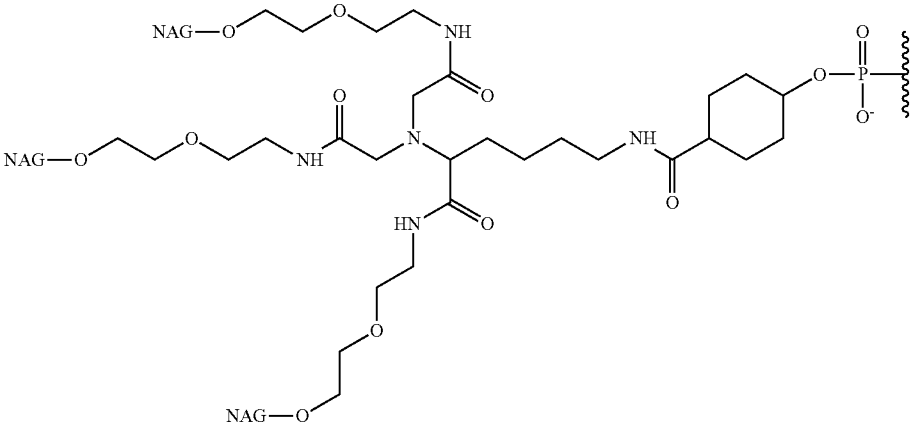 |
| (NAG24) |
| 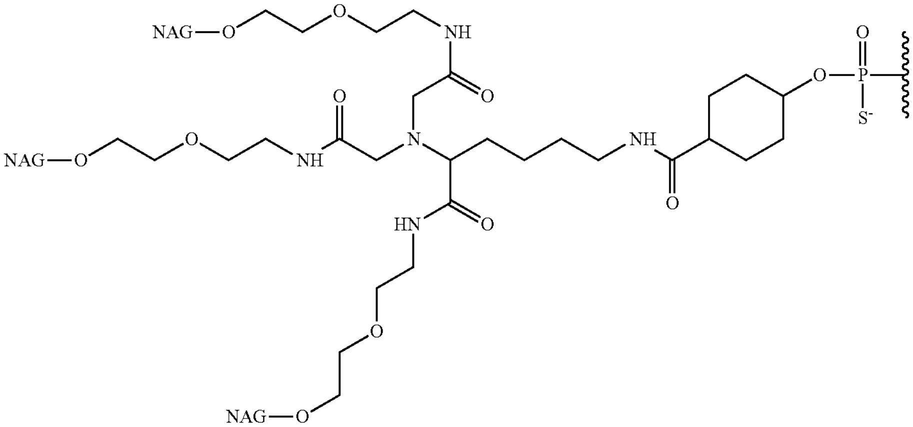 |
| (NAG24)s |

TABLE 2-continued
Structures Representing Various Modified Nucleotides, Targeting Groups, And Linking Groups
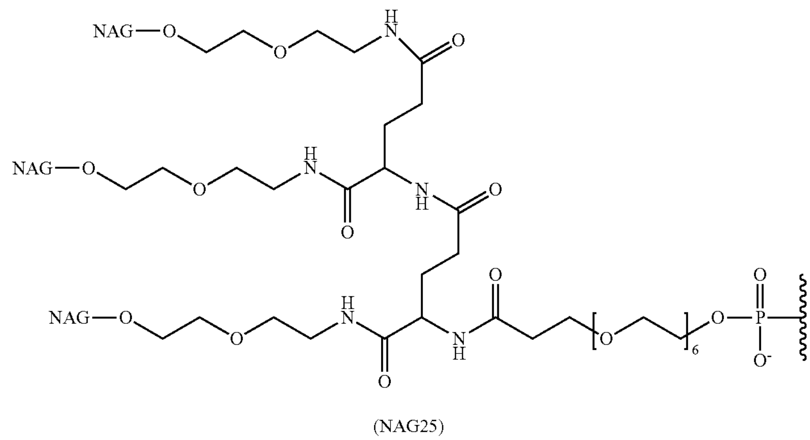
(NAG25)
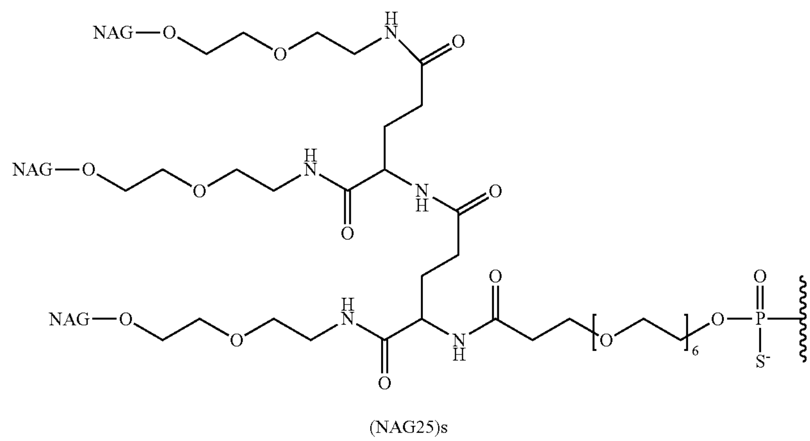
(NAG25)s
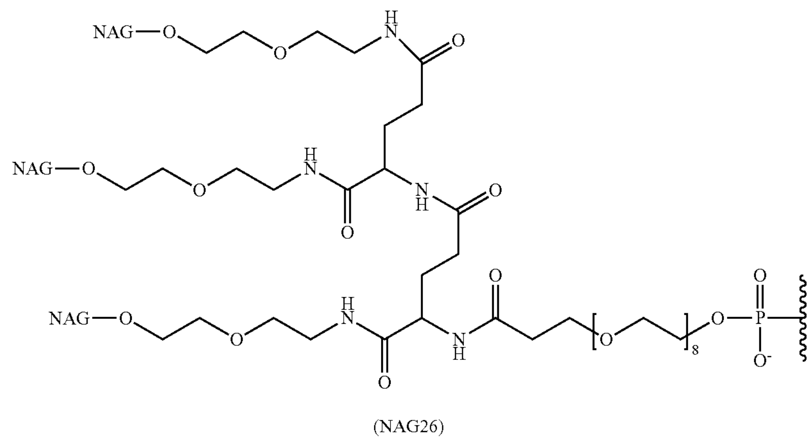
(NAG26)

TABLE 2-continued
Structures Representing Various Modified Nucleotides, Targeting Groups, And Linking Groups
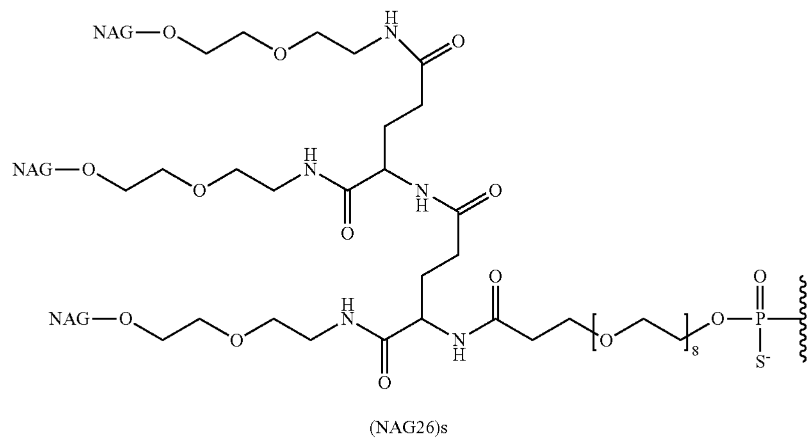
(NAG26)s
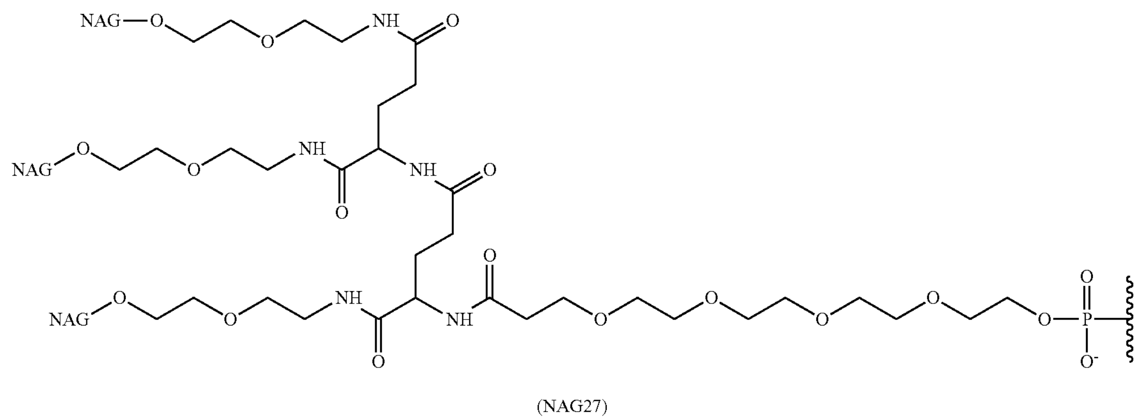
(NAG27)
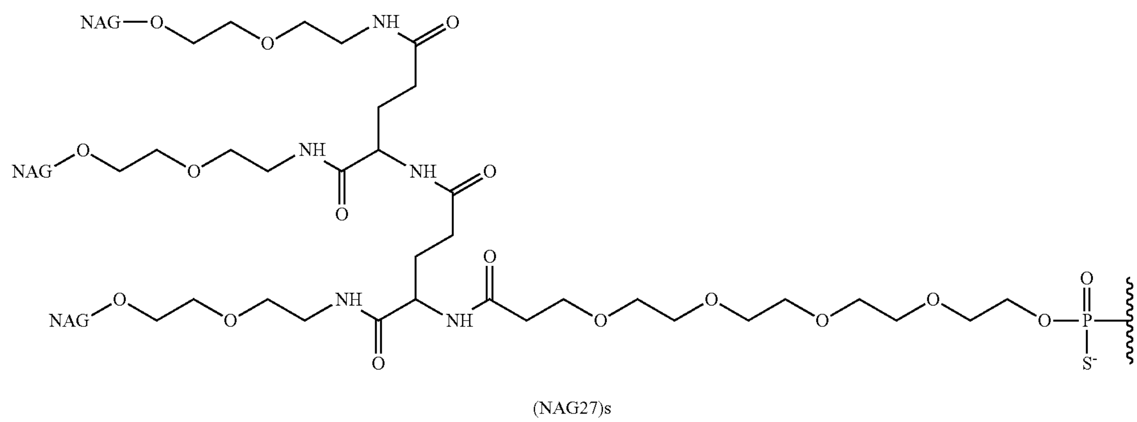
(NAG27)s TABLE 2-continued
Structures Representing Various Modified Nucleotides, Targeting Groups, And Linking Groups
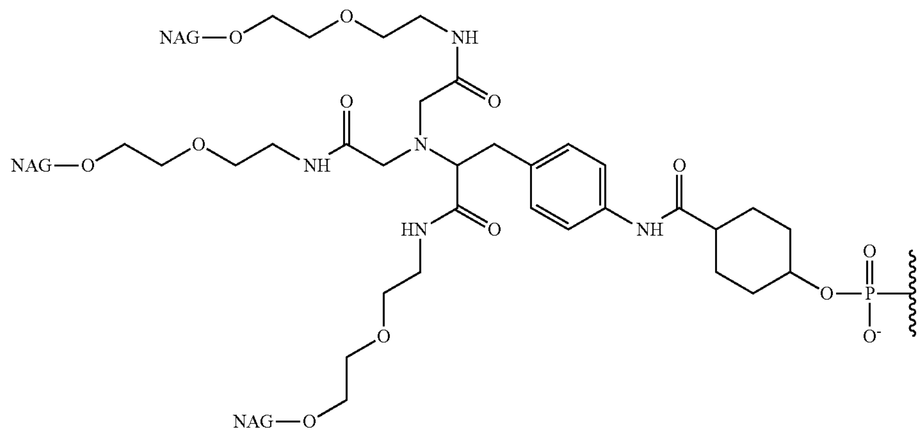
(NAG28)
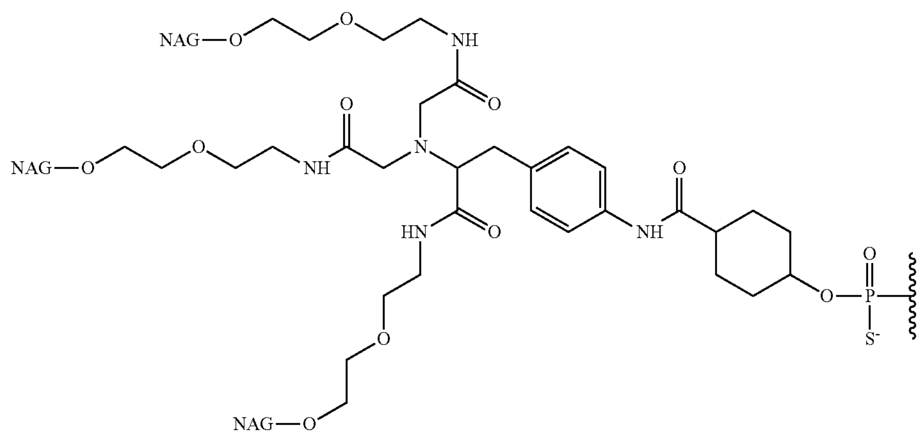
(NAG28)s TABLE 2-continued
Structures Representing Various Modified Nucleotides, Targeting Groups, And Linking Groups
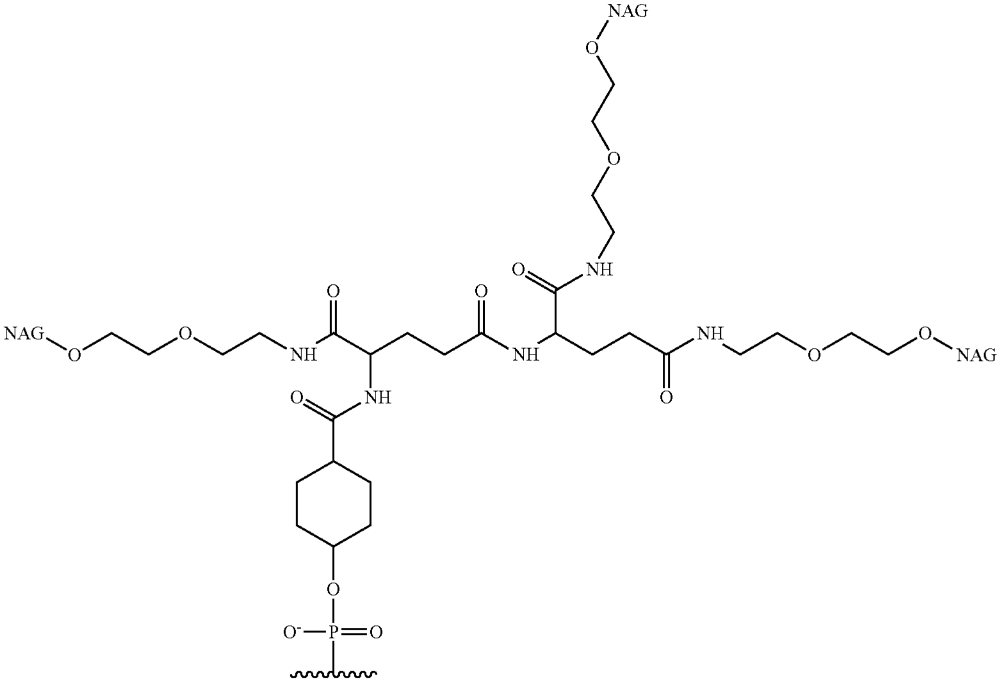
(NAG29)
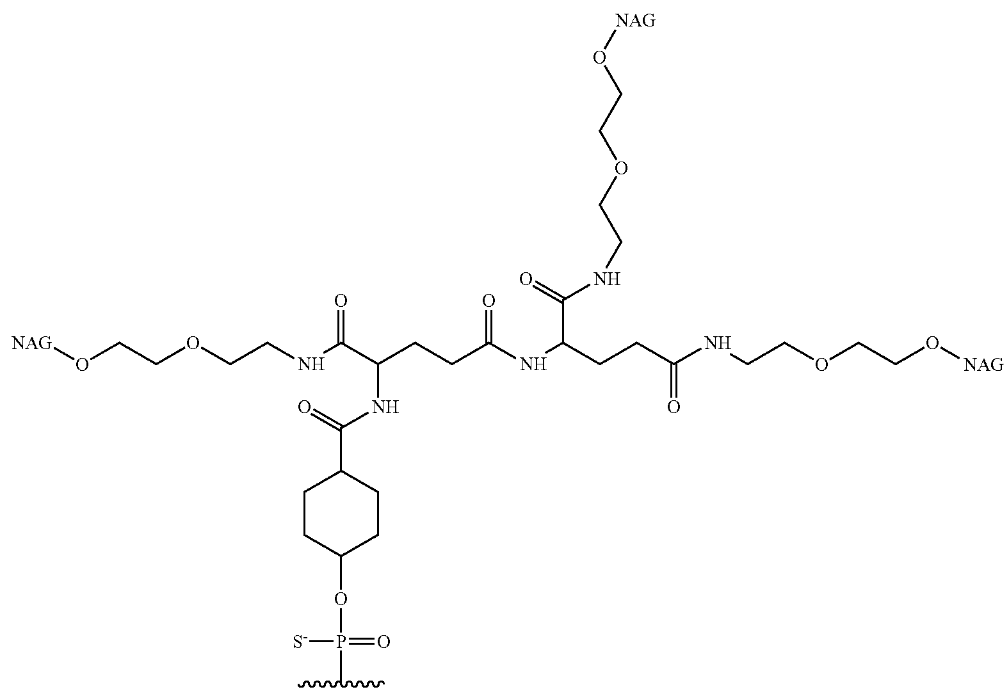
(NAG29)s TABLE 2-continued
| Structures Representing Various Modified Nucleotides, Targeting Groups, And Linking Groups |
|---|
| 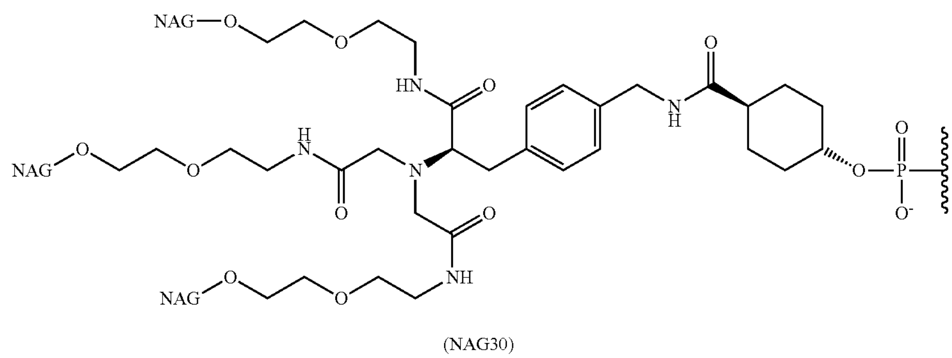 |
| (NAG30) |
| 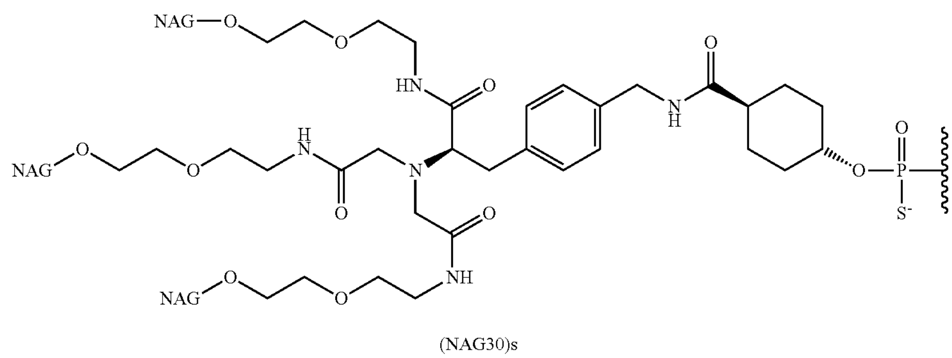 |
| (NAG30)s |
| 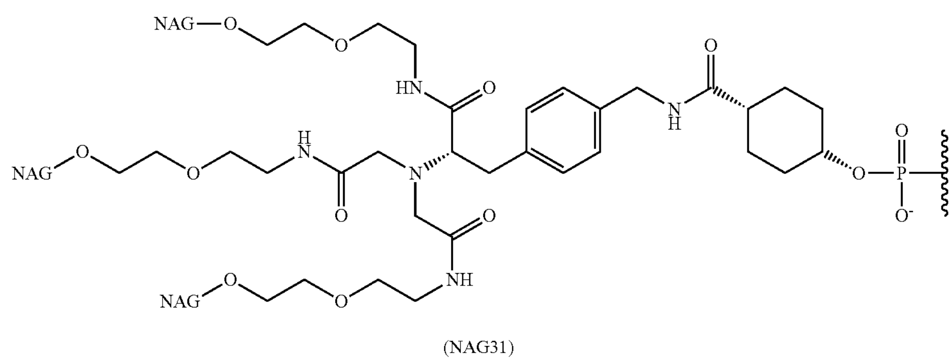 |
| (NAG31) |
| 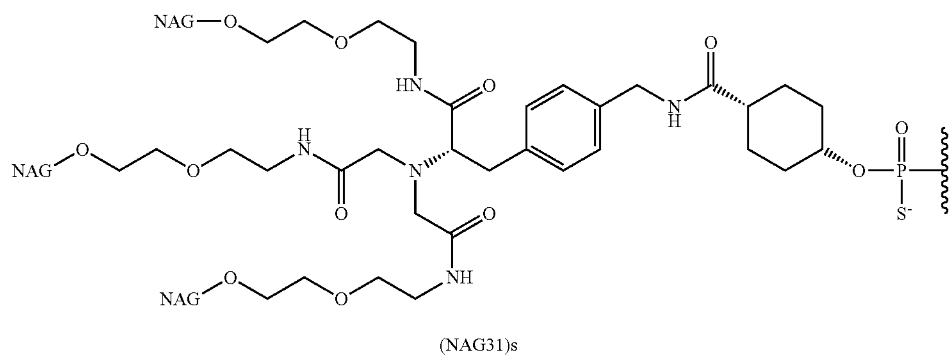 |
| (NAG31)s |

TABLE 2-continued
Structures Representing Various Modified Nucleotides, Targeting Groups, And Linking Groups
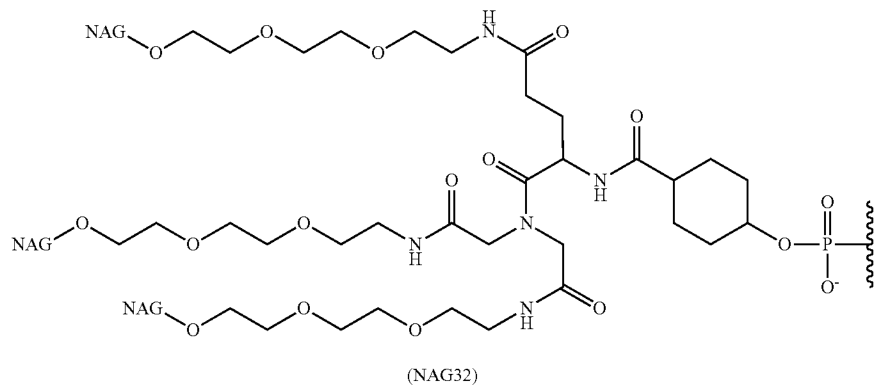
(NAG32)
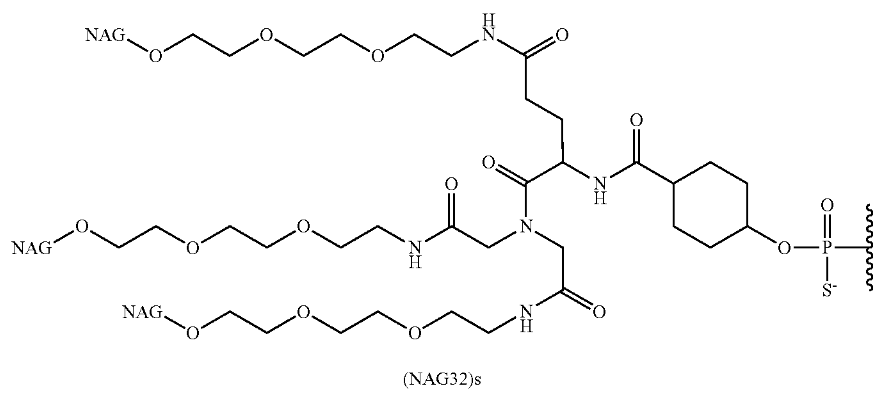
(NAG32)s
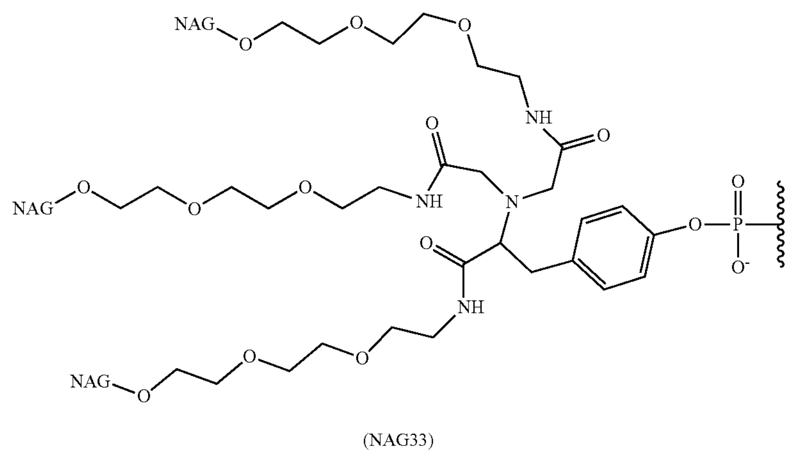
(NAG33)

TABLE 2-continued
| Structures Representing Various Modified Nucleotides, Targeting Groups, And Linking Groups |
|---|
| 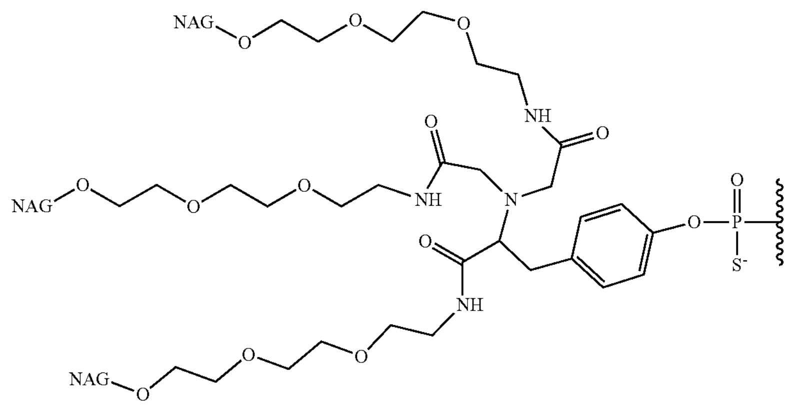<br>(NAG33)s |
| 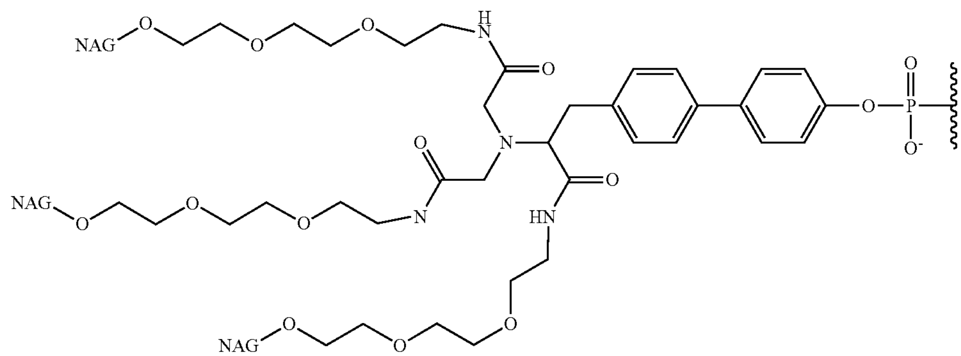<br>(NAG34) |
| 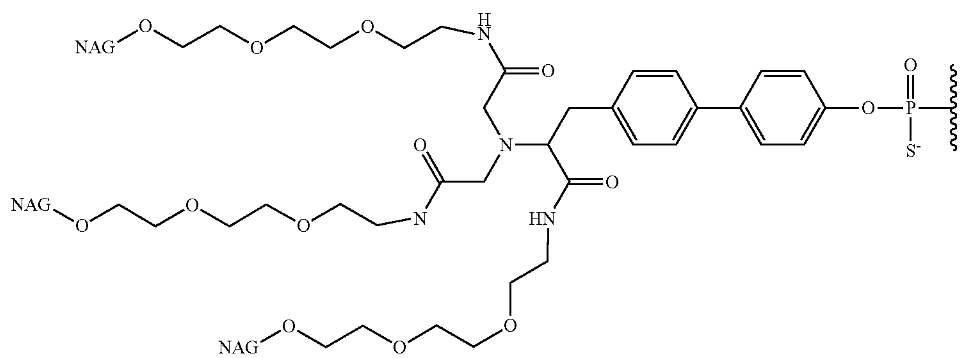<br>(NAG34)s |

TABLE 2-continued
Structures Representing Various Modified Nucleotides, Targeting Groups, And Linking Groups
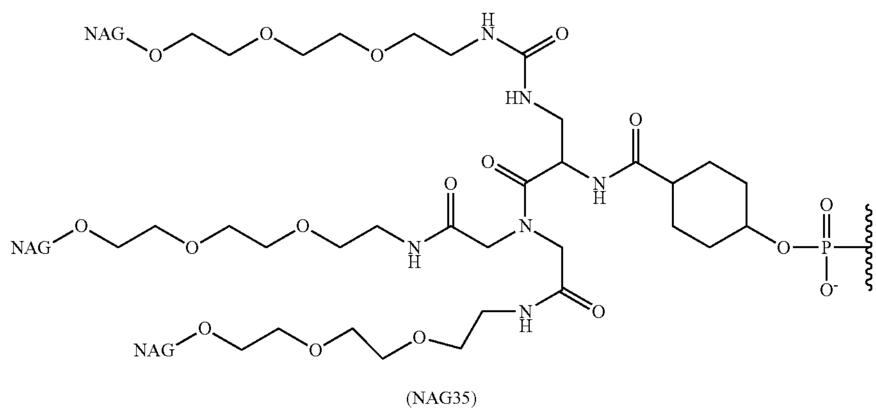
(NAG35)
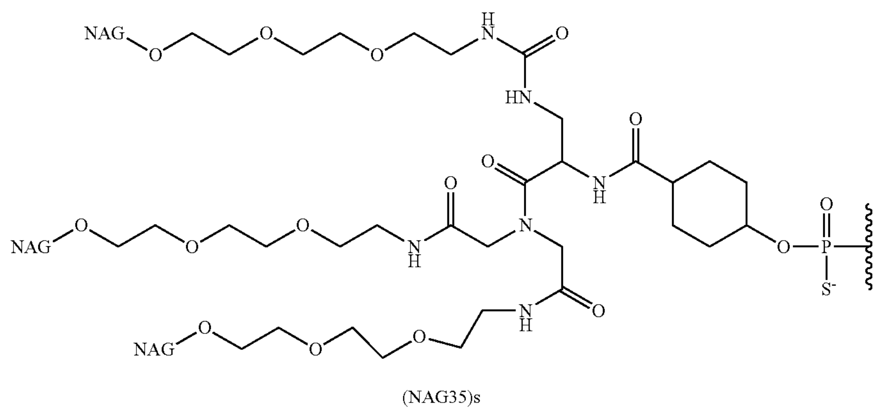
(NAG35)s
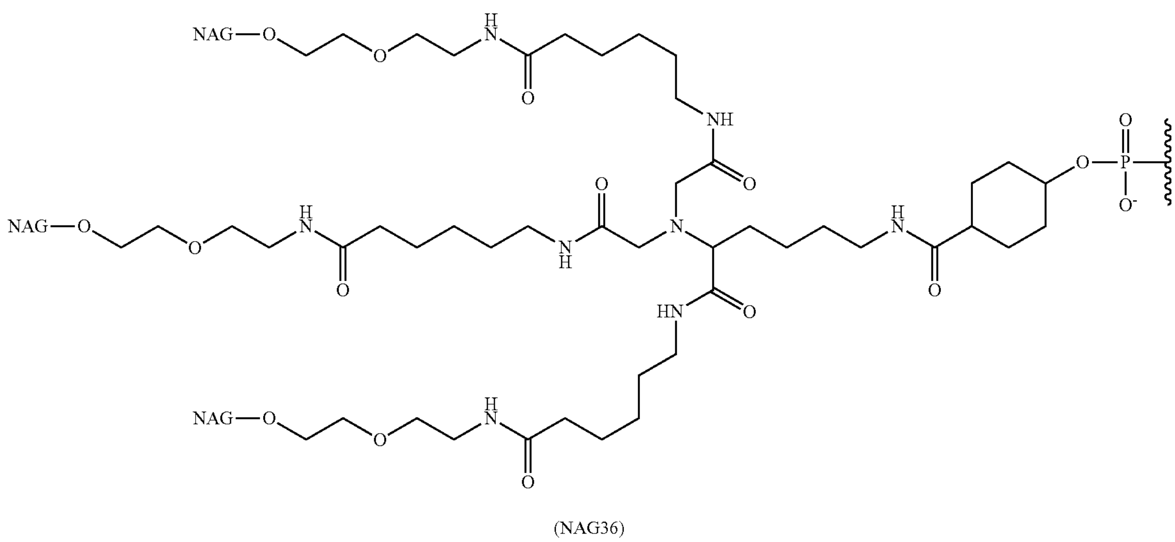
(NAG36)

TABLE 2-continued
Structures Representing Various Modified Nucleotides, Targeting Groups, And Linking Groups
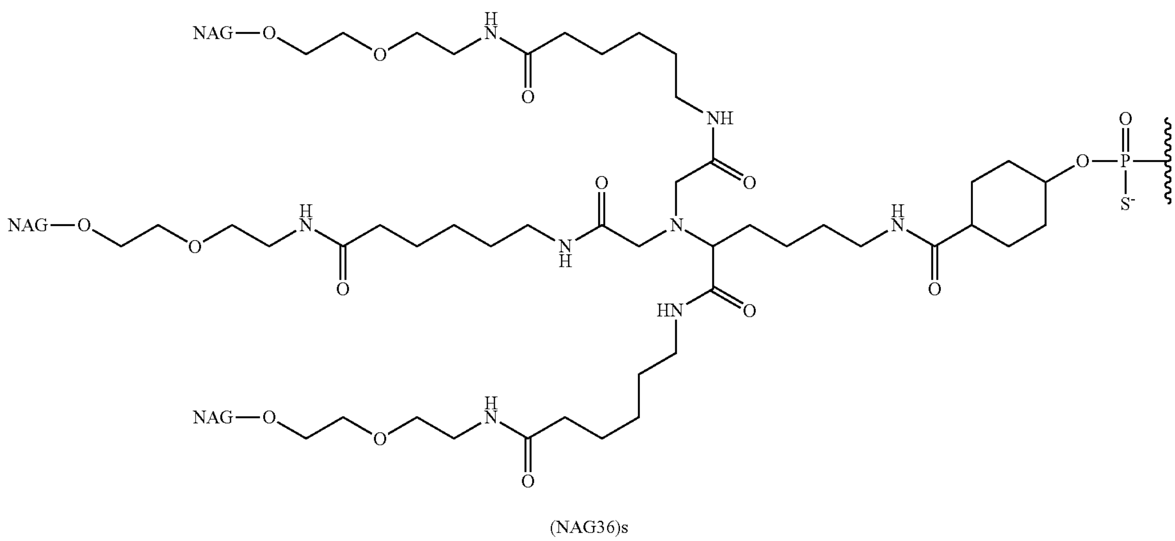
(NAG36)s
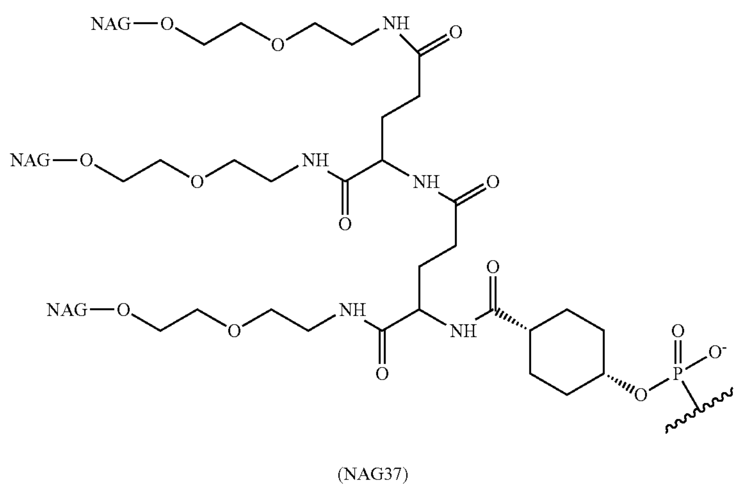
(NAG37)
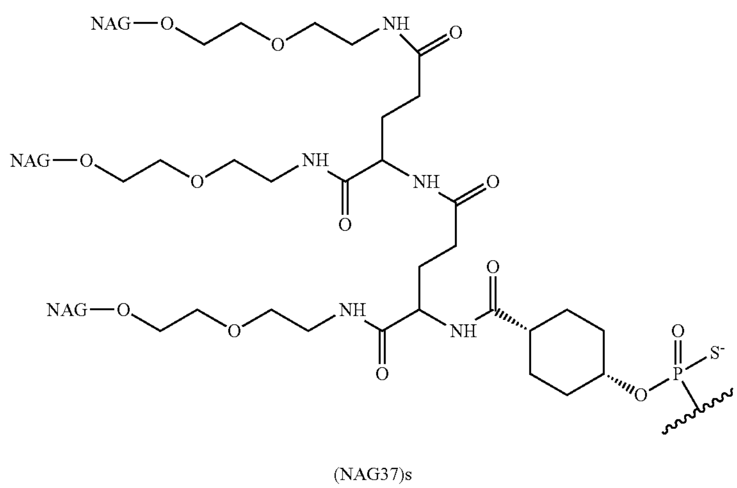
(NAG37)s TABLE 2-continued
Structures Representing Various Modified Nucleotides, Targeting Groups, And Linking Groups
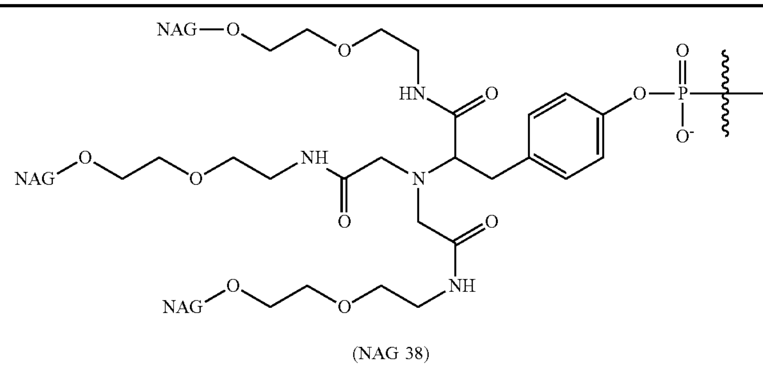
(NAG 38)
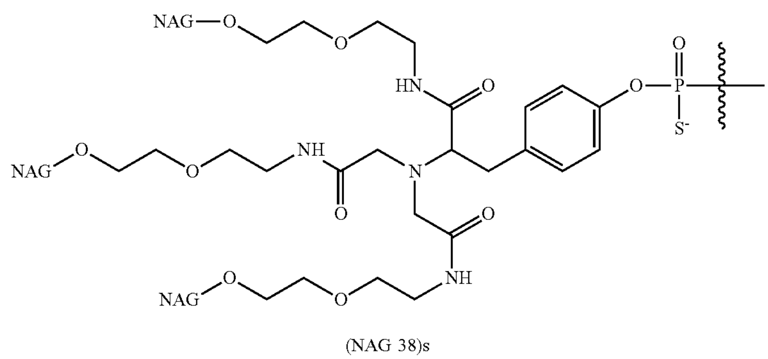
(NAG 38)s
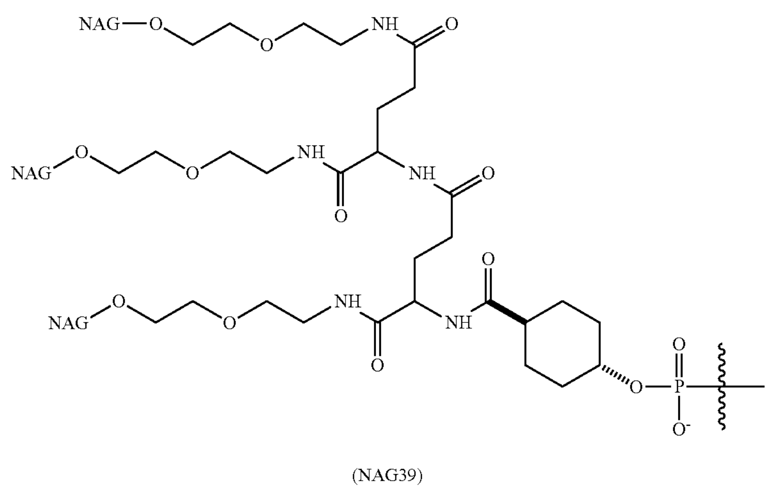
(NAG39)

TABLE 2-continued

Structures Representing Various Modified Nucleotides, Targeting Groups, And Linking Groups

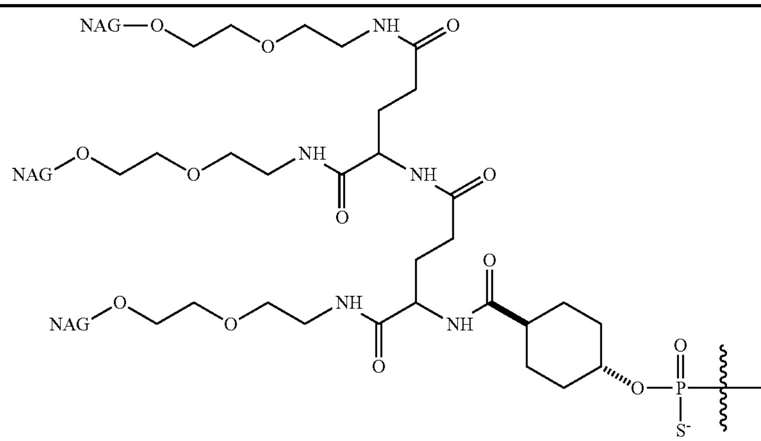

(NAG39)s

Modified Nucleotides

In some embodiments, the first or the second RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn, invAb), non-natural base-comprising nucleotides, bridged nucleotides, peptide nucleic acids (PNAs), 2',3'-seco nucleotide mimics (unlocked nucleobase analogues, represented herein as NUNA or NUNA), locked nucleotides (represented herein as NLNA or NLNA), 3'-O-methoxy (2' internucleoside linked) nucleotides (represented herein as 3'-OMen), 2'-F-Arabino nucleotides (represented herein as NfANA or NfANA), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification can be incorporated in the first or second RNAi agent or even in a single nucleotide thereof. The RNAi agent sense strands and antisense strands may be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or at least 90% of the nucleotides of the first or the second RNAi agent are modified nucleotides. As used herein, an RNAi agent wherein at least 90% of the nucleotides present are modified nucleotides is an RNAi agent having four or fewer (i.e., 0, 1, 2, 3, or 4) nucleotides in both the sense strand and the antisense strand being ribonucleotides. As used herein, a sense strand, wherein at least 90% of the nucleotides present are modified nucleotides, is a sense strand having two or fewer (i.e., 0, 1, or 2) nucleotides in the sense strand being ribonucleotides. As used herein, an antisense sense strand, wherein at least 90% of the nucleotides present are modified nucleotides, is an antisense strand having two or fewer (i.e., 0, 1, or 2) nucleotides in the sense strand being ribonucleotides. In some embodiments, one or more nucleotides of an RNAi agent is a ribonucleotide.

Modified Internucleoside Linkages

In some embodiments, one or more nucleotides of the first or the second RNAi agent are linked by non-standard linkages or backbones (i.e., modified internucleoside linkages or modified backbones). In some embodiments, a modified internucleoside linkage is a non-phosphate-containing covalent internucleoside linkage. Modified internucleoside linkages or backbones include, but are not limited to, 5'-phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of the first or the second RNAi agent can contain 1, 2, 3, 4, 5, or 6 phosphorothioate linkages, an antisense strand of the first or the second RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of the first or the second RNAi agent can contain 1, 2, 3, or 4 phosphorothioate linkages, an antisense strand of the first or the second RNAi agent can contain 1, 2, 3, or 4 phosphorothioate linkages, or both the sense strand and the antisense strand independently can contain 1, 2, 3, or 4 phosphorothioate linkages.

In some embodiments, the first or the second RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, the first or the second RNAi agent antisense strand contains four phosphorothioate internucleoside linkages. In some embodiments, the four phosphorothioate internucleoside linkages are between the nucleotides at positions 1-3 from the 5' end of the sense strand and between the nucleotides at positions 19-21, 20-22, 21-23, 22-24, 23-25, or 24-26 from the 5' end. In some embodiments, the first or the second RNAi agent contains at least two phosphorothioate internucleoside linkages in the sense strand and three or four phosphorothioate internucleoside linkages in the antisense strand.

In some embodiments, the first or the second RNAi agent contains one or more modified nucleotides and one or more modified internucleoside linkages. In some embodiments, a 2'-modified nucleoside is combined with modified internucleoside linkage. In some embodiments, the first and the second RNAi agents disclosed herein comprise any of the modified sequences in Table 3.

TABLE 3

Exemplary modified sequences for first and second RNAi agents

| Antisense | | Sense | |
|---|---|---|---|
| SEQ ID NO | Unmodified sequence (5' → 3') | SEQ ID NO | Sense Unmodified sequence (5' → 3') |
| 1 | asGfsasAfaAfuugagAfgAfaGfuCfcAfsc | 10 | (NAG25)sgsuggacuuCfUfCfucaauuuucus(invAb) |
| 1 | asGfsasAfaAfuugagAfgAfaGfuCfcAfsc | 11 | (NAG37)s(invAb)sguggacuuCfUfCfucaauuuucus(invAb) |
| 1 | asGfsasAfaAfuugagAfgAfaGfuCfcAfsc | 13 | (NAG25)s(invAb)sguggacuuCfUfCfucaauuuucus(invAb) |
| 2 | asGfsasAfaAfuUfgAfgAfgAfaGfuCfcasc | 10 | (NAG25)sgsuggacuuCfUfCfucaauuuucus(invAb) |
| 2 | asGfsasAfaAfuUfgAfgAfgAfaGfuCfcasc | 11 | (NAG37)s(invAb)sguggacuuCfUfCfucaauuuucus(invAb) |
| 2 | asGfsasAfaAfuUfgAfgAfgAfaGfuCfcasc | 13 | (NAG25)s(invAb)sguggacuuCfUfCfucaauuuucus(invAb) |
| 3 | asGfsasAfaAfuUfgAfgAfgAfaGfuCfcacusu | 10 | (NAG25)sgsuggacuuCfUfCfucaauuuucus(invAb) |
| 3 | asGfsasAfaAfuUfgAfgAfgAfaGfuCfcacusu | 11 | (NAG37)s(invAb)sguggacuuCfUfCfucaauuuucus(invAb) |
| 3 | asGfsasAfaAfuUfgAfgAfgAfaGfuCfcacusu | 13 | (NAG25)s(invAb)sguggacuuCfUfCfucaauuuucus(invAb) |
| 4 | asGfsasAfaAfuUfgAfgAfgAfaGfuCfcacsc | 12 | (NAG37)s(invAb)sgguggacuuCfUfCfucaauuuucus(invAb) |
| 8 | usAfscsCfaAfuUfuAfuGfcCfuAfcAfgcsg | 16 | (NAG37)s(invAb)scgcuguagGfCfAfuaaauugguas(invAb) |
| 8 | usAfscsCfaAfuUfuAfuGfcCfuAfcAfgcsg | 17 | (NAG37)csgcuguagGfCfAfuaaauugguas(invAb) |
| 8 | usAfscsCfaAfuUfuAfuGfcCfuAfcAfgcsg | 18 | (NAG25)s(invAb)scgcuguagGfCfAfuaaauugguas(invAb) |

A=adenosine-3'-phosphate;
C=cytidine-3'-phosphate;
G=guanosine-3'-phosphate;
U=uridine-3'-phosphate
n=any 2'-OMe modified nucleotide
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Nf=any 2'-fluoro modified nucleotide
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dT=2'-deoxythymidine-3'-phosphate
$N_{UNA}$=2',3'-seco nucleotide mimics (unlocked nucleobase analogs)
$N_{LNA}$=locked nucleotide
$Nf_{ANA}$=2'-F-Arabino nucleotide
NM=2'-methoxyethyl nucleotide
AM=2'-methoxyethyladenosine-3'-phosphate
AMs=2'-methoxyethyladenosine-3'-phosphorothioate
TM=2'-methoxyethylthymidine-3'-phosphate
TMs=2'-methoxyethylthymidine-3'-phosphorothioate
R=ribitol
(invdN)=any inverted deoxyribonucleotide (3'-3' linked nucleotide)
(invAb)=inverted (3'-3' linked) abasic deoxyribonucleotide, see Table 6
(invAb)s=inverted (3'-3' linked) abasic deoxyribonucleotide-5'-phosphorothioate, see Table 6
(invn)=any inverted 2'-OMe nucleotide (3'-3' linked nucleotide)
s=phosphorothioate linkage In some embodiments, the first RNAi agent comprises SEQ ID NO: 5 and SEQ ID NO: 14. In some embodiments, the first RNAi agent comprises SEQ ID NO: 6 and SEQ ID NO: 14. In some embodiments, the first RNAi agent comprises SEQ ID NO: 7 and SEQ ID NO: 15. In some embodiments, the first RNAi agent comprises SEQ ID NO: 1 and SEQ ID NO: 10, 11 or 13. In some embodiments, the first RNAi agent comprises SEQ ID NO: 2 and SEQ ID NO: 10, 11 or 13. In some embodiments, the first RNAi agent comprises SEQ ID NO: 3 and SEQ ID NO: 10, 11, or 13. In some embodiments, the first RNAi agent comprises SEQ ID NO: 4 and SEQ ID NO: 12. In some embodiments, the second RNAi agent comprises SEQ ID NO: 9 and SEQ ID NO: 19. In some embodiments, the second RNAi agent comprises SEQ ID NO: 8 and SEQ ID NO: 16, 17 or 18.

In some embodiments, the RNAi component comprises a first RNAi agent comprising SEQ ID NO: 5 and SEQ ID NO: 14 and a second RNAi agent comprising SEQ ID NO: 9 and SEQ ID NO: 19. In some embodiments, the RNAi component comprises a first RNAi agent comprising SEQ ID NO: 6 and SEQ ID NO: 14 and a second RNAi agent comprising SEQ ID NO: 9 and SEQ ID NO: 19. In some embodiments, the RNAi component comprises a first RNAi agent comprising SEQ ID NO: 7 and SEQ ID NO: 15 and a second RNAi agent comprising SEQ ID NO: 9 and SEQ ID NO: 19.

In some embodiments, the RNAi component comprises a first RNAi agent comprising SEQ ID NO: 1 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 2 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 3 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 4 and SEQ ID NO: 12 and a second RNAi agent comprising SEQ ID NO: 8 and SEQ ID NO: 16, 17 or 18.

In some embodiments, the RNAi component comprises a first and a second RNAi agent in a ratio of about 1:1, 2:1, 3:1, 4:1 or 5:1. In some embodiments, the two HBV RNAi agents are administered in a ratio of about 2:1.

In some embodiments, the first and the second RNAi agents are each independently conjugated to (NAG37)s, the first RNAi agent comprises an antisense strand comprising SEQ ID NO: 2 and a sense strand comprising SEQ ID NO: 11, the second RNAi agent comprises an antisense strand comprising SEQ ID NO: 8 and a sense strand comprising SEQ ID NO: 16.

Anti-Hepatitis B Virus (HBV) Agents

In some embodiments, the effective amount of the RNAi component is used in combination with an effective amount of at least one anti-HBV agent, more particularly an effective amount of at least one anti-HBV compound, more particularly at least one anti-HBV agent or compound other than the RNAi component of the application, more particularly other than an anti-HBV siRNA, more particularly at least one anti-HBV agent or compound selected from among Direct Acting Antivirals (such as nucleos(t)ide analogs, more particularly tenofovir disoproxil fumarate, tenofovir alafenamide, entecavir, lamivudine, telbivudine, any combination of at least two of these nucleos(t)ide analogs), cytokines (such as interferon, more particularly interferon alpha, interferon lambda, pegylated interferon, pegylated interferon alpha), HBV DNA polymerase inhibitors; Immunomodulators; Toll-like receptor modulators (e.g., Toll-like receptor 7 modulators; Toll-like receptor 8 modulators; Toll-like receptor 3 modulators; Toll like receptor 9 modulators); Interferon alpha receptor ligands; Hyaluronidase inhibitors; Modulators of IL-10; HBsAg inhibitors; Cyclophilin inhibitors; HBV Prophylactic vaccines; HBV Therapeutic vaccines; HBV viral entry inhibitors; Endonuclease modulators; Inhibitors of ribonucleotide reductase; Hepatitis B virus E antigen inhibitors; HBV antibodies targeting the surface antigens of the hepatitis B virus; HBV antibodies; CCR2 chemokine antagonists; Thymosin agonists; Cytokines, such as IL12; Capsid Assembly Modulators, Nucleoprotein inhibitors (HBV core or capsid protein inhibitors); Nucleic Acid Polymers (NAPs); Stimulators of retinoic acid-inducible gene 1; Stimulators of NOD2; Hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, CTLA-4 inhibitors; Agonists of co-stimulatory receptors that are expressed on immune cells (more particularly T cells), such as CD27 and CD28; BTK inhibitors; Other drugs for treating HBV; IDO inhibitors; Arginase inhibitors; and KDM5 inhibitors, more particularly selected from among Direct Acting Antivirals (such as nucleos(t)ide analogs), cytokines (such an interferon), immune modulators, vaccines, Capsid Assembly Modulators (CAMs), Toll-Like Receptors modulators (e.g., TLR7/TLR8/TLR9 modulators), more particularly selected from among nucleos(t)ide analogs and interferon, more particularly selected from among tenofovir disoproxil fumarate, tenofovir alafenamide, entecavir, lamivudine, telbivudine, any combination of at least two of these nucleos(t)ide analogs, interferon alpha, interferon lambda, pegylated interferon, pegylated interferon alpha.

Interferon

Human interferons are classified into three major types based on the type of receptor through which they signal. In various embodiments, an interferon of any of Types I-III is used in combination with an RNAi component to treat an HDV infection. All type I IFNs bind to a specific cell surface receptor complex known as the IFN-alpha receptor (IFNAR) that consists of IFNAR1 and IFNAR2 chains. The type I interferons present in humans are IFN-alpha, IFN-beta, IFN-epsilon, and IFN-omega. Type II IFNs bind to IFN-gamma receptor (IFNGR) that consists of IFNGR1 and IFNGR2 chains. The type II interferon in humans is IFN-gamma. The recently classified type III interferon group consists of three IFN-lambda molecules called IFN-lambda1, IFN-lambda2 and IFN-lambda3 (also called IL29, IL28A, and IL28B, respectively). These IFNs signal through a receptor complex consisting of IL10R2 (also called CRF2-4) and IFNLR1 (also called CRF2-12).

In one aspect, the present invention provides combination therapies in which an interferon-alpha or interferon-lambda are used in combination with an RNAi component, and optionally a nucleos(t)ide analog (NUC). The term "interferon-alpha" or "IFN-a" and "interferon-lambda" or "IFN-λ" as used herein refers to a family of related polypeptides that inhibit viral replication and cellular proliferation and modulate immune response. Suitable interferons for purposes of the invention include, but are not limited to, pegylated IFN-a-2a, pegylated IFN-a-2b, consensus IFN, IFN-λ (e.g., IFN-λI, such as IFN-Xla), or pegylated IFN-λ (e.g., pegylated IFN-λI such as pegylated IFN-Xla).

Interferon Alpha

The term "IFN-a" includes naturally occurring IFN-a; synthetic IFN-a; derivatized IFN-a (e.g., PEGylated IFN-a, glycosylated IFN-a, and the like); and analogs of naturally occurring or synthetic IFN-a. The term "IFN-a" also encompasses consensus IFN-a. Thus, essentially any IFN-a or IFN-λ that has antiviral properties, as described for naturally occurring IFN-a, can be used in the combination therapies of the invention.

The term "IFN-a" encompasses derivatives of IFN-a that are derivatized (e.g., are chemically modified relative to the naturally occurring peptide) to alter certain properties such as serum half-life. As such, the term "IFN-a" includes IFN-a derivatized with polyethylene glycol ("PEGylated IFN-a"), and the like. PEGylated IFN-a, and methods for making same, is discussed in, e.g., U.S. Pat. Nos. 5,382,657; 5,951,974; and 5,981,709. PEGylated IFN-a encompasses conjugates of PEG and any of the above-described IFN-a molecules, including, but not limited to, PEG conjugated to interferon alpha-2a (Roferon, Hoffman La-Roche, Nutley, N.J.), interferon alpha-2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, CA.). Thus, in some embodiments of the combination therapies of the invention, the IFN-a has been modified with one or more polyethylene glycol moieties, i.e., pegylated. Two forms of pegylated-interferon, peginterferon alfa-2a (40 kD) (Pegasys®, Genentech) and peginterferon alfa-2b (12 kD) (Peglntron®, Merck), are commercially available, which differ in terms of their pharmacokinetic, viral kinetic, tolerability profiles, and hence, dosing.

Peginterferon alfa-2a (Pegasys®) consists of interferon alfa-2a (~20 kD) covalently linked to a 40 kD branched polyethylene glycol (PEG). The PEG moiety is linked at a single site to the interferon alfa moiety via a stable amide bond to lysine. Peginterferon alfa-2a has an approximate molecular weight of 60,000 daltons. The biologic activity of peginterferon-alfa-2a derives from its interferon alfa-2a moiety which impacts both adaptive and innate immune responses against certain viruses. This alpha interferon binds to and activates human type 1 interferon receptors on hepatocytes, which activates multiple intracellular signal transduction pathways, culminating in the expression of interferon-stimulated genes that produce an array of antiviral effects, such as blocking viral protein synthesis and inducing viral RNA mutagenesis. Compared with the native interferon alfa-2a, the peginterferon alfa-2a has sustained absorption, delayed clear. Peginterferon alfa-2a is used as a fixed weekly dose. Peginterferon alfa-2a has a relatively constant absorption after injection and is distributed mostly in the blood and organs.

Peginterferon alfa-2b (Peglntron®) consists of interferon alfa-2b covalently linked to a 12 kD linear polyethylene glycol (PEG). The average molecular weight of the molecule is approximately 31,300 daltons. Peginterferon alfa-2b is predominantly composed of monopegylated species (one PEG molecule is attached to one interferon molecule), with only a small amount of dipegylated species. Fourteen different PEG attachment sites on the interferon molecule have been identified. The biologic activity of peginterferon alfa-2b derives from its interferon alfa-2b moiety, which impacts both adaptive and innate immune responses against certain viruses. This alpha interferon binds to and activates human type 1 interferon receptors on hepatocytes, which activates multiple intracellular signal transduction pathways, culminating in the expression of interferon-stimulated genes that produce an array of antiviral effects, such as blocking viral protein synthesis and inducing viral RNA mutagenesis. Compared with the native interferon alfa-2b, the peginterferon alfa-2b has sustained absorption, delayed clearance, and a prolonged half-life. Peginterferon alfa-2b is used as a weekly dose based on the weight of the patient. Peginterferon alfa-2b has a rapid absorption and a wider distribution in the body.

The PEG molecule of a pegylated IFN-a polypeptide is conjugated to one or more amino acid side chains of the IFN-a polypeptide. In an embodiment, the pegylated IFN-a contains a PEG moiety on only one amino acid. In another embodiment, the pegylated IFN-a contains a PEG moiety on two or more amino acids, e.g., the IFN-a contains a PEG moiety attached to two, three, four, five, six, seven, eight, nine, ten, eleven, twelve, thirteen, or fourteen different amino acid residues. IFN-a may be coupled directly to PEG (i.e., without a linking group) through an amino group, a sulfhydryl group, a hydroxyl group, or a carboxyl group.

The term "IFN-a" also encompasses consensus IFN-a. Consensus IFN-a (also referred to as "CIFN" and "IFN-con" and "consensus interferon") encompasses, but is not limited to, the amino acid sequences designated IFN-con1, IFN-con2 and IFN-con3 which are disclosed in U.S. Pat. Nos. 4,695,623 and 4,897,471; and consensus interferon as defined by determination of a consensus sequence of naturally occurring interferon alphas (e.g., Infergen®, Three Rivers Pharmaceuticals, Warrendale, PA). IFN-con1 is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, at least one additional therapeutic agent is CIFN.

In various embodiments of the combination therapies of the invention, fusion polypeptides comprising an IFN-a and a heterologous polypeptide are used. Suitable IFN-a fusion polypeptides include, but are not limited to, Albuferon-alpha™ (a fusion product of human albumin and IFN-a; Human Genome Sciences; see, e.g., Osborn et al., 2002, J. Pharmacol. Exp. Therap. 303:540-548). Also suitable for use in the present methods are gene-shuffled forms of IFN-a.

See, e.g., Masci et al., 2003, Curr. Oncol. Rep. 5:108-113. Other suitable interferons include Multiferon (Viragen), Medusa Interferon (Flamel Technology), Locteron (Octopus), and Omega Interferon (Intarcia/Boehringer Ingelheim).

Interferon Lambda

The term "IFN-λ" encompasses IFN-lambda-1 (which includes IFN-lambda-la), IFN-lambda-2, and IFN-lambda-3. These proteins are also known as interleukin-29 (IL-29), IL-28A, and IL-28B, respectively. Collectively, these 3 cytokines comprise the type III subset of IFNs. They are distinct from both type I and type II IFNs for a number of reasons, including the fact that they signal through a heterodimeric receptor complex that is different from the receptors used by type I or type II IFNs. Although type I IFNs (IFN-alpha/beta) and type III IFNs (IFN-lambda) signal via distinct receptor complexes, they activate the same intracellular signaling pathway and many of the same biological activities, including antiviral activity, in a wide variety of target cells. Interferon lambda may be administered at any therapeutically appropriate dose, including, without limitation, 80, 120 or 180 mcg QW. In some embodiments, the dose for an adult human is 120 micrograms once per week.

In some embodiments, the interferon lambda is a pegylated form of interferon lambda (e.g., pegylated interferon lambda-1 or pegylated interferon lambda-1a). In some embodiments, the interferon lambda is an interferon disclosed in U.S. Pat. No. 7,157,559 incorporated by reference herein.

While not wishing to be bound by theories, it is believed that an interferon, such as an interferon alpha or an interferon lambda, induces interferon-stimulated genes (ISGs), and/or stimulates immune response, more particularly of the Th1 response, such as expression or activation of the TBET transcription factor is increased, and/or the production of IFNgamma by CD4+ T cells is increased (e.g. ratio IFN-gamma/IL4 is superior to 1). The administration of interferon therefore enhances the therapeutic effects of the RNAi component and/or the nucleos(t)ide analog (NUC) according to the embodiments of the invention.

Anti-Hepatitis D Virus (HDV) Agents

In some embodiments, the effective amount of the RNAi component is used in combination with an effective amount of at least one anti-HDV agent, more particularly an effective amount of at least one anti-HDV compound, more particularly an effective amount of at least one anti-HDV agent or compound other than the RNAi component of the application, more particularly an effective amount of an HDV entry inhibitor (e.g., Myrrcludex (bulevirtide)) and/or an effective amount of a farnesyl transferase inhibitor (e.g., Lonafarnib).

In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component. In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component, and is stopped once the administration of the RNAi component starts.

The combinations described herein can be used in any methods or kits described below.

Composition

Also provided herein is pharmaceutical composition for use in the treatment of a Hepatitis D Virus infection in a subject in need thereof, preferably a human subject in need thereof, wherein the pharmaceutical composition comprises an effective amount of an RNAi component, wherein the RNAi component comprises:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is formulated for administration to the subject via intravenous or subcutaneous injection. In certain embodiments, the RNAi component is formulated for administration once monthly (or Q4W), once every two months (or Q8W), or once every three months (or Q12W), more particularly once monthly. In certain embodiments, the RNAi component is administered in a dose of about 40-200 mg, more particularly 100 mg, 150 mg, or 200 mg, more particularly 100 mg.

In some embodiments, the treatment further comprises administering an effective amount of at least one anti-HBV agent or compound, more particularly at least one anti-HBV agent or compound other than the RNAi component of the application, more particularly other than an anti-HBV siRNA, more particularly at least one anti-HBV agent selected from among Direct Acting Antivirals (such as nucleos(t)ide analogs, more particularly tenofovir disoproxil fumarate, tenofovir alafenamide, entecavir, lamivudine, telbivudine, any combination of at least two of these nucleos(t)ide analogs), cytokines (such as interferon, more particularly interferon alpha, interferon lambda, pegylated interferon, pegylated interferon alpha), HBV DNA polymerase inhibitors; Immunomodulators; Toll-like receptor modulators (e.g., Toll-like receptor 7 modulators; Toll-like receptor 8 modulators; Toll-like receptor 3 modulators; Toll like receptor 9 modulators); Interferon alpha receptor ligands; Hyaluronidase inhibitors; Modulators of IL-10; HBsAg inhibitors; Cyclophilin inhibitors; HBV Prophylactic vaccines; HBV Therapeutic vaccines; HBV viral entry inhibitors; Endonuclease modulators; Inhibitors of ribonucleotide reductase; Hepatitis B virus E antigen inhibitors; HBV antibodies targeting the surface antigens of the hepatitis B virus; HBV antibodies; CCR2 chemokine antagonists; Thymosin agonists; Cytokines, such as IL12; Capsid Assembly Modulators, Nucleoprotein inhibitors (HBV core or capsid protein inhibitors); Nucleic Acid Polymers (NAPs); Stimulators of retinoic acid-inducible gene 1; Stimulators of NOD2; Hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, CTLA-4 inhibitors; Agonists of co-stimulatory receptors that are expressed on immune cells (more particularly T cells), such as CD27 and CD28; BTK inhibitors; Other drugs for treating HBV; IDO inhibitors; Arginase inhibitors; and KDM5 inhibitors, more particularly selected from among Direct Acting Antivirals (such as nucleos(t)ide analogs), cytokines (such an interferon), immune modulators, vaccines, Capsid Assembly Modulators (CAMs), Toll-Like Receptors modulators (e.g., TLR7/TLR8/TLR9 modulators), more particularly selected from among nucleos(t)ide analogs and interferon, more particularly selected from among tenofovir disoproxil fumarate, tenofovir alafenamide, entecavir, lamivudine, telbivudine, any combination of at least two of these nucleos(t)ide analogs, interferon alpha, interferon lambda, pegylated interferon, pegylated interferon alpha.

In some embodiments, the treatment further comprises administering an effective amount of at least one anti-HDV agent or compound, more particularly an effective amount of at least one other anti-HDV agent or compound other than the RNAi component of the application, more particularly an effective amount of an HDV entry inhibitor (e.g., Myrrcludex (bulevirtide)) and/or an effective amount of a farnesyl transferase inhibitor (e.g., Lonafarnib). In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component. In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component, and is stopped once the administration of the RNAi component starts.

Also provided herein is a composition comprising an RNAi component and a nucleos(t)ide analog (NUC) or IFN, wherein (a) the RNAi component comprises
  (i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and
  (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19.

RNAi Agent Pharmaceutical Compositions

In another aspect, described herein are methods for therapeutic and/or prophylactic treatment of a Hepatitis D Virus (HDV) infection in a subject in need thereof, preferably a human subject in need thereof, comprising administering a pharmaceutical composition comprising one or more RNAi agents that can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

In another aspect, methods described herein comprise one or more RNAi agents, wherein the one or more RNAi agents are prepared as pharmaceutical compositions or formulations. In some embodiments, pharmaceutical compositions include at least one RNAi agent. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering an RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions including an RNAi agent, thereby forming a pharmaceutical formulation suitable for in vivo delivery to a human.

The pharmaceutical compositions that include an RNAi agent and methods disclosed herein may decrease the level of the target mRNA in a cell, group of cells, group of cells, tissue, or subject, including: administering to the subject a therapeutically effective amount of a herein described RNAi agent, thereby inhibiting the expression of a target mRNA in the subject.

In some embodiments, the described pharmaceutical compositions including an RNAi agent are used for treating or managing clinical presentations associated with HDV infection, e.g., an HDV/HBV co-infection. In some embodiments, a therapeutically or prophylactically effective amount of one or more of pharmaceutical compositions is administered to a subject in need of such treatment, prevention or management. In some embodiments, administration of any of the disclosed RNAi agents can be used to decrease the number, severity, and/or frequency of symptoms of a disease in a subject.

The described pharmaceutical compositions including a RNAi agent can be used to treat at least one symptom in a subject having a disease or disorder that would benefit from reduction or inhibition in expression of the target mRNA. In some embodiments, the subject is administered a therapeutically effective amount of one or more pharmaceutical compositions including a RNAi agent thereby treating the symptom. In other embodiments, the subject is administered a prophylactically effective amount of one or more RNAi agents, thereby preventing the at least one symptom.

The route of administration is the path by which a RNAi agent is brought into contact with the body. In general, methods of administering drugs and nucleic acids for treatment of a mammal are well known in the art and can be applied to administration of the compositions described herein. The RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, there herein described pharmaceutical compositions via subcutaneous injection.

In certain embodiments, the RNAi component is contained in a syringe, for example a glass syringe, and wherein the syringe is optionally suitable for self-administration of the RNAi component by the patient or for administration of the RNAi component to the patient by an untrained personnel.

In certain embodiments, the syringe is suitable for self-administration of the RNAi component by the patient, and wherein the syringe is placed in an ergonomic shell or grip to stabilize the syringe for self-injection by the patient, or is provided in an autoinjector device.

The pharmaceutical compositions including a RNAi agent described herein can be delivered to a cell, group of cells, tumor, tissue, or subject using oligonucleotide delivery technologies known in the art. In general, any suitable method recognized in the art for delivering a nucleic acid molecule (in vitro or in vivo) can be adapted for use with a composition described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable carriers, pharmaceutically acceptable diluents, pharmaceutically acceptable excipients, or a combination of any of the foregoing. In some embodiments, the pharmaceutical compositions described herein can be formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical ingredient (API, therapeutic product, e.g., the RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active compound will be in the range of 25-400 mg per 1-18 weeks or 1-6 months. In some embodiments, an effective amount of an active compound will be in the range of 40-250 mg per 4 weeks (Q4W) or per one month (Q1M) or per two months (Q2M) or per three months (Q3M). The terms "Q4W" and "Q1M," "per 4 weeks" and "per one month," and variations thereof, can be used interchangeably throughout this application. The terms "Q8W" and "Q2M," "per 8 weeks" and "every two month," and variations thereof, can be used interchangeably throughout this application. The terms "Q12W" and "Q3M," "per 12 weeks" and "every three month," and variations thereof, can be used interchangeably throughout this application. In some embodiments, an effective amount of an active ingredient will be in the range of from about 0.5 to about 3 mg/kg of body weight per dose. In some embodiments, an effective amount of an active ingredient will be in the range of from about 25-400 mg per dose. In some embodiments, an effective amount of an active ingredient will be in the range of from about 50-125 mg per dose. In some embodiments, an effective amount of an active ingredient will be about 100 mg, about 150 mg, or about 200 mg per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

In some embodiments, an effective amount of the RNAi component is in the range of about 25-600 mg per dose. In some embodiments, an effective amount of the RNAi component is in the range of about 25-50 mg, about 50-75 mg, about 75-100 mg, about 100-150 mg, about 150-200 mg, about 200-250 mg, about 250-300 mg, about 300-400 mg, about 400-500 mg or about 500-600 mg per dose. In some embodiments, an effective amount of the RNAi component is about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg or about 600 mg per dose. In some embodiments, an effective amount of the RNAi component is about 25 mg, about 35 mg, about 40 mg, about 50 mg, about 100 mg, about 150 mg, or about 200 mg per dose.

The one or more (e.g., at least two) RNAi agents described herein can be formulated into one single composition or separate individual compositions. In some embodiments, the RNAi agents in separate individual compositions can be formulated with the same or different excipients and carriers. In some embodiments, the RNAi agents in separate individual compositions agents can be administered through same or different administration routes. In some embodiments, the RNAi agents are administered subcutaneously.

For treatment of disease or for formation of a medicament or composition for treatment of a disease, the pharmaceutical compositions described herein including an RNAi agent can be combined with an excipient or with a second therapeutic agent or treatment including, but not limited to: a second or other RNAi agent, an anti-HBV agent, an anti-HDV agent, a small molecule drug, an antibody, an antibody fragment, and/or a vaccine.

The described RNAi agents, when added to pharmaceutically acceptable excipients or adjuvants, can be packaged into kits, containers, packs, or dispensers. The pharmaceutical compositions described herein may be packaged in pre-filled syringes or vials.

In some embodiments, the composition comprises an effective amount of an RNAi component in the range of about 25-600 mg and an effective amount of a nucleos(t)ide analog (NUC) in the range of about 0.1-600 mg per dose. In some embodiments, the composition comprises an effective amount of an RNAi component in the range of about 40-200 mg and an effective amount of a nucleos(t)ide analog (NUC) in the range of about 0.1-600 mg per dose. In some embodiments, the composition comprises an effective amount of an RNAi of about 25 mg, about 35 mg, about 40 mg, about 50 mg, about 100 mg, about 150 mg, or about 200 mg and an effective amount of a nucleos(t)ide analog (NUC) of about 0.1 mg, about 5.0 mg, about 50 mg, about 100 mg, about 150 mg, about 300 mg, or about 600 mg per dose.

Interferon Pharmaceutical Composition

Any suitable pharmaceutical compositions of interferon, including those known in the art and/or described herein, can be used in the combination therapy of the application. The composition can be administered in the range of about 25-500 mcg per dose, more particularly 25-360 mcg per dose.

Kit

Provided herein is a kit comprising an effective amount of an RNAi component and an effective amount of at least one anti-HBV agent and/or at least one anti-HDV agent.

In some embodiments, the kit comprises an effective amount of an RNAi component and an effective amount of at least one anti-HBV agent or compound, more particularly at least one anti-HBV agent or compound other than the RNAi component of the application, more particularly other than an anti-HBV siRNA, more particularly at least one anti-HBV agent selected from among Direct Acting Antivirals (such as nucleos(t)ide analogs, more particularly tenofovir disoproxil fumarate, tenofovir alafenamide, entecavir, lamivudine, telbivudine, any combination of at least two of these nucleos(t)ide analogs), cytokines (such as interferon, more particularly interferon alpha, interferon lambda, pegylated interferon, pegylated interferon alpha), HBV DNA polymerase inhibitors; Immunomodulators; Toll-like receptor modulators (e.g., Toll-like receptor 7 modulators; Toll-like receptor 8 modulators; Toll-like receptor 3 modulators; Toll like receptor 9 modulators); Interferon alpha receptor ligands; Hyaluronidase inhibitors; Modulators of IL-10; HBsAg inhibitors; Cyclophilin inhibitors; HBV Prophylactic vaccines; HBV Therapeutic vaccines; HBV viral entry inhibitors; Endonuclease modulators; Inhibitors of ribonucleotide reductase; Hepatitis B virus E antigen inhibitors; HBV antibodies targeting the surface antigens of the hepatitis B virus; HBV antibodies; CCR2 chemokine antagonists; Thymosin agonists; Cytokines, such as IL12; Capsid Assembly Modulators, Nucleoprotein inhibitors (HBV core or capsid protein inhibitors); Nucleic Acid Polymers (NAPs); Stimulators of retinoic acid-inducible gene 1; Stimulators of NOD2; Hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, CTLA-4 inhibitors; Agonists of co-stimulatory receptors that are expressed on immune cells (more particularly T cells), such as CD27 and CD28; BTK inhibitors; Other drugs for treating HBV; IDO inhibitors; Arginase inhibitors; and KDM5 inhibitors, more particularly selected from among Direct Acting Antivirals (such as nucleos(t)ide analogs), cytokines (such an interferon), immune modulators, vaccines, Capsid Assembly Modulators (CAMs), Toll-Like Receptors modulators (e.g., TLR7/TLR8/TLR9 modulators), more particularly selected from among nucleos(t)ide analogs and interferon, more particularly selected from among tenofovir disoproxil fumarate, tenofovir alafenamide, entecavir, lamivudine, telbivudine, any combination of at least two of these nucleos (t)ide analogs, interferon alpha, interferon lambda, pegylated interferon, pegylated interferon alpha.

In some embodiments, the kit comprises an effective amount of an RNAi component and an effective amount of at least one anti-HDV agent or compound, more particularly an effective amount of at least one anti-HDV agent or compound other than the RNAi component of the application, more particularly an effective amount of an HDV entry inhibitor (e.g., Myrrcludex (bulevirtide)) and/or an effective amount of a farnesyl transferase inhibitor (e.g., Lonafarnib). In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component. In some embodiments, the at least one other anti-HDV agent (e.g., an HDV entry inhibitor (e.g., Myrrcludex (bulevirtide)) and/or a farnesyl transferase inhibitor (e.g., Lonafarnib)) is administered prior to the RNAi component, and is stopped once the administration of the RNAi component starts.

In another aspect, the kit further comprises a package insert including, without limitation, appropriate instructions for preparation and administration of the formulation, side effects of the formulation, and any other relevant information. The instructions can be in any suitable format, including, but not limited to, printed matter, videotape, computer readable disk, optical disc or directions to internet-based instructions.

In another aspect, kits for treating an individual who suffers from or is susceptible to the conditions described herein are provided, comprising a first container comprising a dosage amount of a composition or formulation as disclosed herein, and a package insert for use. The container can be any of those known in the art and appropriate for storage and delivery of intravenous formulation. In certain embodiments, the kit further comprises a second container comprising a pharmaceutically acceptable carrier, diluent, adjuvant, etc. for preparation of the formulation to be administered to the individual.

In some embodiments, the kit comprises one or more doses of the RNAi component in the range of about 25-600 mg per dose. In some embodiments, the kit comprises one or more doses of the RNAi component in the range of about 25-50 mg, about 50-75 mg, about 75-100 mg, about 100-150 mg, about 150-200 mg, about 200-250 mg, about 250-300 mg, about 300-400 mg, about 400-500 mg or about 500-600 mg per dose. In some embodiments, the kit comprises one or more doses of the RNAi component of about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg or about 600 mg per dose. In some embodiments, the kit comprises one or more doses of the RNAi component of about 25 mg, about 35 mg, about 40 mg, about 50 mg, about 100 mg, about 150 mg, or about 200 mg per dose.

In some embodiments, the kit comprises one or more doses of the nucleos(t)ide analog (NUC) in the range of about 0.1-600 mg. In some embodiments, the nucleos(t)ide analog (NUC) is entecavir, and the one or more doses are provided in a range of about 0.1-5 mg, about 0.1-4 mg, about 0.1-3 mg, about 0.1-2 mg, about 0.1-1 mg, about 0.5-5 mg, about 0.5-4 mg, about 0.5-3 mg, about 0.5-2 mg, about 1-5 mg, about 1-4 mg, about 1-3 mg, about 1-2 mg, about 2.5-5 mg, about 2.5-4 mg, or about 2.5-3 mg. In some embodiments, the nucleos(t)ide analog (NUC) is tenofovir alafenamide, and the one or more doses are provided in a range of about 5-50 mg, about 5-40 mg, about 5-30 mg, about 5-20 mg, about 5-10 mg, about 10-50 mg, about 10-40 mg, about 10-30 mg, about 10-20 mg, about 15-50 mg, about 15-40 mg, about 15-30 mg, about 20-50 mg, about 20-40 mg, about 20-30 mg, about 25-50 mg, about 25-40 mg, about 30-50 mg, or about 30-40 mg. In some embodiments, the nucleos (t)ide analog (NUC) is tenofovir disoproxil, and the one or more doses are provided in a range of about 200-500 mg, about 200-400 mg, about 200-300 mg, about 300-500 mg, or about 300-400 mg. In some embodiments, the nucleos(t)ide analog (NUC) is lamivudine, and the one or more doses are provided at about 100 mg, about 150 mg, or about 300 mg. In some embodiments, the nucleos(t)ide analog (NUC) is telbivudine, and the one or more doses are provided at about 600 mg.

In some embodiments, the kit comprises one or more doses of the interferon in the range of about 10-25 mcg, about 25-100 mcg, about 50-100 mcg, about 100-150 mcg, about 150-200 mcg, about 200-250 mcg, about 250-300 mcg, about 300-400 mcg, or about 400-500 mcg, per dose. In some embodiments, the kit comprises one or more doses of pegylated IFN lambda-1a, pegylated interferon alfa-2a or pegylated IFN lambda-1a, of about 75 mcg, about 80 mcg, about 85 mcg, about 90 mcg, about 95 mcg, about 100 mcg, about 125 mcg, about 150 mcg, about 175 mcg, about 200 mcg, about 250 mcg, about 300 mcg per dose.

In some embodiments, the kit contains an RNAi component useful for the invention, such as those described herein, for administration once monthly (or every four weeks (Q4W)), once every two months (or every eight weeks (Q8W)), or once every three months (or every twelve weeks (Q12W)) to a subject in a dose of about 40-250 mg, more particularly 40-200 mg, more particularly 100 mg, 150 mg, or 200 mg; more particularly 100 mg; and a nucleos(t)ide analog (NUC), such as those described herein, for administration to a subject in a daily dose of about 0.1-600 mg, about 0.1-5 mg, about 5-50 mg, about 200-500 mg, about 100 mg, about 150 mg, about 300 mg, or about 600 mg, more particularly a daily dose of entecavir of about 0.1-5 mg, a daily dose of about 5-50 mg of tenofovir alafenamide, a daily dose of about 200-500 mg of tenofovir disoproxil, a daily dose of about 100 mg, about 150 mg, or about 300 mg of lamivudine, or a daily dose of about 600 mg of telbivudine.

In some embodiments, the kit further comprises instructions for using the RNAi component and the nucleos(t)ide analog (NUC) or IFN contained therein for administration to treat a subject with an HDV infection, in particular, a subject having a HDV/HBV co-infection. In some embodiments, the kit further comprises instructions for using the RNAi component and the nucleos(t)ide analog (NUC) or IFN contained therein for administration to a subject with compensated cirrhosis.

In another aspect, kits may also be provided that contain sufficient dosages of the compositions described herein (including pharmaceutical compositions thereof) to provide effective treatment for an individual for an extended period, such as 1-3 days, 1-5 days, a week, 2 weeks, 3, weeks, 4 weeks, 6 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 2 years, 3 years, 4 years, 5 years, 6 years, 7 years, 8 years, 9 years, 10 years, 1 cycle, 2 cycles, 3 cycles, 4 cycles, 5 cycles, 6 cycles, 7 cycles, 8 cycles or more. In some embodiments, one cycle of treatment is about 1-24 months, about 1-3 months, about 3-6 months, about 6-9 months, about 9-12 months, about 12-18 months, about 18-21 months or about 21-24 months. In some embodiments, one cycle of treatment is about 1 month, about 2 months, about 3 months, about 4 months, about 5 months, about 6 months, about 7 months, about 8 months, about 9 months, about 10 months, about 11 months, about 12 months, about 15 months, about 18 months, about 21 months or about 24 months.

In some embodiments, the kits can also include multiple doses and may be packaged in quantities sufficient for storage and use in pharmacies, for example, hospital pharmacies and compounding pharmacies. In certain embodiments the kits may include a dosage amount of at least one composition as disclosed herein.

Method

Also provided herein is a method for treating a Hepatitis D Virus (HDV) infection in a subject in need thereof, preferably a human subject in need thereof, wherein the method comprises administering to the subject an effective amount of an RNAi component and at least one anti-HBV agent (other than the RNAi component, e.g., nucleos(t)ide analog (NUC), IFN) and/or at least one anti-HDV agent (other than the RNAi component, e.g., Myrrcludex or Lonafarnib), more particularly an effective amount of at least one anti-HBV agent (other than the RNAi agent), wherein the anti-HBV agent is a nucleos(t)ide analog (NUC) or an IFN, such as those described herein.

In some embodiments, the nucleos(t)ide analog (NUC) or interferon is not administered prior to the RNAi component. In some embodiments, the RNAi component is administered prior to or concurrently with the nucleos(t)ide analog (NUC).

In some embodiments, the HDV infection is a HDV/HBV co-infection. In some embodiments, the subject further comprises cirrhosis, more particularly compensated cirrhosis. In some embodiments, the subject is a patient without cirrhosis.

In some embodiments, the effective amount of the pharmaceutical composition comprising the RNAi component and the effective amount of the pharmaceutical composition comprising the nucleos(t)ide analog (NUC) or IFN is administered to the subject at least until the subject meets at least one of, at least two of, at least three of, at least four of, or the five following features: (i) a serum HDV RNA level with an at least a 2 log decrease or an undetectable level of serum HDV RNA; (ii) a serum ALT concentration of 40 U/L or lower if the subject is a male subject or of 30 U/L or lower if the subject is a female subject, or a relative reduction (from baseline) of serum ALT concentration by at least 40%, more particularly by at least 50%; (iii) a HBeAg-negative serum, (iv) a serum HBsAg level of 100 IU/mL or lower, more particularly of 10 IU/mL or lower, more particularly HBsAg seroclearance; and (v) HBs seroconversion. In some embodiments, the at least one of, at least two of, at least three of, at least four of, or five of features (i), (ii), (iii), (iv), and (v) are still met six (6) months after the end of treatment.

In some embodiments, the effective amount of the pharmaceutical composition comprising the RNAi component and/or the effective amount of the pharmaceutical composition comprising the nucleos(t)ide analog (NUC) or IFN is administered to the subject at least until the subject meets at least one of, at least two of, at least three of, or four of the following features: (i) a serum HDV RNA level with an at least a 2 log decrease or an undetectable level of serum HDV RNA; (ii) a serum ALT concentration of 40 U/L or lower if the subject is a male subject or of 30 U/L or lower if the subject is a female subject, or a relative reduction (from baseline) of serum ALT concentration by at least 40%, more particularly by at least 50%; (iii) a HBeAg-negative serum; and (iv) a serum HBsAg level of 100 IU/mL or lower, more particularly of 10 IU/mL or lower, more particularly HBsAg seroclearance. In some embodiments, the at least one of, at least two of, at least three of, or four of features (i), (ii), (iii), and (iv) are still met six (6) months after the end of treatment.

In some embodiments, the method comprises administering the effective amount of the pharmaceutical composition comprising the RNAi component and/or the effective amount of the pharmaceutical composition comprising the nucleos(t)ide analog (NUC) or IFN at least until the a 2 log decrease of the serum HDV RNA level or at least until there is an undetectable level of serum HDV RNA in the subject. In some embodiments, the method comprises administering the effective amount of the pharmaceutical composition comprising the RNAi component at least until the serum HBsAg level of the subject decreases down to 100 IU/mL or lower, more particularly down to 10 IU/mL or lower, more particularly HBsAg seroclearance. In some embodiments, the administration of the effective amount of the pharmaceutical composition comprising the RNAi component is stopped after the HBsAg level of the subject is 100 IU/mL or lower, more particularly of 10 IU/mL or lower. Alternatively or complementarily, the administration of the effective amount of the pharmaceutical composition comprising the RNAi component is stopped after HDV RNA is suppressed, more particularly undetectable or below LLoQ.

In some embodiments, the pharmaceutical composition comprising the RNAi component is administered to the subject for 1 year (48 weeks) or for at least 1 year (at least 48 weeks), at least 2 years, at least 3 years, at least 4 years, at least 5 years, at least 6 years, at least 7 years, at least 8 years, at least 9 years, or at least 10 years.

In some embodiments, the administration of the pharmaceutical composition comprising the RNAi component is stopped after HBs seroconversion has been detected in the subject. In some embodiments, the administration of the nucleos(t)ide analog (NUC) or of the interferon is continued after stopping the administration of the effective amount of the RNAi component.

In some embodiments, the HDV treatment regimen can be a finite HDV treatment regimen (e.g., for 1, 2, 3, 4, 5, 6, 7, 8, 9, or 10 years) or a chronic suppressive HDV treatment regimen.

In some embodiments, the RNAi component comprises: (i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7, and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19.

In some embodiments, the first RNAi agent comprises SEQ ID NO: 5 and SEQ ID NO: 14. In some embodiments, the first RNAi agent comprises SEQ ID NO: 6 and SEQ ID NO: 14. In some embodiments, the first RNAi agent comprises SEQ ID NO: 7 and SEQ ID NO: 15. In some embodiments, the first RNAi agent comprises SEQ ID NO: 1 and SEQ ID NO: 10, 11 or 13. In some embodiments, the first RNAi agent comprises SEQ ID NO: 2 and SEQ ID NO: 10, 11 or 13. In some embodiments, the first RNAi agent comprises SEQ ID NO: 3 and SEQ ID NO: 10, 11, or 13. In some embodiments, the first RNAi agent comprises SEQ ID NO: 4 and SEQ ID NO: 12. In some embodiments, the second RNAi agent comprises SEQ ID NO: 9 and SEQ ID NO: 19. In some embodiments, the second RNAi agent comprises SEQ ID NO: 8 and SEQ ID NO: 16, 17 or 18.

In some embodiments, the RNAi component comprises a first RNAi agent comprising SEQ ID NO: 5 and SEQ ID NO: 14 and a second RNAi agent comprising SEQ ID NO: 9 and SEQ ID NO: 19. In some embodiments, the RNAi component comprises a first RNAi agent comprising SEQ ID NO: 6 and SEQ ID NO: 14 and a second RNAi agent comprising SEQ ID NO: 9 and SEQ ID NO: 19. In some embodiments, the RNAi component comprises a first RNAi agent comprising SEQ ID NO: 7 and SEQ ID NO: 15 and a second RNAi agent comprising SEQ ID NO: 9 and SEQ ID NO: 19.

In some embodiments, the RNAi component comprises a first RNAi agent comprising SEQ ID NO: 1 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 2 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 3 and SEQ ID NO: 10, 11 or 13 and a second RNAi agent comprising SEQ ID NO: 8 and SEQ ID NO: 16, 17 or 18. In some embodiments, the RNAi component comprises a first RNAi agent comprising SEQ ID NO: 4 and SEQ ID NO: 12 and a second RNAi agent comprising SEQ ID NO: 8 and SEQ ID NO: 16, 17 or 18.

In some embodiments, the RNAi component comprises a first RNAi agent comprising SEQ ID NO: 2 and SEQ ID NO: 11 and the second RNAi agent comprising SEQ ID NO: 16 and SEQ ID NO: 8.

In some embodiments, the two RNAi agents are administered in a ratio of about 1:1, 2:1, 3:1, 4:1 or 5:1. In some embodiments, the two RNAi agents are administered in a ratio of about 2:1.

In some embodiments, the two RNAi agents are administered in a combined amount of about 25-75 mg per dose administration and in the ratio of about 2:1, about 3:1, about 1:1, about 4:1, about 5:1 or about 1:2. In some embodiments, the two RNAi agents are administered in a combined amount of about 35-40 mg per dose administration and in the ratio of about 2:1, about 3:1, about 1:1, about 4:1, about 5:1 or about 1:2. In some embodiments, the two RNAi agents are administered in a combined amount of about 50-125 mg per dose administration and in the ratio of about 2:1, about 3:1, about 1:1, about 4:1, about 5:1 or about 1:2. In some embodiments, the two RNAi agents are administered in a combined amount of about 75-150 mg per dose administration and in the ratio of about 2:1, about 3:1, about 1:1, about 4:1, about 5:1 or about 1:2. In some embodiments, the two RNAi agents are administered in a combined amount of about 100-200 mg per dose administration and in the ratio of about 2:1, about 3:1, about 1:1, about 4:1, about 5:1 or about 1:2. In some embodiments, the two RNAi agents are administered in a combined amount of about 150-250 mg per dose administration and in the ratio of about 2:1, about 3:1, about 1:1, about 4:1, about 5:1 or about 1:2. In some embodiments, the two RNAi agents are administered in a combined amount of about 200-300 mg per dose administration and in the ratio of about 2:1, about 3:1, about 1:1, about 4:1, about 5:1 or about 1:2. In some embodiments, the two RNAi agents are administered in a combined amount of about 300-400 mg per dose administration and in the ratio of about 2:1, about 3:1, about 1:1, about 4:1, about 5:1 or about 1:2. In some embodiments, the two RNAi agents are administered in a combined amount of about 50-100 mg per dose administration and in the ratio of about 2:1, about 3:1, about 1:1, about 4:1, about 5:1 or about 1:2. In some embodiments, the two RNAi agents are administered in a combined amount of about 25-400 mg per dose administration and in the ratio of about 2:1. In some embodiments, the two RNAi agents are administered in a combined amount of about 25-75 mg per dose administration and in the ratio of about 2:1. In some embodiments, the two RNAi agents are administered in a combined amount of about 35-40 mg per dose administration and in the ratio of about 2:1. In some embodiments, the two RNAi agents are administered in a combined amount of about 50-125 mg per dose administration and in the ratio of about 2:1. In some embodiments, the two RNAi agents are administered in a combined amount of about 75-150 mg per dose administration and in the ratio of about 2:1. In some embodiments, the two RNAi agents are administered in a combined amount of about 100-200 mg per dose administration and in the ratio of about 2:1. In some embodiments, the two RNAi agents are administered in a combined amount of about 125-225 mg per dose administration and in the ratio of about 2:1. In some embodiments, the two RNAi agents are administered in a combined amount of about 150-250 mg per dose administration and in the ratio of about 2:1. In some embodiments, the two RNAi agents are administered in a combined amount of about 200-300 mg per dose administration and in the ratio of about 2:1. In some embodiments, the two RNAi agents are administered in a combined amount of about 300-400 mg per dose administration and in the ratio of about 2:1. In some embodiments, the two RNAi agents are administered in a combined amount of about 100 mg per dose administration and in the ratio of about 2:1. In some embodiments, the two RNAi agents are administered in a combined amount of about 25 mg per dose administration and in the ratio of about 2:1. In some embodiments, the two RNAi agents are administered in a combined amount of about 35 mg per dose administration and in the ratio of about 2:1. In some embodiments, the two RNAi agents are administered in a combined amount of about 40 mg per dose administration and in the ratio of about 2:1. In some embodiments, the two RNAi agents are administered in a combined amount of about 50 mg per dose administration and in the ratio of about 2:1. In some embodiments, the two RNAi agents are administered in a combined amount of about 75 mg per dose administration and in the ratio of about 2:1. In some embodiments, the two RNAi agents are administered in a combined amount of about 200 mg per dose administration and in the ratio of about 2:1.

In some embodiments, the first RNAi agent is administered in an amount of about 3-650 mg per dose administration, and the second RNAi agent is administered in an amount of about 2-325 mg per dose administration. In some embodiments, the first RNAi agent is administered in an amount of about 15-150 mg per dose administration, and the second RNAi agent is administered in an amount of about 5-75 mg per dose administration. In some embodiments, the first RNAi agent is administered in an amount of about 35-265 mg per dose administration. In some embodiments, the first RNAi agent is administered in an amount of about 50-75 mg per dose administration. In some embodiments, the first RNAi agent is administered in an amount of about 15-75 mg per dose administration. In some embodiments, the second RNAi agent is administered in an amount of about 20-125 mg per dose administration. In some embodiments, the second RNAi agent is administered in an amount of about 25-50 mg per dose administration. In some embodiments, the second RNAi agent is administered in an amount of about 5-40 mg per dose administration. In some embodiments, the first RNAi agent is administered in an amount of about 17 mg per dose administration, and the second RNAi agent is administered in an amount of about 8 mg per dose administration. In some embodiments, the first RNAi agent is administered in an amount of about 23 mg per dose administration, and the second RNAi agent is administered in an amount of about 12 mg per dose administration. In some embodiments, the first RNAi agent is administered in an amount of about 27 mg per dose administration, and the second RNAi agent is administered in an amount of about 13 mg per dose administration. In some embodiments, the first RNAi agent is administered in an amount of about 33 mg per dose administration, and the second RNAi agent is administered in an amount of about 17 mg per dose administration. In some embodiments, the first RNAi agent is administered in an amount of about 67 mg per dose administration, and the second RNAi agent is administered in an amount of about 33 mg per dose administration.

In some embodiments, two RNAi agents are administered at a combined dose of 25-400 mg per dose administration. In an embodiment, two RNAi agents are administered at a combined dose of 25-400 mg, and the first RNAi agent is administered with the second RNAi agent at a ratio of 1:1. In an embodiment, the dose of each of the first and second RNAi agents is in an amount of about 12 mg for a combined dose of about 25 mg. In an embodiment, the dose of each of the first and second RNAi agents is in an amount of about 17 mg for a combined dose of about 35 mg. In an embodiment, the dose of each of the first and second RNAi agents is in an amount of about 20 mg for a combined dose of about 40 mg. In an embodiment, the dose of each of the first and second RNAi agents is in an amount of about 25 mg for a combined dose of about 50 mg. In an embodiment, the dose of each of the first and second RNAi agents is in an amount of about 50 mg for a combined dose of about 100 mg. In an embodiment, the dose of each of the first and second RNAi agents is in an amount of about 100 mg for a combined dose of about 200 mg. In an embodiment, the dose of each of the first and second RNAi agents is in an amount of about 150 mg for a combined dose of about 300 mg. In an embodiment, the dose of each of the first and second RNAi agents is in an amount of about 200 mg for a combined dose of about 400 mg.

In an embodiment, two RNAi agents are administered at a combined dose of 25-400 mg per dose, and the first RNAi agent is administered with the second RNAi agent at a ratio of 2:1. In an embodiment, the dose of the first RNAi agent is in an amount of about 16 mg, and the dose of the second RNAi agent is in an amount of about 8 mg for a combined dose of about 25 mg. In an embodiment, the dose of the first RNAi agent is in an amount of about 24 mg, and the dose of the second RNAi agent is in an amount of about 12 mg for a combined dose of about 35 mg. In an embodiment, the dose of the first RNAi agent is in an amount of about 27 mg, and the dose of the second RNAi agent is in an amount of about 13 mg for a combined dose of about 40 mg. In an embodiment, the dose of the first RNAi agent is in an amount of about 33 mg, and the dose of the second RNAi agent is in an amount of about 17 mg for a combined dose of about 50 mg. In an embodiment, the dose of the first RNAi agent is in an amount of about 65 mg, and the dose of the second RNAi agent is in an amount of about 35 mg for a combined dose of about 100 mg. In an embodiment, the dose of the first RNAi agent is in an amount of about 133 mg, and the dose of the second RNAi agent is in an amount of about 67 mg for a combined dose of about 200 mg. In an embodiment, the dose of the first RNAi agent is in an amount of about 200 mg, and the dose of the second RNAi agent is in an amount of about 100 mg for a combined dose of about 300 mg. In an embodiment, the dose of the first RNAi agent is in an amount of about 270 mg, and the dose of the second RNAi agent is in an amount of about 135 mg for a combined dose of about 400 mg.

In an embodiment, two RNAi agents are administered at a combined dose of 25-400 mg per dose, the first RNAi agent is administered with the second RNAi agent at a ratio of 3:1. In an embodiment, the dose of the first RNAi agent is in an amount of about 18 mg, and the dose of the second RNAi agent is in an amount of about 6 mg for a combined dose of about 25 mg. In an embodiment, the dose of the first RNAi agent is in an amount of about 27 mg, and the dose of the second RNAi agent is in an amount of about 9 mg for a combined dose of about 35 mg. In an embodiment, the dose of the first RNAi agent is in an amount of about 30 mg, and the dose of the second RNAi agent is in an amount of about 10 mg for a combined dose of about 40 mg. In an embodiment, the dose of the first RNAi agent is in an amount of about 36 mg, and the dose of the second RNAi agent is in an amount of about 12 mg for a combined dose of about 50 mg. In an embodiment, the dose of the first RNAi agent is in an amount of about 75 mg, and the dose of the second RNAi agent is in an amount of about 25 mg for a combined dose of about 100 mg. In an embodiment, the dose of the first RNAi agent is in an amount of about 150 mg, and the dose of the second RNAi agent is in an amount of about 50 mg for a combined dose of about 200 mg. In an embodiment, the dose of the first RNAi agent is in an amount of about 225 mg, and the dose of the second RNAi agent is in an amount of about 75 mg for a combined dose of about 300 mg. In an embodiment, the dose of the first RNAi agent is in an amount of about 300 mg, and the dose of the second RNAi agent is in an amount of about 100 mg for a combined dose of about 400 mg.

In some embodiments, the first RNAi agent and the second RNAi agent are administered in a combined amount of about 25-400 mg per dose administration. In some embodiments, the first RNAi agent and the second RNAi agent are administered in a combined amount of about 25-50 mg, 50-75 mg, 75-100 mg, 100-125 mg, 125-150 mg, 150-175 mg, 175-200 mg, 200-225 mg, 225-250 mg, 250-275 mg, 275-300 mg, 300-325 mg, 325-350 mg, 350-375 mg, 375-400 mg, 25-75 mg, 50-100 mg, 100-150 mg, 150-200 mg, 200-250 mg, 250-300 mg, 300-350 mg, 350-400 mg, 25-100 mg, 50-150 mg, 100-200 mg, 150-250 mg, 200-300 mg, 300-400 mg, 25-200 mg, or 200-400 mg per dose administration. In some embodiments, the first RNAi agent to the second RNAi agent are administered in a combined amount of about 25 mg, about 50 mg, about 100 mg, about 125 mg, about 150 mg, about 175 mg, about 200 mg, about 225 mg, about 250 mg, about 275 mg, about 300 mg, about 325 mg, about 350 mg, about 375 mg, or about 400 mg per dose administration. In some embodiments, the first RNAi agent and the second RNAi agent are administered in a combined amount of about 50 mg, about 75 mg, about 100 mg, or about 125 mg per dose administration. In some embodiments, the first RNAi agent and the second RNAi agent are administered in a combined amount of about 25 mg, about 35 mg, about 40 mg, or about 200 mg per dose administration.

In some embodiments, the two RNAi agents are administered in a combined amount of about 1-10 mg/kg per dose administration. In some embodiments, the two RNAi agents are administered in a combined amount of about 1-5 mg/kg per dose administration. In some embodiments, the two RNAi agents are administered in a combined amount of about 1-1.5 mg/kg, about 1.5-2.0 mg/kg, about 2.0-2.5 mg/kg, about 2.5-3.0 mg/kg, about 3.0-3.5 mg/kg, about 3.5-4.0 mg/kg, about 4.0-4.5 mg/kg, about 4.5-5.0 mg/kg, about 5.0-5.5 mg/kg, about 5.5-6.0 mg/kg, about 6.0-6.5 mg/kg, about 6.5-7.0 mg/kg, about 7.0-7.5 mg/kg, about 7.5-8.0 mg/kg, about 8.0-8.5 mg/kg, about 8.5-9.0 mg/kg, about 9.0-9.5 mg/kg, about 9.5-10 mg/kg, about 1-2.5 mg/kg, about 2.5-5.0 mg/kg, about 5.0-7.5 mg/kg, about 7.5-10 mg/kg, about 1-5.0 mg/kg, or about 5.0-10 mg/kg per dose administration.

In some embodiments, the first RNAi agent is administered in an amount of about 0.6-7 mg/kg per dose administration, and the second RNAi agent is administered in an amount of about 0.3-5 mg/kg per dose administration. In some embodiments, the second RNAi agent is administered in an amount of about 0.5-2.5 mg/kg per dose administration. In some embodiments, the second RNAi agent is administered in an amount of about 0.3-1.5 mg/kg per dose administration. In some embodiments, the first RNAi agent is administered in an amount of about 0.6-5 mg/kg per dose administration. In some embodiments, the first RNAi agent is administered in an amount of about 1-2.5 mg/kg per dose administration.

In some embodiments, the first RNAi agent and the second RNAi agent are administered for a duration of about 1-12 months, about 2 years, about 3 years, about 4 years, about 5 years, about 6 years, about 7 years, about 8 years, about 9 years, or about 10 years. In some embodiments, the first RNAi agent and the second RNAi agent are administered for a duration of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 2 years, at least about 3 years, at least about 4 years, at least about 5 years, at least about 6 years, at least about 7 years, at least about 8 years, at least about 9 years, or at least about 10 years. In some embodiments, the first RNAi agent and the second RNAi agent are administered for a duration of about 1-18 weeks. In some embodiments, the first RNAi agent and the second RNAi agent are administered for a duration of at least about 1 week, at least about 5 weeks, at least about 10 weeks, at least about 15 weeks, at least about 20 weeks, at least about 25 weeks, at least about 30 weeks, at least about 35 weeks, at least about 40 weeks, at least about 45 weeks, at least about 50 weeks, at least about 55 weeks, at least about 60 weeks, at least about 65 weeks, at least about 70 weeks, at least about 75 weeks, at least about 80 weeks, at least about 90 weeks, or at least 96 weeks.

In some embodiments, the first RNAi agent and the second RNAi agent are administered at a combined dose of 25-400 mg per dose administration. In an embodiment, the first RNAi agent and the second RNAi agent are administered at a combined dose of 25-400 mg, and the first RNAi agent is administered with the second RNAi agent at a ratio of 1:1. In an embodiment, the dose of the first RNAi agent is administered with the second RNAi agent is in an amount of about 12 mg for a combined dose of about 25 mg. In an embodiment, the dose of each of the first RNAi agent and the second RNAi agent is in an amount of about 17 mg for a combined dose of about 35 mg. In an embodiment, the dose of each of the first RNAi agent and the second RNAi agent is in an amount of about 20 mg for a combined dose of about 40 mg. In an embodiment, the dose of each of the first RNAi agent and the second RNAi agent is in an amount of about 25 mg for a combined dose of about 50 mg. In an embodiment, the dose of each of the first RNAi agent and the second RNAi agent is in an amount of about 50 mg for a combined dose of about 100 mg. In an embodiment, the dose of each of the first RNAi agent and the second RNAi agent is in an amount of about 100 mg for a combined dose of about 200 mg. In an embodiment, the dose of each of the first RNAi agent and the second RNAi agent is in an amount of about 150 mg for a combined dose of about 300 mg. In an embodiment, the dose of each of the first RNAi agent and the second RNAi agent is in an amount of about 200 mg for a combined dose of about 400 mg.

In an embodiment, the first RNAi agent and the second RNAi agent are administered at a combined dose of 25-400 mg per dose, and the second RNAi agent is administered with the first RNAi agent at a ratio of 1:2. In an embodiment, the dose of the first RNAi agent is in an amount of about 16 mg, and the dose of the second RNAi agent is in an amount of about 8 mg for a combined dose of about 25 mg. In an embodiment, the dose of the second RNAi agent is in an amount of about 12 mg, and the dose of the first RNAi agent is in an amount of about 24 mg for a combined dose of about 35 mg. In an embodiment, the dose of the first RNAi agent is in an amount of about 27 mg, and the dose of the second RNAi agent is in an amount of about 13 mg for a combined dose of about 40 mg. In an embodiment, the dose of the first RNAi agent is in an amount of about 33 mg, and the dose of the second RNAi agent is in an amount of about 17 mg for a combined dose of about 50 mg. In an embodiment, the dose of the second RNAi agent is in an amount of about 35 mg, and the dose of the first RNAi agent is in an amount of about 65 mg for a combined dose of about 100 mg. In an embodiment, the dose of v is in an amount of about 67 mg, and the dose of the first RNAi agent is in an amount of about 133 mg for a combined dose of about 200 mg. In an embodiment, the dose of the second RNAi agent is in an amount of about 100 mg, and the dose of the first RNAi agent is in an amount of about 200 mg for a combined dose of about 300 mg. In an embodiment, the dose of the second RNAi agent is in an amount of about 135 mg, and the dose of the first RNAi agent is in an amount of about 270 mg for a combined dose of about 400 mg.

In an embodiment, the first RNAi agent and the second RNAi agent are administered at a combined dose of 25-400 mg per dose, the second RNAi agent is administered with the first RNAi agent at a ratio of 1:3. In an embodiment, the dose of the first RNAi agent is in an amount of about 18 mg, and the dose of the second RNAi agent is in an amount of about 6 mg for a combined dose of about 25 mg. In an embodiment, the dose of the second RNAi agent is in an amount of about 9 mg, and the dose of the first RNAi agent is in an amount of about 27 mg for a combined dose of about 35 mg. In an embodiment, the dose of the first RNAi agent is in an amount of about 30 mg, and the dose of the second RNAi agent is in an amount of about 10 mg for a combined dose of about 40 mg. In an embodiment, the dose of the first RNAi agent is in an amount of about 36 mg, and the dose of the second RNAi agent is in an amount of about 12 mg for a combined dose of about 50 mg. In an embodiment, the dose of the second RNAi agent is in an amount of about 25 mg, and the dose of the first RNAi agent is in an amount of about 75 mg for a combined dose of about 100 mg. In an embodiment, the dose of the second RNAi agent is in an amount of about 50 mg, and the dose of the first RNAi agent is in an amount of about 150 mg for a combined dose of about 200 mg. In an embodiment, the dose of the second RNAi agent is in an amount of about 75 mg, and the dose of the first RNAi agent is in an amount of about 225 mg for a combined dose of about 300 mg. In an embodiment, the dose of the second RNAi agent is in an amount of about 100 mg, and the dose of the first RNAi agent is in an amount of about 300 mg for a combined dose of about 400 mg.

In some embodiments, about 1 mg/kg (mpk) of the first RNAi agent and about 1 mg/kg of the second RNAi agent are administered to a subject in need thereof. In some embodiments, about 1.5 mg/kg of the first RNAi agent and about 1.5 mg/kg of the second RNAi agent are administered to a subject in need thereof. In some embodiments, about 2.0 mg/kg of the first RNAi agent and about 1.0 mg/kg of the second RNAi agent are administered to a subject in need thereof. In some embodiments, about 3.0 mg/kg of the first RNAi agent and about 1.0 mg/kg of the second RNAi agent are administered to a subject in need thereof. In some embodiments, about 3.2 mg/kg of the first RNAi agent and about 0.8 mg/kg of the second RNAi agent are administered to a subject in need thereof. In some embodiments, about 2.7 mg/kg of the first RNAi agent and about 1.3 mg/kg of the second RNAi agent are administered to a subject in need thereof. In some embodiments, about 4.0 mg/kg of the first RNAi agent and about 1.0 mg/kg of the second RNAi agent are administered to a subject in need thereof. In some embodiments, about 3.3 mg/kg of the first RNAi agent and about 1.7 mg/kg of the second RNAi agent are administered to a subject in need thereof. In some embodiments, between about 0.05 and about 5 mg/kg of the first RNAi agent and between about 0.05 and about 5 mg/kg of the second RNAi agent are administered to a subject in need thereof. In some embodiments, about the first RNAi agent and about the second RNAi agent are administered separately (e.g., in separate injections). In some embodiments, the respective dose of the first RNAi agent and the respective dose of the second RNAi agent are administered together (e.g., in the same injection). In some embodiments, the respective dose of the first RNAi agent and the respective dose of the second RNAi agent are prepared in a single pharmaceutical composition.

In some embodiments, the RNAi component is administered to the subject once monthly (or Q4W), once every two months (or Q8W), or once every three months (or Q12W) in a dose of about 40-200 mg, more particularly 100 mg, 150 mg, or 200 mg, more particularly 100 mg.

In some embodiments, the first and the second RNAi agents are each independently conjugated to (NAG37)s, the first RNAi agent comprises an antisense strand comprising SEQ ID NO: 2 and a sense strand comprising SEQ ID NO: 11, the second RNAi agent comprises an antisense strand comprising SEQ ID NO: 8 and a sense strand comprising SEQ ID NO: 16.

In some embodiments, the RNAi component is formulated in a solid form, such as a tablet or capsule. In some embodiments, the RNAi component is formulated for subcutaneous injection. In some embodiments, the RNAi component is formulated in a liquid form, such as suspensions, solutions, emulsions, or syrups, or may be lyophilized.

In some embodiments, the RNAi component and the nucleos(t)ide analog (NUC) or IFN are administered simultaneously or intermittently. In some embodiments, the RNAi component and the nucleos(t)ide analog (NUC) or IFN are administered and formulated separately and administered with different dosing frequencies. In some embodiments, the RNAi component and the nucleos(t)ide analog (NUC) or IFN are formulated as one or separate compositions. In some embodiments, the RNAi component is formulated as a solution and administered once per month or once every four weeks, once every two months, or once every three months via subcutaneous injection. In some embodiments, the nucleos(t)ide analog (NUC) is formulated for daily oral administration.

In some embodiments, the method further comprises administering a nucleos(t)ide analog (NUC). In some embodiments, the nucleoside analog is entecavir, tenofovir disoproxil fumarate, tenofovir alafenamide, lamivudine, telbivudine, or a combination thereof, more particularly entecavir, tenofovir disoproxil fumurate, tenofovir alafenamide, or a combination thereof. In some embodiments, the nucleoside analog is entecavir and it is administered in a daily dose in the amount of about 0.01-5 mg, about 0.01-0.05 mg, about 0.05-0.1 mg, about 0.1-0.5 mg, about 0.5-1 mg, about 1-2 mg, about 2-3 mg, about 3-4 mg or about 4-5 mg. In some embodiments, the nucleoside analog is entecavir and it is administered in a daily dose in the amount of about 0.5 mg. In some embodiments, the nucleoside analog is tenofovir disoproxil fumarate and it is administered in a daily dose in the amount of about 100-500 mg, about 100-150 mg, about 150-200 mg, about 200-250 mg, about 250-300 mg, 300-400 mg, about 400-500 mg. In some embodiments, the nucleoside analog is tenofovir disoproxil fumarate and it is administered in a daily dose in the amount of about 300 mg. In some embodiments, the nucleoside analog is tenofovir alafenamide and it is administered in a daily dose in the amount of about 5-100 mg, about 5-25 mg, about 25-50 mg, about 50-75 or about 75-100 mg. In some embodiments, the nucleoside analog is tenofovir alafenamide and it is administered in a daily dose in the amount of about 25 mg. In some embodiments, the nucleoside analog is lamivudine and it is administered in a daily dose in the amount of about 50-600 mg, about 50-300 mg, about 100-300 mg, about 100-500 mg, about 150-400 mg, about 200-350, or about 250-300 mg. In some embodiments, the nucleoside analog is lamivudine and it is administered in a daily dose in the amount of 100 mg, 150 mg, or 300 mg. In some embodiments, the nucleoside analog is telbivudine and it is administered in a daily dose in the amount of about 300-800 mg, about 400-700 mg, about 300-600 mg, about 300-400 mg, about 400-500 mg, or about 500-600 mg. In some embodiments, the nucleoside analog is telbivudine and it is administered in a daily dose in the amount of 600 mg. In some embodiments, the patients have been exposed to the nucleoside analog prior to the combination therapy. In some embodiments, the patients have been administered the nucleoside analog for at least 1 month, at least 3 months, at least 6 months, or at least 1 year prior to receiving the combination therapy.

In some embodiments, the interferon is pegylated IFN-alpha (e.g., pegylated IFN-alfa 2a or pegylated IFN-alfa 2b) or pegylated IFN-lambda, more particularly pegylated IFN-alfa 2a or pegylated IFN-alpha 2b. Suitable doses of IFN-alpha or IFN-lambda, more particularly of pegylated IFN-alfa (2a or 2b) or pegylated IFN-lambda, more particularly of pegylated IFN-alpha (2a or 2b), include, but are not limited to, 9-75 million Units per week, more particularly 15-35 million Units per week (e.g., 5-10 million Units thrice weekly, or 5 million Units QD, or 10 million Units thrice weekly), or 0.25-4.0 mcg/kg/week (e.g., 1.0-1.5 mcg/kg/week), or 25-360 mcg/QW or 25-360 mcg/BIW, or 25-360 QD (e.g., 100-200 mcg/kg/QW or BIW or QD, e.g., 120-180 mcg/kg/QW or BIW or QD).

In some embodiments, interferon alpha (e.g., Pegasys®, Genentech) is administered weekly. In some embodiments, the interferon alpha is administered at a dose of 120 mcg QW or 180 mcg QW. In some embodiments, pegylated interferon (Pegasys®) is administered at a dose of 180 micrograms per week.

In one embodiment of these combination therapies, pegylated interferon alfa-2a (Pegasys) is administered weekly in dosages of 180 microgram (mcg) or 120 mcg or 135 mcg (used for patients that react negatively to the higher dose) subcutaneously (SQ).

In another embodiment of these combination therapies, pegylated interferon alfa-2b (Peglntron) is administered weekly in dosages of 1.5 mcg/kg/wk SQ.

In other embodiments of these methods, alfa-interferons are used as follows: consensus interferon (Infergen) administered at 9 mcg to 15 mcg SQ daily or thrice weekly; interferon-alfa 2a recombinant administered at 3 Ml U to 9 Ml U SQ administered thrice weekly; interferon-alfa 2b (Intron A) recombinant administered 3 MIU to 25 MIU SQ administered thrice weekly; and pegylated interferon lambda (IL-28) administered at 80 mcg to 240 mcg SQ weekly.

In some embodiment, an interferon is administered to the subject by intravenous or subcutaneous injection in a dose of about 25-500 mcg, preferably 80-300 mcg, per week, preferably once per week, more particularly of 100-200 mcg per week, more particularly 180 mcg per week.

In some embodiments, the interferon is pegylated IFN lambda-1a. Suitable doses of pegylated IFN lambda-1a include, but are not limited to, 180 mcg QW; 120 mcg QW; 180 mcg/BIW; 120 mcg/BIW.

In some embodiments, interferon lambda (e.g., pegylated lambda, e.g., pegylated lambda-1a) is administered weekly. In some embodiments, the interferon lambda is administered at a dose of 120 mcg QW or 180 mcg QW. In some embodiments, the interferon lambda is administered at a dose of 120 micrograms per week.

In some embodiments, interferon lambda is administered at a dose of 120 micrograms per week. In some embodiments, interferon lambda is administered at a dose of 180 micrograms per week. In some embodiments, the interferon lambda is subcutaneously administered.

In some embodiments, interferon alpha or lambda therapy is administered in conjunction with an RNAi component, and optionally a nucleos(t)ide analog (NUC), for treating a HDV infection in a patient for at least 1 month, 2 months, 3 months, 4 months, 5 months, 6 months or longer.

In some embodiments, the administration of the nucleos(t)ide analog (NUC) is continued once the administration of the effective amount of the pharmaceutical composition comprising the RNAi component stops.

In some embodiments, the patients are HBeAg positive. In some embodiments, the patients are HBeAg negative.

In some embodiments, the HBsAg level in the patient is reduced by at least about $\log_{10}$ 0.5, about $\log_{10}$ 0.75, about $\log_{10}$ 1, about $\log_{10}$ 1.25, about $\log_{10}$ 1.5, about $\log_{10}$ 1.75, about $\log_{10}$ 2 or about $\log_{10}$ 2.5 from level at start of treatment (Day 1). In some embodiments, the HBeAg level in the patient is reduced by at least about $\log_{10}$ 0.5, about $\log_{10}$ 0.75, about $\log_{10}$ 1, about $\log_{10}$ 1.25, about $\log_{10}$ 1.5, about $\log_{10}$ 1.75, about $\log_{10}$ 2 or about $\log_{10}$ 2.5 from level at start of treatment (Day 1). In some embodiments, the HBcrAg level in the patient is reduced by at least about $\log_{10}$ 0.5, about $\log_{10}$ 0.75, about $\log_{10}$ 1, about $\log_{10}$ 1.25, about $\log_{10}$ 1.5, about $\log_{10}$ 1.75, about $\log_{10}$ 2 or about $\log_{10}$ 2.5 from level at start of treatment (Day 1). In some embodiments, the HBV DNA level in the patient is reduced by at least about $\log_{10}$ 0.5, about $\log_{10}$ 1, about $\log_{10}$ 1.5, about $\log_{10}$ 2, about $\log_{10}$ 3, about $\log_{10}$ 4, about $\log_{10}$ 5 or about $\log_{10}$ 7.5 from level at start of treatment (Day 1). In some embodiments, the HBV RNA level in the patient is reduced by at least about $\log_{10}$ 0.5, about $\log_{10}$ 0.75, about $\log_{10}$ 1, about $\log_{10}$ 1.25, about $\log_{10}$ 1.5, about $\log_{10}$ 1.75, about $\log_{10}$ 2 or about $\log_{10}$ 2.5 from level at start of treatment (Day 1).

The application also relates to an effective amount of an RNAi component and optionally at least one anti-HBV agent (other than the RNAi component) and/or at least one anti-HDV agent (other than the RNAi component), more particularly at least one anti-HBV agent, wherein the at least one anti-HBV agent is a nucleos(t)ide analog (NUC) or IFN, each of which as that described herein, in the manufacture of a medicament for treating a Hepatitis D Virus (HDV) infection in a subject, preferably a human subject. In some embodiments, the RNAi component is for administration once monthly (or Q4W), once every two months (or Q8W), or once every three months (or Q12W) to a subject in a dose of about 40-200 mg, more particularly 100 mg, 150 mg, or 200 mg, more particularly 100 mg; the nucleos(t)ide analog (NUC) is for administration to a subject in a daily dose of about 0.1-600 mg, about 0.1-5 mg, about 5-50 mg, about 200-500 mg, about 100 mg, about 150 mg, about 300 mg, or about 600 mg, more particularly a daily dose of entecavir of about 0.1-5 mg, a daily dose of about 5-50 mg of tenofovir alafenamide, a daily dose of about 200-500 mg of tenofovir disoproxil, a daily dose of about 100 mg, about 150 mg, or about 300 mg of lamivudine, or a daily dose of about 600 mg of telbivudine. In some embodiment, the medicament is for administering to a subject infected with HDV, in particular, a subject having a HDV/HBV co-infection.

EMBODIMENTS

Embodiment 1 is a method for treating a Hepatitis D Virus (HDV) infection in a subject in need thereof, preferably a human subject in need thereof, wherein the method comprises administering to the subject an effective amount of a pharmaceutical composition comprising an RNAi component having:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is administered to the subject via intravenous or subcutaneous injection.

Embodiment 2 is the method of embodiment 1, wherein the RNAi component is administered once monthly (or Q4W), once every two months (or Q8W), or once every three months (or Q12W), more particularly once monthly.

Embodiment 3 is the method of embodiment 2, wherein the RNAi component is administered in a dose of about 40-200 mg, more particularly 100 mg, 150 mg, or 200 mg, more particularly 100 mg.

Embodiment 4 is the method of any one of embodiments 1-3, which further comprises administering to the subject:

an effective amount of a pharmaceutical composition comprising an agent other than the RNAi component, more particularly an effective amount of an anti-HBV agent and/or an anti-HDV agent, more particularly an effective amount of a pharmaceutical composition comprising an anti-HBV agent, wherein the anti-HBV agent is a nucleos(t)ide analog (NUC) or an IFN, more particularly an effective amount of a pharmaceutical composition comprising a nucleoside analog or a nucleotide analog.

Embodiment 4a is the method of any one of embodiments 1-3, which further comprises administering to the subject:

an effective amount of a pharmaceutical composition comprising an agent other than the RNAi component, more particularly an effective amount of an anti-HBV agent and/or an anti-HDV agent, more particularly an effective amount of a pharmaceutical composition comprising an anti-HDV agent, wherein the anti-HDV agent is an HDV entry inhibitor and/or a farnesyl transferase inhibitor.

Embodiment 5 is the method of embodiment 4 or 4a, wherein the nucleos(t)ide analog (NUC) or interferon is not administered prior to the RNAi component or wherein the RNAi component is administered prior to or concurrently with the nucleos(t)ide analog (NUC) or interferon (IFN).

Embodiment 6 is the method of any one of embodiments 1-5, wherein the subject comprises a HDV/Hepatitis B Virus (HBV) co-infection.

Embodiment 7 is the method of any one of embodiments 1-6, wherein the subject further comprises cirrhosis, more particularly compensated cirrhosis.

Embodiment 7a is the method of any one of embodiments 1-6, wherein the subject is a patient without cirrhosis.

Embodiment 8 is the method of any one of embodiments 1-7, wherein the method comprises administering the effective amount of the pharmaceutical composition comprising the RNAi component at least until the subject meets at least one of, at least two of, at least three of, at least four of, or the five following features:

i. a serum HDV RNA level with an at least a 2 log decrease or an undetectable level of serum HDV RNA;

ii. a serum ALT concentration of 40 U/L or lower if the subject is a male subject or of 30 U/L or lower if the subject is a female subject, or a relative reduction (from baseline) of serum ALT concentration by at least 40%, more particularly by at least 50%;

iii. a HBeAg-negative serum;

iv. a serum HBsAg level of 100 IU/mL or lower, more particularly of 10 IU/mL or lower, more particularly HBsAg seroclearance; and v. HBs seroconversion.

Embodiment 9 is the method of embodiment 8, wherein the serum HDV RNA level is undetectable.

Embodiment 10 is the method of embodiment 8, wherein the serum HBsAg level is 100 IU/mL or lower, more particularly of 10 IU/mL or lower, more particularly HBsAg seroclearance.

Embodiment 11 is the method of any one embodiments 8-10, wherein at least one of, at least two of, at least three of, at least four of, or the five features of i., ii., iii., iv., and v. are still met six (6) months after the end of treatment.

Embodiment 12 the method of any one of embodiments 1-11, wherein the pharmaceutical composition comprising the RNAi component is administered to the subject for 1 year (48 weeks) or for at least 1 year (48 weeks), at least 2 years, at least 3 years, at least 4 years, at least 5 years, at least 6 years, at least 7 years, at least 8 years, at least 9 years, or at least 10 years.

Embodiment 13 is the method of any one of embodiments 8-12, wherein the administration of the pharmaceutical composition comprising the RNAi component is stopped after HBs seroconversion has been detected in the subject.

Embodiment 14 is the method of any one of embodiments 1-13, wherein the first or the second RNAi agent comprises at least one modified nucleotide and/or at least one modified internucleoside linkage.

Embodiment 15 is the method of any one of embodiments 1-14, wherein at least 90% of the nucleotides in the first and the second RNAi agents are modified nucleotides.

Embodiment 16 the method of any one of embodiments 1-15, wherein the first or the second RNAi agent further comprises a targeting ligand that is conjugated to the first or the second RNAi agent.

Embodiment 17 the method of embodiment 16, wherein the targeting ligand comprises N-acetyl-galactosamine.

Embodiment 18 the method of embodiment 17, wherein the targeting ligand is selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s.

Embodiment 19 is the method of embodiment 18, wherein the targeting ligand is (NAG25), (NAG25)s, (NAG31), (NAG31)s, (NAG37), or (NAG37)s.

Embodiment 20 is the method of any one of embodiments 16-19, wherein the targeting ligand is conjugated to the sense strand of the first or the second RNAi agent.

Embodiment 21 is the method of embodiment 20, wherein the targeting ligand is conjugated to the 5' terminus of the sense stand of the first or the second RNAi agent.

Embodiment 22 is the method of any one of embodiments 1-21, wherein the first and the second RNAi agents independently comprise a duplex selected from the group consisting of:

(a) an antisense strand comprising SEQ ID NO: 1 and a sense strand comprising SEQ ID NO: 10;

(b) an antisense strand comprising SEQ ID NO: 2 and a sense strand comprising SEQ ID NO: 11;

(c) an antisense strand comprising SEQ ID NO: 3 and a sense strand comprising SEQ ID NO: 11;

(d) an antisense strand comprising SEQ ID NO: 4 and a sense strand comprising SEQ ID NO: 12;

(e) an antisense strand comprising SEQ ID NO: 8 and a sense strand comprising SEQ ID NO:16;

(f) an antisense strand comprising SEQ ID NO: 8 and a sense strand comprising SEQ ID NO: 17;

(g) an antisense strand comprising SEQ ID NO: 2 and a sense strand comprising SEQ ID NO: 12; and (h) an antisense strand comprising SEQ ID NO: 8 and a sense strand comprising SEQ ID NO:18.

Embodiment 23 is the method of any one of embodiments 1-22, wherein the first and the second RNAi agents are each independently conjugated to a targeting ligand comprising N-acetyl-galactosamine, and the first and the second RNAi agents independently comprise a duplex selected from the group consisting of:

(a) an antisense strand comprising SEQ ID NO: 2 and a sense strand comprising SEQ ID NO: 11;

(b) an antisense strand comprising SEQ ID NO: 4 and a sense strand comprising SEQ ID NO: 12;

(c) an antisense strand comprising SEQ ID NO: 8 and a sense strand comprising SEQ ID NO: 16;

(d) an antisense strand comprising SEQ ID NO: 2 and a sense strand comprising SEQ ID NO: 13; and (e) an antisense strand comprising SEQ ID NO: 8 and a sense strand comprising SEQ ID NO: 18.

Embodiment 24 is the method of any one of embodiments 1-23, wherein the ratio of the first RNAi agent to the second RNAi agent by weight is in the range of about 1:2 to about 5:1.

Embodiment 25 is the method of embodiment 24, wherein the ratio of the first RNAi agent to the second RNAi agent by weight is about 2:1.

Embodiment 26 is the method of embodiment 1 further comprising administering to the subject an effective amount of a pharmaceutical composition comprising a nucleoside analog or a nucleotide analog.

Embodiment 27 is the method of embodiment 4 or 26, wherein the nucleoside analog is entecavir, tenofovir disoproxil fumarate, tenofovir alafenamide, lamivudine, telbivudine, or a combination thereof.

Embodiment 28 is the method of embodiment 27, wherein entecavir is administered to the subject in a daily dose of about 0.1-5 mg.

Embodiment 29 is the method of embodiment 27, wherein tenofovir is administered to the subject in a daily dose of about 5-50 mg of tenofovir alafenamide or about 200-500 mg of tenofovir disoproxil fumarate.

Embodiment 30 is the method of embodiment 27, wherein lamivudine is administered to the subject in a daily dose of about 100 mg, about 150 mg or about 300 mg.

Embodiment 31 is the method of embodiment 27, wherein telbivudine is administered to the subject in a daily dose of about 600 mg.

Embodiment 32 is the method of embodiment 26, wherein the administration of the nucleoside analog or the nucleotide analog is continued once the administration of the effective amount the pharmaceutical composition comprising the RNAi component stops.

Embodiment 33 is the method of any one of embodiments 1-32, wherein the RNAi component is contained in a syringe, for example a glass syringe, and wherein the syringe is optionally suitable for self-administration of the RNAi component by the patient or for administration of the RNAi component to the patient by an untrained personnel.

Embodiment 34 is the method of embodiment 33, wherein the syringe is suitable for self-administration of the RNAi component by the patient, and wherein the syringe is placed in an ergonomic shell or grip to stabilize the syringe for self-injection by the patient, or is provided in an autoinjector device.

Embodiment 35 is a kit comprising an effective amount of an RNAi component and an effective amount of an anti-HBV agent and/or an anti-HDV agent, more particularly an anti-HBV agent, wherein the anti-HBV agent is a nucleos(t)ide analog (NUC) or an interferon (IFN), wherein:

(a) the RNAi component comprises (i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the kit is for use in treating a Hepatitis D Virus (HDV) infection in a subject in need thereof, preferably a human subject in need thereof.

Embodiment 35a is a kit comprising an effective amount of an RNAi component and an effective amount of an anti-HBV agent and/or an anti-HDV agent, more particularly an anti-HDV agent, wherein the anti-HDV agent is an HDV entry inhibitor and/or an effective amount of a farnesyl transferase inhibitor, wherein:

(a) the RNAi component comprises (i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the kit is for use in treating a Hepatitis D Virus (HDV) infection in a subject in need thereof, preferably a human subject in need thereof.

Embodiment 36 is the kit of embodiment 35 or 35a further comprising instructions for carrying out any one of the methods of embodiments 1-34a.

Embodiment 37 is the kit of any one of embodiments 35-36 further comprising a pharmaceutically acceptable carrier, diluent, excipient or a combination of any of the foregoing.

Embodiment 38 is the kit of any one of embodiments 35-37, wherein the first or the second RNAi agent comprises at least one modified nucleotide and/or at least one modified internucleoside linkage.

Embodiment 39 is the kit of any one of embodiments 35-38, wherein substantially all of the nucleotides in the first and the second RNAi agents are modified nucleotides.

Embodiment 40 is the kit of any one of embodiments 35-39, wherein the first or the second RNAi agent further comprises a targeting ligand that is conjugated to the first or the second RNAi agent.

Embodiment 41 is the kit of embodiment 40, wherein the targeting ligand comprises N-acetyl-galactosamine.

Embodiment 42 is the kit of embodiment 41, wherein the targeting ligand is selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s.

Embodiment 43 is the kit of embodiment 42, wherein the targeting ligand is (NAG25), (NAG25)s, (NAG31), (NAG31)s, (NAG37), or (NAG37)s.

Embodiment 44 is the kit of any one of embodiments 40-43, wherein the targeting ligand is conjugated to the sense strand of the first or the second RNAi agent.

Embodiment 45 is the kit of embodiment 44, wherein the targeting ligand is conjugated to the 5' terminus of the sense stand of the first or the second RNAi agent.

Embodiment 46 is the kit of any one of embodiments 35-45, wherein the first and the second RNAi agents independently comprise a duplex selected from the group consisting of:

(a) an antisense strand comprising SEQ ID NO: 1 and a sense strand comprising SEQ ID NO: 10;
(b) an antisense strand comprising SEQ ID NO: 2 and a sense strand comprising SEQ ID NO: 11;
(c) an antisense strand comprising SEQ ID NO: 3 and a sense strand comprising SEQ ID NO: 11;
(d) an antisense strand comprising SEQ ID NO: 4 and a sense strand comprising SEQ ID NO: 12;
(e) an antisense strand comprising SEQ ID NO: 8 and a sense strand comprising SEQ ID NO:16;
(f) an antisense strand comprising SEQ ID NO: 8 and a sense strand comprising SEQ ID NO: 17;
(g) an antisense strand comprising SEQ ID NO: 2 and a sense strand comprising SEQ ID NO: 12; and
(h) an antisense strand comprising SEQ ID NO: 8 and a sense strand comprising SEQ ID NO:18.

Embodiment 47 is the kit of any one of embodiments 35-46, wherein the first and the second RNAi agents are each independently conjugated to a targeting ligand comprising N-acetyl-galactosamine, and the first and the second RNAi agents independently comprise a duplex selected from the group consisting of:

(a) an antisense strand comprising SEQ ID NO: 2 and a sense strand comprising SEQ ID NO: 11;
(b) an antisense strand comprising SEQ ID NO: 4 and a sense strand comprising SEQ ID NO: 12;
(c) an antisense strand comprising SEQ ID NO: 8 and a sense strand comprising SEQ ID NO: 16;
(d) an antisense strand comprising SEQ ID NO: 2 and a sense strand comprising SEQ ID NO: 13; and
(e) an antisense strand comprising SEQ ID NO: 8 and a sense strand comprising SEQ ID NO: 18.

Embodiment 48 is the kit of any one of embodiments 35-47, wherein the ratio of the first RNAi agent to the second RNAi agent by weight is in the range of about 1:2 to about 5:1.

Embodiment 49 is the kit of embodiment 48, wherein the ratio of the first RNAi agent to the second RNAi agent by weight is about 2:1.

Embodiment 50 is the kit of any one of embodiments 35-49, wherein the first RNAi agent comprises an antisense strand comprising SEQ ID NO: 2 and a sense strand comprising SEQ ID NO: 11, the second RNAi agent comprises an antisense strand comprising SEQ ID NO: 8 and a sense strand comprising SEQ ID NO: 16.

Embodiment 51 is the kit of any one of embodiments 35-50, wherein the RNAi component is formulated for intravenous or subcutaneous injection to the subject.

Embodiment 52 is the kit of any one of embodiments 35-51, wherein the nucleos(t)ide analog (NUC) is entecavir, tenofovir disoproxil fumarate, tenofovir alafenamide, lamivudine, telbivudine, or a combination thereof, more particularly entecavir, tenofovir disoproxil fumurate, tenofovir alafenamide, or a combination thereof.

Embodiment 53 is the kit of any one of embodiments 35-52, wherein the RNAi component is included for once monthly administration to a subject in a dose of about 40-250 mg, more particularly 40-200 mg, more particularly 100 mg, 150 mg, or 200 mg, more particularly 100 mg.

Embodiment 54 is the kit of any one of embodiments 35-53, wherein the RNAi component and the nucleoside or nucleotide analog are for administration to a subject co-infected with HDV and HBV, in particular, a subject having a chronic HDV/HBV co-infection.

Embodiment 55 is a combination comprising an effective amount of an RNAi component and an effective amount of an anti-HBV agent and/or anti-HDV agent, more particularly an anti-HBV agent, wherein the anti-HBV agent is a nucleos(t)ide analog (NUC) or an interferon (IFN), wherein:

(a) the RNAi component comprises
(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and
(ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the combination is for use in treating a Hepatitis D Virus (HDV) infection in a subject in need thereof, preferably a human subject in need thereof.

Embodiment 55a is a combination comprising an effective amount of an RNAi component and an effective amount of an anti-HBV agent and/or anti-HDV agent, more particularly an anti-HDV agent, wherein the anti-HDV agent is an HDV entry inhibitor and/or an effective amount of a farnesyl transferase inhibitor, wherein:

(a) the RNAi component comprises
(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and
(ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the combination is for use in treating a Hepatitis D Virus (HDV) infection in a subject in need thereof, preferably a human subject in need thereof.

Embodiment 56 is the combination of embodiment 55 or 55a further comprising instructions for carrying out any one of the methods of embodiments 1-34.

Embodiment 57 is the combination of any one of embodiments 55-56 further comprising a pharmaceutically acceptable carrier, diluent, excipient or a combination of any of the foregoing.

Embodiment 58 is the combination of any one of embodiments 55-57, wherein the first or the second RNAi agent comprises at least one modified nucleotide and/or at least one modified internucleoside linkage.

Embodiment 59 is the combination of any one of embodiments 55-58, wherein substantially all of the nucleotides in the first and the second RNAi agents are modified nucleotides.

Embodiment 60 is the combination of any one of embodiments 55-59, wherein the first or the second RNAi agent further comprises a targeting ligand that is conjugated to the first or the second RNAi agent.

Embodiment 61 is the combination of embodiment 60, wherein the targeting ligand comprises N-acetyl-galactosamine.

Embodiment 62 is the combination of embodiment 61, wherein the targeting ligand is selected from the group consisting of (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s.

Embodiment 63 is the combination of embodiment 62, wherein the targeting ligand is (NAG25), (NAG25)s, (NAG31), (NAG31)s, (NAG37), or (NAG37)s.

Embodiment 64 is the combination of any one of embodiments 60-63, wherein the targeting ligand is conjugated to the sense strand of the first or the second RNAi agent.

Embodiment 65 is the combination of embodiment 64, wherein the targeting ligand is conjugated to the 5' terminus of the sense stand of the first or the second RNAi agent.

Embodiment 66 is the combination of any one of embodiments 55-65, wherein the first and the second RNAi agents independently comprise a duplex selected from the group consisting of:

(a) an antisense strand comprising SEQ ID NO: 1 and a sense strand comprising SEQ ID NO: 10;

(b) an antisense strand comprising SEQ ID NO: 2 and a sense strand comprising SEQ ID NO: 11;

(c) an antisense strand comprising SEQ ID NO: 3 and a sense strand comprising SEQ ID NO: 11;

(d) an antisense strand comprising SEQ ID NO: 4 and a sense strand comprising SEQ ID NO: 12;

(e) an antisense strand comprising SEQ ID NO: 8 and a sense strand comprising SEQ ID NO:16;

(f) an antisense strand comprising SEQ ID NO: 8 and a sense strand comprising SEQ ID NO: 17;

(g) an antisense strand comprising SEQ ID NO: 2 and a sense strand comprising SEQ ID NO: 12; and (h) an antisense strand comprising SEQ ID NO: 8 and a sense strand comprising SEQ ID NO:18.

Embodiment 67 is the combination of any one of embodiments 55-66, wherein the first and the second RNAi agents are each independently conjugated to a targeting ligand comprising N-acetyl-galactosamine, and the first and the second RNAi agents independently comprise a duplex selected from the group consisting of:

(a) an antisense strand comprising SEQ ID NO: 2 and a sense strand comprising SEQ ID NO: 11;

(b) an antisense strand comprising SEQ ID NO: 4 and a sense strand comprising SEQ ID NO: 12;

(c) an antisense strand comprising SEQ ID NO: 8 and a sense strand comprising SEQ ID NO: 16;

(d) an antisense strand comprising SEQ ID NO: 2 and a sense strand comprising SEQ ID NO: 13; and (e) an antisense strand comprising SEQ ID NO: 8 and a sense strand comprising SEQ ID NO: 18.

Embodiment 68 is the combination of any one of embodiments 55-67, wherein the ratio of the first RNAi agent to the second RNAi agent by weight is in the range of about 1:2 to about 5:1.

Embodiment 69 is the combination of embodiment 68, wherein the ratio of the first RNAi agent to the second RNAi agent by weight is about 2:1.

Embodiment 70 is the combination of any one of embodiments 55-69, wherein the first RNAi agent comprises an antisense strand comprising SEQ ID NO: 2 and a sense strand comprising SEQ ID NO: 11, the second RNAi agent comprises an antisense strand comprising SEQ ID NO: 8 and a sense strand comprising SEQ ID NO: 16.

Embodiment 71 is the combination of any one of embodiments 55-70, wherein the RNAi component is formulated for intravenous or subcutaneous injection to a subject.

Embodiment 72 is the combination of any one of embodiments 55-71, wherein the nucleos(t)ide analog (NUC) is entecavir, tenofovir disoproxil fumarate, tenofovir alafenamide, lamivudine, telbivudine, or a combination thereof, more particularly entecavir, tenofovir disoproxil fumurate, tenofovir alafenamide, or a combination thereof.

Embodiment 73 is the combination of any one of embodiments 55-72, wherein the RNAi component is included for once monthly administration to a subject in a dose of about 40-250 mg, more particularly 40-200 mg, more particularly 100 mg, 150 mg, or 200 mg, more particularly 100 mg.

Embodiment 74 is the combination of any one of embodiments 55-73, wherein the RNAi component and the nucleoside or nucleotide analog are for administration to a subject co-infected with HDV and HBV, in particular, a subject having a chronic HDV/HBV co-infection.

Embodiment 75 is an effective amount of an RNAi component in the manufacture of a medicament for treating a Hepatitis D viral (HDV) infection in a subject, preferably a human subject, wherein:

the RNAi component comprises (i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is for once monthly (or Q4W), once every two months (or Q8W), or once every three months (or Q12W), more particularly once monthly administration to a subject in a dose of about 40-200 mg, more particularly 100 mg, 150 mg, or 200 mg, more particularly 100 mg.

Embodiment 76 a pharmaceutical composition for use in the treatment of a Hepatitis D Virus infection in a subject in need thereof, preferably a human subject in need thereof, wherein the pharmaceutical composition comprises an effective amount of an RNAi component, wherein the RNAi component comprises:

(i) a first RNAi agent comprising: an antisense strand comprising a nucleotide sequence of any one of the following: SEQ ID NO:1, SEQ ID NO:2, SEQ ID NO:3, SEQ ID NO:4, SEQ ID NO:5, SEQ ID NO:6, and SEQ ID NO:7 and a sense strand comprising a nucleotide sequence of any one of the following: SEQ ID NO:10, SEQ ID NO:11, SEQ ID NO:12, SEQ ID NO:13, SEQ ID NO:14, and SEQ ID NO:15; and (ii) a second RNAi agent comprising: an antisense strand comprising a nucleotide sequence of any one of the following: SEQ ID NO:8 and SEQ ID NO:9, and a sense strand comprising a nucleotide sequence of any one of the following: SEQ ID NO:16, SEQ ID NO:17, SEQ ID NO:18, and SEQ ID NO:19, wherein the RNAi component is formulated for administration to the subject via intravenous or subcutaneous injection.

Embodiment 77 is the pharmaceutical composition for use of embodiment 76, wherein the RNAi component is formulated for administration once monthly (or Q4W), once every two months (or Q8W), or once every three months (or Q12W), more particularly once monthly.

Embodiment 78 is the pharmaceutical composition for use of embodiment 76 or 77, wherein the RNAi component is formulated for administration in a dose of about 40-200 mg, more particularly 100 mg, 150 mg, or 200 mg, more particularly 100 mg.

Embodiment 79 is the pharmaceutical composition for use of any one of embodiments 76-78, wherein the treatment further comprises administering an effective amount of an anti-HBV agent and/or anti-HDV agent, more particularly an effective amount of an anti-HBV-agent, wherein the anti-HBV agent is a nucleos(t)ide analog (NUC) or of an interferon (IFN), more particularly an effective amount of a nucleoside analog or a nucleotide analog.

Embodiment 79a is the pharmaceutical composition for use of any one of embodiments 76-78, wherein the treatment further comprises administering an effective amount of an anti-HBV agent and/or anti-HDV agent, more particularly an effective amount of an anti-HDV-agent, more particularly an effective amount of an HDV entry inhibitor and/or an effective amount of a farnesyl transferase inhibitor.

Embodiment 80 is the pharmaceutical composition for use of embodiment 79, wherein the nucleos(t)ide analog (NUC) or interferon (IFN) is not administered prior to the RNAi component.

Embodiment 81 is the pharmaceutical composition for use of embodiment 79 or 80, wherein the RNAi component is administered prior to or concurrently with the nucleos(t)ide analog (NUC) or interferon (IFN).

Embodiment 82 is the pharmaceutical composition for use of any one of embodiments 76-81, wherein the subject comprises a HDV/Hepatitis B Virus (HBV) co-infection.

Embodiment 83 is the pharmaceutical composition for use of any one of embodiments 76-82, wherein the subject further comprises cirrhosis, more particularly compensated cirrhosis.

Embodiment 83a is the pharmaceutical composition for use of any one of embodiments 76-82, wherein the subject is a patient without cirrhosis.

Embodiment 84 is the pharmaceutical composition for use of any one of embodiments 76-83a, wherein the effective amount of the RNAi component is administered to the subject at least until the subject meets at least one of, at least two of, at least three of, at least four of, or the five following features:

i. a serum HDV RNA level with at least a 2 fold decrease or an undetectable level of serum HDV RNA;

ii. a serum ALT concentration of 40 U/L or lower if the subject is a male subject or of 30 U/L or lower if the subject is a female subject, or a relative reduction (from baseline) of serum ALT concentration by at least 40%, more particularly by at least 50%;

iii. a HBeAg-negative serum;

iv. a serum HBsAg level of 100 IU/mL or lower, more particularly of 10 IU/mL or lower, more particularly HBsAg seroclearance; and v. HBs seroconversion.

Embodiment 85 is the pharmaceutical composition for use of embodiment 84, wherein the serum HDV RNA level is undetectable.

Embodiment 86 is the pharmaceutical composition for use of embodiment 84, wherein the serum HBsAg level is 100 IU/mL or lower, more particularly of 10 IU/mL or lower, more particularly HBsAg seroclearance.

Embodiment 87 is the pharmaceutical composition for use of any one of embodiments 84-86, wherein at least one of, at least two of, at least three of, at least four of, or the five features of i., ii., iii., iv., and v. are still met six (6) months after the end of treatment.

Embodiment 88 is the pharmaceutical composition for use of any one of embodiments 76-87, wherein the effective amount of the RNAi component is administered to the subject for 1 year (48 weeks), or for at least 1 year (48 weeks), at least 2 years, at least 3 years, at least 4 years, at least 5 years, at least 6 years, at least 7 years, at least 8 years, at least 9 years, or at least 10 years.

Embodiment 89 is the pharmaceutical composition for use of any one of embodiments 84-88, wherein the administration of the effective amount of the RNAi component is stopped after the serum HBsAg level is 100 IU/mL or lower, more particularly of 10 IU/mL of lower.

Embodiment 90 is the pharmaceutical composition for use of any one of embodiments 84-89, wherein the administration of the effective amount of the RNAi component is stopped after HBs seroconversion has been detected in the subject.

Embodiment 91 is the pharmaceutical composition for use of any one of embodiments 79-90, wherein the administration of the nucleos(t)ide analog (NUC) or of the interferon is continued after stopping the administration of the effective amount of the RNAi component.

Embodiment 92 is the pharmaceutical composition for use of any one of embodiments 76-91, wherein the pharmaceutical composition further comprises a pharmaceutically acceptable carrier, diluent, excipient, or a combination of any of the foregoing.

Embodiment 93 is the pharmaceutical composition for use of any one of embodiments 76-92, wherein the RNAi component is contained in a syringe, for example a glass syringe, and wherein the syringe is optionally suitable for self-administration of the RNAi component by the patient or for administration of the RNAi component to the patient by an untrained personnel.

Embodiment 94 is the pharmaceutical composition for use of embodiment 93, wherein the syringe is suitable for self-administration of the RNAi component by the patient, and wherein the syringe is placed in an ergonomic shell or grip to stabilize the syringe for self-injection by the patient, or is provided in an autoinjector device.

EXAMPLES

The following examples are offered to illustrate but not to limit the invention. One of skill in the art will recognize that the following procedures may be modified using methods known to one of ordinary skill in the art.

Example 1

Study Design:

A target population of approximately 125 male and female participants, 16 to 65 years of age (inclusive) are sought to study the effects of the RNAi and nucleoside analog treatment. The aim is to enroll adolescent participants (≥16 to <18 years of age) in selected countries and study sites consistent with local regulations.

Participants are randomized in a 4:1 ratio (Arm 1:Arm 2) to one of the following arms and are to receive the following: (a) Arm 1: 100 mg RNAi component (subcutaneous [SC] injection every 4 weeks [Q4W])+nucleos(t)ide analog (NA) daily (qd) for 144 weeks (n=100; immediate active treatment arm); (b) Arm 2: placebo for RNAi component (SC injection Q4W)+NA qd for 52 weeks, followed by 100 mg RNAi component (SC injection Q4W)+NA qd for 96 weeks (n=25; deferred active treatment arm).

NA=nucleos(t)ide analog=entecavir monohydrate (ETV), tenofovir disoproxil, or tenofovir alafenamide (TAF). NA treatment is started from Day 1 in both arms.

Treatment with the RNAi component (given as 3 SC injections Q4W) has shown substantial reduction in HbsAg previously. No difference in tolerability and safety was noted between the different RNAi component doses. No apparent dose response was observed at doses between 100 and 400 mg, suggesting that maximal HBsAg reduction in the study was reached with those doses. A slightly reduced mean decline was observed at the lower doses of 25 mg and 50 mg. Although no clear dose response was observed in the study, a conservative approach is considered for this study, given that patients with cirrhosis are included and the overall duration of treatment in the previous study was limited to 3 months (3 injections). The 100 mg dose is selected for this study given the longer treatment duration and the primary study objective to achieve on-treatment HDV RNA reduction/suppression.

After completion of the study intervention phase, treatment with the RNAi component is stopped and the participants enter the follow-up phase of 48 weeks. For participants without cirrhosis, NA treatment during the follow-up phase is at the investigator's discretion. Participants with cirrhosis continue to receive NA treatment during follow-up. During the follow-up period, sustained HDV and HBV response is assessed. See FIG. 1, a schematic overview of the study.

The study is conducted in 3 phases for all participants: 4-week screening phase (may be extended for up to a maximum of 6 weeks), 144 weeks study intervention phase (Arm 1), and 148-weeks study intervention phase (Arm 2), and 48-week follow-up phase Assessments and sampling in blood include efficacy (e.g., HDV RNA, HBsAg, HBV DNA), safety (e.g., adverse effects (AEs), laboratory abnormalities, ECGs), pharmacokinetics (PK), PK/pharmacodynamics (PD), viral genome sequencing/genotyping, peripheral blood mononuclear cells (PBMC), HLA typing, exploratory biomarker, and pharmacogenomics samples. Clinical outcomes such as death, cirrhosis decompensation, or liver transplantation are captured.

The primary analysis of this study is performed when the last participant has reached study visit week 48 or has discontinued earlier. Participants are considered to have completed the study if they have completed the assessments of the end of study (EOS) visit (i.e., FU week 48). In the case of a premature discontinuation of the RNAi component/placebo (before week 144 (Arm 1) or week 148 (Arm 2)), participants are withdrawn early and enter the 48 weeks of follow-up unless the participant chooses to withdraw consent/assent. In the case a participant withdraws consent before completing the study, the reason (if known) is documented. Participants who withdraw consent are offered an optional safety follow-up visit.

An Independent Data Monitoring Committee (IDMC) is commissioned for this study. In addition, an Independent Flare Expert Panel (iFLEP) is appointed. A futility analysis is conducted by the IDMC to assess whether there is early evidence supporting the conclusion of no robust HBsAg decline in this HBV/HDV co-infected population. The futility criterion is defined in terms of efficacy response as measured by a predefined threshold of HBsAg reduction from baseline.

The RNAi component is a siRNA specifically engineered to silence all HBV viral products, including HBsAg. In the previous study with HBV mono-infected patients, the administration of the RNAi component has been associated with a significant decline in HBsAg level with three (3) monthly doses.

Therapies that efficiently decrease levels of HBsAg in patients with HBV/HDV co-infection are expected to lead to suppression or inhibition of the HDV replication (as measured by reduction of HDV RNA in blood). Complete suppression (i.e., seroclearance) of HBsAg is expected to lead to sustained control of HDV infection, either in response to chronic suppression by continued treatment or by achieving a HBV functional cure after completion of therapy.

Study Population: Patients with HBV/HDV co-infection are eligible for the study.

NA Treatment: All participants receive NA treatment during the entire treatment period to maximize the resistance barrier of the regimen and to ensure complete HBV suppression since reduction in HDV replication can be associated with increased HBV replication. For similar reasons, and consistent with treatment guidelines, after the end of RNAi component treatment, NA treatment is continued in patients with cirrhosis, while NA treatment is stopped in non-cirrhotic patients at the investigator's discretion within the controlled clinical setting.

Providing the NA in the deferred active arm from day 1 onward increases the validity and robustness of the comparisons and ensures that NA is given to all patients who have an indication for NA treatment (i.e., patients with cirrhosis and/or patients with detectable HBV DNA). This approach is consistent with other HDV studies.

Deferred Active Arm: To characterize efficacy and safety of the investigational treatment regimen, a double-blind comparison of the RNAi component versus placebo on the background of NA treatment during the first 48 weeks of the study intervention is included. Therefore, to safeguard the blinding of the week 48 assessments, participants on placebo are switched to active RNAi component at the week 52 visit, at which investigator and patient are unblinded about the treatment allocations during week 1 to 48. Participants in both intervention arms will continue with the RNAi component plus NA until week 144 (Arm 1) and week 148 (Arm 2) in an open-label fashion. Delaying active therapy with 52 weeks is the longest period deemed acceptable in this population.

Randomization: Randomization is used to minimize bias in the assignment of participants to intervention arms, to increase the likelihood that known and unknown participant attributes (e.g., demographic and baseline characteristics) are evenly balanced across treatment arms, and to enhance the validity of statistical comparisons across intervention arms.

Stratification Factors: Randomization is stratified by presence of compensated cirrhosis (patients with cirrhosis versus patients without cirrhosis) as screening (yes or no) in order to provide a reasonably balanced representation across the two arms.

Blinding: The first 52 weeks of the study is double-blinded.

TABLE 1

| Study Characteristics | |
|---|---|
| Characteristic | Study |
| Multicenter or Single Center | Multicenter (2-step integrated study design with a PoC part upfront (Part 1) followed by the pivotal Part 2) |
| Primary Indication | HDV |
| Additional Indications | HBV |
| Target Study Participation | Participants co-infected with HBV and HDV<br>Participants with compensated cirrhosis are allowed to be enrolled |
| Number of Participants (in total) | (about) 125 |
| Participant Minimum Age | 16 years or higher if required by local regulation |
| Participant Maximum Age | 65 years |
| Study Uses Healthy Participants | No |
| Participant Duration | Up to 198 weeks for Arm 1<br>Up to 202 weeks for Arm 2 |
| Randomized Study | Yes, participants are randomized 4:1 to immediate treatment arm versus deferred treatment arm<br>Randomization is stratified by presence of compensated cirrhosis (yes or no) at screening |
| Participant Sex (biologically) | Males and Females |
| Pediatrics Study | Yes (if recruited) |
| If Pediatrics, specify age:<br>Pre-term and neonate (birth to 27 days)<br>Infant (28 days to 23 months)<br>Children (2 yrs to 11 yrs)<br>Adolescents (12 yrs to 17 yrs) | Adolescents: ≥16 yrs to <18 yrs of age, in line with local regulations |
| Blinding | Double-blinded for the first 52 weeks |
| Control | Placebo |
| Study Configuration (e.g., parallel group, crossover, up-titration) | Parallel with roll over from placebo for RNAi component to 100 mg RNAi component at week 52 (deferred active arm) |
| Investigation type (e.g., interventional, observational, expanded access) | Interventional |

TABLE 2

| Objectives and Endpoints | |
|---|---|
| Objectives | Endpoints |
| Primary | |
| To evaluate on-treatment efficacy against HDV of RNAi component plus NA regimen compared to NA alone | Proportion of participants with HDV RNA ≥ 2 $\log_{10}$ IU/mL decline from baseline or target not detected (TND) in combination with normal ALT at week 48 |
| Key Secondary | |
| To evaluate the efficacy of the RNAi component plus NA regimen as measured by HDV during study intervention phase and follow-up phase | Proportion of participants with HDV RNA ≥ 2 $\log_{10}$ IU/mL decline from baseline or HDV virologic markers RNA TND<br>Proportion of participants with normal ALT |
| To evaluate efficacy as measured by HBV blood markers during study intervention and follow-up phase | Proportion of participants with HBsAg seroclearance and/or seroconversion |
| Other Secondary | |
| To evaluate the efficacy of the RNAi component plus NA regimen during study intervention phase and follow-up phase | Proportion of participants with HDV RNA ≥ 2 $\log_{10}$ IU/mL decline from baseline or TND in combination with normal ALT<br>Proportion of participants with HDV RNA ≥ 2 $\log_{10}$ IU/mL decline from baseline in combination with normal ALT<br>Proportion of participants with HDV RNA TND in combination with normal ALT<br>Proportion of participants with HDV RNA ≥ 2 $\log_{10}$ IU/mL decline from baseline<br>Proportion of participants with HDV RNA TND<br>Proportion of participants with normal ALT<br>Time to reach HDV RNA ≥ 2 $\log_{10}$ IU/mL decline and HDV RNA TND |

TABLE 2-continued

Objectives and Endpoints

| Objectives | Endpoints |
|---|---|
| | Mean changes from baseline in HDV RNA<br>Proportion of patients with on-treatment HDV RNA increase (e.g., 1 log increase from nadir) |
| To evaluate the safety and tolerability of the study intervention throughout the study | Proportion of participants with incidences of (S) AEs and abnormalities in clinical laboratory tests (including hematology, blood biochemistry, blood coagulation, urinalysis, urine chemistry, and renal biomarkers), 12-lead ECGs, and vital signs |
| To evaluate the frequency of HBV virologic breakthrough | Proportion of participants with HBV DNA virologic breakthrough |
| To evaluate the PK of RNAi component and optionally NA | PK parameters of RNAi component and optionally NA |
| To evaluate changes in the severity of liver disease at week 48 and end of study intervention versus screening/baseline | Changes in fibrosis (according to Fibroscan liver stiffness measurements) |
| To evaluate efficacy as measured by HBV blood markers (such as HBsAg, HBeAg, HBV DNA) during study intervention and follow-up | Change from baseline over time in HBsAg, HBeAg*, HBV DNA<br>Proportion of participants with HBsAg, HBeAg and/or HBV DNA levels or changes from baseline below/above different cut-offs<br>Time to reach efficacy thresholds such as HBsAg <1 IU/mL |
| To evaluate the efficacy during the follow-up phase | Frequency of HDV relapse post end of RNAi component treatment<br>Proportions of participants with sustained HDV response off-treatment post end of RNAi treatment |
| To evaluate the anti-HBV efficacy during the follow-up phase | Frequency of HBV flare (virologic, biochemical, and clinical) post end of RNAi component treatment<br>Proportions of participants with sustained HBV response off-treatment post end of RNAi component treatment |
| To evaluate the impact of study intervention on participants' health-related quality of life (HRQoL) using patient-reported outcomes (PROs) during study intervention and follow-up | Changes over time in score on the Hepatitis B Quality of Live (HBQoL) scale and subscales |
| Exploratory | |
| To explore the relationship between PK parameters (RNAi component) and selected pharmacodynamic (PD) parameters of efficacy and/or safety | Relationship between various PK parameters (RNAi component) and selected efficacy and/or safety endpoints, as applicable |
| To explore the relationship between HBsAg and HDV RNA | Correlation between HBsAg decline and HDV RNA levels/changes |
| To explore the impact of the viral and host baseline characteristics on safety and efficacy | Correlation of viral and host baseline characteristics (such as HBV/HDV genotype, baseline HBV DNA levels, baseline HDV RNA levels, age, sex, body mass index (BMI)) with selected efficacy and safety variables |
| To explore the effect of any baseline variation in the HBV and HDV genome on efficacy | Correlation of HBV and HDV genome sequence with selected efficacy parameters |
| To explore efficacy as measured by HBV RNA and HBcrAg during study intervention and follow-up | Changes from baseline in HBV RNA an dHBcrAb levels<br>Time to reach undetectability of HBV RNA and HBcrAg |
| To explore changes in HBV and HDV genome sequence during study intervention and follow-up | Emergence of intervention-associated mutations |
| To explore T-cell responses during study intervention and follow-up** | Changes from baseline in peripheral blood T-cell responses |
| To explore the impact of study intervention on participants 'self-stigma and impression of change using PROs during study intervention and follow-up | Short form 36 version 2 (SF-36v2) 8 domain scores/subscales, physical component summary, and mental component summary scores<br>Changes over time in the 5-level EuroQol 5-dimension (EQ-5D-5L) visual analog scale (VAS) score and index score |

*in HBeAg-positive participants only

**Peripheral blood mononuclear cell (PBMC) samples for immune analyses is collected at selected sites only The following are the inclusion criteria for participation in the study:

1. Adult male or female participants 16 to 65 years of age, inclusive.
2. Participants must be medically stable on the basis of physical examination, medical history, vital signs, and 12-lead ECG performed at screening. If there are abnormalities, the abnormalities must be consistent with the underlying illness in the study population. This determination must be recorded in the participant's source documents and initialed by the investigator.
3. Participants must have chronic HBV infection documented by hbsag positivity at screening and anti-HDV antibodies at least 6 months prior to screening.
4. HDV RNA values at screening must be >500 IU/mL.
5. Participants are eligible for participation regardless of HBeAg status and treatment history. Participants who are receiving NA therapy at screening should be on a stable HBV treatment, defined as currently receiving ETV, tenofovir disoproxil, or TAF for at least 3 months prior to screening and having been on the same NA treatment regimen (at the same dose) during this period.
6. Participants must have ALT levels<10×ULN at screening.
7. Participants must have a BMI (weight in kg divided by the square of height in meters) between 18.0 and 35.0 $kg/m^2$ extremes included.
8. Participants must have: (a) fibroscan liver stiffness measurement<12.5 kPa within 6 months prior to screening or at the time of screening, OR (b) if a fibroscan result is not available, a liver biopsy result classified as Metavir F0-F4 within 1 year prior to screening or at the time of screening. (Note: other radiologic liver staging modalities (e.g., acoustic radiation force impulse) might be used if standard practice at the site or if otherwise validated and agreed with the sponsor. Results should be equivalent to Metavir F0-F4.)
9. Participants must sign an ICF indicating that they understand the purpose of, and procedures required for, the study and is willing to participate in the study. Parent(s) (preferably both if available or as per local requirements) (or their legally acceptable representative) must sign an ICF indicating that he or she understands the purpose of, and procedures required for, the study and is willing to allow the child to participate in the study. Assent is also required for participants≥16 to <18 years of age or as per local regulations.
10. Participants must sign a separate ICF if they agree to provide an optional DNA sample for research (where local regulations permit). Refusal to give consent for the optional DNA research sample does not exclude a participant from participation in the study. Parent(s) (preferably both if available or as per local requirements) (or their legally acceptable representative) must sign a separate informed consent form if he or she agrees to the child providing an optional DNA sample for research. Assent is also required for participants≥16 to <18 years of age.
11. Female participants of childbearing potential must have a negative highly sensitive serum pregnancy test (b-human chorionic gonadotropin) at screening and a negative urine pregnancy test on day 1 before the first dose of study intervention.
12. Female participants must be: (a) not of childbearing potential, or (b) of childbearing potential and practicing a highly effective, preferably user-independent method of contraception (failure rate of <1% per year when used consistently and correctly) for at least 30 days prior to screening and agree to remain on a highly effective method while receiving study intervention and until 90 days after last dose of study intervention.
13. Female participants must agree not to donate eggs (ova, oocytes) for the purposes of assisted reproduction while receiving study intervention and until 90 days after the last dose of study intervention.
14. Male participants must agree to wear a condom when engaging in any activity that allows for passage of ejaculate to another person while receiving study intervention and until 90 days after the last dose of study intervention.
15. Male participants must agree note to donate sperm for the purpose of reproduction while receiving study intervention and until 90 days after the last dose of study intervention.
16. In the investigator's opinion, the participant is able to understand and comply with protocol requirements, instructions, and lifestyle restrictions and be likely to complete the procedures as planned for this study.

The following are the exclusion criteria for participation in the study:

1. Participants with evidence of hepatitis A virus infection (hepatitis A antibody igm), HCV infection (HCV antibody), or hepatitis E virus infection (hepatitis E antibody igm), or HIV-1 or HIV-2 infection (confirmed by antibodies) at screening. (Note: Participants with a positive anti-HCV antibody test can be enrolled if they have negative HCV RNA at screening and documented negative HCV RNA at least 6 months prior to screening).
2. Participants with any of the following laboratory abnormalities within 12 months prior to screening or at time of screening:
   A. total bilirubin>1.5×ULN,
      Participants with higher total bilirubin values may be included after consultation with the study's medical monitor if such evaluation can be attributed to Gilbert's syndrome.
   B. direct bilirubin>1.2×ULN,
   C. prothrombin time>1.3×ULN,
   D. serum albumin<3.2 g/dL.
3. History or evidence of clinical signs/symptoms of hepatic decompensation including but not limited to: portal hypertension, ascites, hepatic encephalopathy.
4. Participants with Child-Pugh score>6 is excluded. (Note: Uncomplicated presence of mild esophageal varices is allowed. Participants with current bleeding or ligation, or history of bleeding or ligation of esophageal varices are excluded).
5. Participants with evidence of liver disease of non-HDV or HBV etiology. This includes, but is not limited to hepatitis virus infections mentioned in exclusion criterion, drug- or alcohol-related liver disease, autoimmune hepatitis, hemochromatosis, Wilson's disease, a-1 antitrypsin deficiency, primary biliary cholangitis, primary sclerosing cholangitis, Gilbert's syndrome (mild cases are allowed, see exclusion criterion), or any other non-HBV liver disease considered clinically significant by the investigator.
6. Participants with signs of HCC or clinically relevant renal abnormalities on an abdominal ultrasound performed within 6 months prior to screening or at the time of screening. In case of suspicious findings on conventional ultrasound the participant may still be eligible if HCC or clinically relevant renal abnormalities has been ruled out by a more specific imaging procedure (contrast enhanced ultrasound, CT or MRI).

7. Participants with one or more of the following laboratory abnormalities at screening as defined by the Division of Acquired Immunodeficiency Syndrome (DAIDS) Toxicity Grading Scale:
   A. estimated glomerular filtration rate (eGFR)≥grade 3 (i.e., <60 mL/min/1.73 m2) at screening, calculated by the Chronic Kidney Disease Epidemiology Collaboration (CKD-EPI) formula,
   B. pancreatic amylase≥grade 3,
   C. lipase elevation≥grade 3,
   D. hemoglobin≤10.9 g/dL (males, ≤10.4 g/dL (females),
   E. platelet count≤100,000 dL,
   F. alpha-fetoprotein (AFP)>100 ng/mL,
   G. any other laboratory abnormality considered to be clinically significant by the investigator (Note: participants with AFP>ULN (but ≤100 ng/mL) may be eligible if HCC can be ruled out based on a sensitive imaging study (e.g., enhanced ultrasound, CT, or MRI) during screening.
8. Participants with hemoglobin A1c>8% screening.
9. Participants with a history of malignancy within 5 years before screening (exceptions are squamous and basal cell carcinomas of the skin and carcinoma in situ of the cervix, or malignancy, which is considered cured with minimal risk of recurrence).
10. Participants with abnormal sinus rhythm (heart rate<45 or >100 beats per minute (bpm)); QT interval corrected for heart rate according to Fridericia (QTcF) >450 ms for male participants and >470 ms for female participants; QRS interval≥120 ms; PR interval>220 ms; abnormal conduction; or any other clinically significant abnormalities on a 12 lead ECG at screening.
11. Participants with a history of or current cardiac arrhythmias (e.g., tachycardia at rest), history of risk factors for Torsade de Pointes syndrome (e.g., hypokalemia, family history of long QT Syndrome) or history or other clinical evidence of significant or unstable cardiac disease (e.g., angina, congestive heart failure, myocardial infarction, diastolic dysfunction, significant arrhythmia, coronary heart disease), moderate to severe valvular disease, or uncontrolled hypertension at screening.
12. Participants with any current or previous illness for which, in opinion of the investigator and/or sponsor, participation would not be in the best interest of the participant (e.g., compromise the well-being) or that could prevent, limit, or confound the protocol-specified assessments. This may include, but is not limited to, significant vascular, pulmonary (e.g., chronic obstructive pulmonary disease), gastrointestinal (e.g., significant diarrhea, gastric stasis, or constipation that in the investigator's opinion could influence drug absorption or bioavailability), endocrine (e.g., thyroid disease), neurologic, hematologic, rheumatologic, psychiatric, neoplastic, or metabolic disturbances. Any condition possibly affecting drug absorption (e.g., gastrectomy or other significant gastrointestinal tract surgery, such as gastroenterostomy, small bowel resection, or active enterostomy) also lead to exclusion.
13. Participants with any history of or current clinically significant skin disease requiring regular or periodic treatment.
14. Participants with history of clinically relevant drug rash.
15. Participants with known allergies, hypersensitivity, or intolerance to RNAi component or their excipients.
16. Participants with contraindications to the use of ETV, tenofovir disoproxil, or TAF per local prescribing information.
17. Participants who have taken any disallowed therapies as noted in Section Concomitant Therapy before screening.
18. Participants having received an investigational intervention (including investigational vaccines) or used an invasive investigational medical device within 6 months before the planned first dose of study intervention or is currently enrolled in an investigational clinical study with an investigational intervention.
19. Female participants who are pregnant, or breast-feeding, or planning to become pregnant while enrolled in this study or within 90 days after the last dose of study intervention.
20. Male participants who plan to father a child while enrolled in this study or within 90 days after the last dose of study intervention.
21. Participants who had major surgery (e.g., requiring general anesthesia), excluding diagnostic surgery, within 12 weeks before screening, or will not have fully recovered from surgery, or have surgery planned during the time the participant is expected to participate in the study (Note: participants with planned surgical procedures to be conducted under local anesthesia may participate).
22. Participants who have received an organ transplant (except for skin, hair, or cornea transplant).
23. Participants who are employees of the investigator or study site, with direct involvement in the proposed study or other studies under the direction of that investigator or study site, or a family member of an employee or the investigator.
24. Vulnerable participants (e.g., incarcerated individual, individuals under a legal protection measure.
25. Participants with alcohol or drug abuse within 12 months of screening, judged by the investigator to likely interfere with clinical assessments.

Lifestyle Restrictions: Participants agree to follow all requirements outlined in Section Concomitant Therapy regarding prohibited and restricted therapy during the study. Participants agree to follow all requirements that must be met during the study, as noted in Inclusion Criteria and Exclusion Criteria (e.g., contraceptive requirements).

Population Sets: ITT=All participants who are randomized and receive at least 1 dose of study intervention. Safety=All participants who receive at least 1 dose of study intervention.

Statistical Methods: Statistical analyses is performed by the sponsor or under the supervision of the sponsor. A general description of the statistical methods to be used to analyze the efficacy, PK and safety data are outlined below. Specific details are provided in the Statistical Analysis Plan (SAP).

The primary analysis in this study is performed when all participants reached Week 48 or are discontinued earlier.

A final analysis (after the Week 48 follow-up phase) is performed when all participants reached the final study visit or are discontinued earlier.

Statistical Hypothesis: The primary hypothesis of this study is that the combination regimen of the RNAi component and nucleos(t)ide analog (NA) has superior efficacy compared to NA treatment alone in reducing the HDV replication and improving the associated liver inflammation, as measured by the primary efficacy endpoint at Week 48 (the proportion of participants with HDV RNA decline ≥2 $\log_{10}$ IU/mL from baseline or HDV RNA TND in combination with normal ALT).

Sample Size Determination: A total sample size of 125 participants (with ratio 4:1, 100 participants in Arm 1 and 25 in Arm 2) provide at least 95% power to detect a between-arm difference of ≥26% in the primary efficacy endpoint at Week 48, at a 1-sided Type 1 error rate of 0.05, assuming a 4% response rate in the deferred treatment (Arm 2). The assumed 4% response rate in the placebo+NA arm is a conservative estimate based on the results from NA treatment in previous studies.

Primary Efficacy Endpoint Analysis: The primary efficacy endpoint at Week 48 is compared between the 2 arms using the stratum-adjusted Mantel-Haenszel test on the difference of proportions, where the stratification factor of presence of compensated cirrhosis at screening (yes or no) determines the strata. The associated 90% confidence interval for the difference in proportions is also calculated. Participants with missing data for assessing the primary endpoint are considered non-responders for the purpose of the primary analysis. Sensitivity analyses is performed to assess alternative imputations.

Secondary and Exploratory Efficacy Analyses: Descriptive statistics are used for all efficacy endpoints, which are summarized by intervention arm as well as combining the RNAi component+NA data after the roll-over to active treatment in the deferred treatment arm.

Comparisons between intervention arms and corresponding 90% confidence intervals estimation are done with no adjustment for multiplicity. Specific selected endpoints may be analyzed using suitable categorical data approaches (eg, Cochran-Mantel-Haenszel or logistic regression for proportions or other categorical type of endpoint), longitudinal repeated measures models (e.g., for continuous types of variables), or survival analysis based on the Kaplan-Meier estimates (for time-to-event variables), as appropriate.

Patient-reported Outcome: Patient-reported outcome scores are analyzed descriptively as mean scores over time, and, if applicable, are evaluated based on the proportion of participants experiencing a clinically important improvement or worsening in PRO scores from baseline during study intervention and follow-up. Analyses is also performed on PRO score changes from baseline at specific time points (Week 48, 72, 96, 144, and EOS) and between Week 48 and later time points for different subgroups: participants with versus participants without HBsAg seroclearance 24 weeks and 48 weeks after completion of all study intervention at Week 144 (Arm 1) and Week 148 (Arm 2), and participants with versus participants without ≥2 $\log_{10}$ decline in HDV RNA or TND in combination with normal ALT at Week 48. Further details are provided in the SAP.

Safety analysis: Safety is evaluated by means of descriptive summaries of AEs including AEs of special interest to any of the study interventions, clinical laboratory tests, ECGs, vital signs, and physical examinations. The safety analysis is done by study phase. Results are presented in tabular format and/or graphically by intervention arm and over time, as appropriate.

PK analysis: Descriptive statistics (n, mean, SD, coefficient of variation [CV], geometric mean, median, minimum, and maximum) are calculated for the plasma concentrations of the RNAi component and optionally NA, as applicable, and for the derived plasma PK parameters.

For each participant with intensive PK sampling, plasma concentration-time data of the RNAi component, and, optionally, NA are graphically presented. Similarly, graphs of the mean plasma concentration time profiles and overlay graphs with combined individual plasma concentration time profiles are produced. Plasma PK parameters in participants undergoing intensive PK sampling are calculated via non-compartmental methods for the RNAi component, and, optionally, NA, as applicable. The PK parameters are $C_{max}$, $C_t$, and $AUC_{24h}$. The PK parameters are subjected to an exploratory graphical analysis, including various transformations, to get a general overview.

Special attention is paid to the plasma concentrations and PK parameters of those participants who discontinued the study for an AE, or who experienced an AE≥grade 3 or an SAE.

Population PK analysis of plasma concentration-time data of the RNAi component and, optionally, NA is performed using nonlinear mixed-effects modeling. Data may be combined with those from additional studies to support a relevant structural model. Available baseline characteristics (eg, demographics, laboratory variables, genotypes) are included in the model as necessary.

Individual estimates of PK parameters are generated from the population PK analysis for potential use in exposure response analysis. For operational reasons, a snapshot date for PK samples to be analyzed is defined, if required. Samples collected before this date are analyzed for the RNAi component and optionally NA and are included in the population PK analysis. Samples collected after the snapshot date are analyzed at a later date and may be included in a population PK re-analysis when they become available after database lock.

PK/PD analysis: Relationships of PK parameters for the RNAi component, and, optionally, NA with selected efficacy and with selected safety endpoints are evaluated and graphically displayed.

Modeling of key PD parameters (eg, HDV RNA, HBsAg) may be performed using population PK/PD. If PK/PD modeling of key efficacy endpoints is performed, treatment effect and possible covariates such as disease progression are investigated. Other biomarkers may be explored at the sponsor's discretion.

Resistance analysis: The results of HBV and potentially HDV viral sequencing are evaluated by the sponsor virologist. Relevant changes of amino acid and/or nucleic acid variations (e.g., substitutions) in the HBV genome are tabulated and described.

Additional exploratory characterization of the HBV viral sequence and phenotype may be performed and reported separately.

Immune Analyses: Descriptive statistics (n, mean, SD, CV, geometric mean, median, minimum, and maximum) are used to describe the magnitude of the IFN-γ T cell response or the CD4+ and CD8+ T-cell responses (expressing at least 1 cytokine such as IL-2, TNF-α or IFN-γ specific to any HBV antigen) as defined by ELISpot and/or ICS, respectively. Changes from baseline (if present) are also tabulated for PBMCs during study intervention and follow-up. The proportion (%) of CHB patients with positive responses based on the magnitude of the IFN-γ T cell response or the CD4+ or CD8+ T cells expressing at least 1 of the cytokines amongst IL-2, TNF-α or IFN-γ for 1 of the HBV antigens as defined by ELISpot and/or ICS, respectively, is determined.

Analyses is conducted at the sponsor's discretion.

Pharmacogenomic analysis: The statistical approach for analyzing the exploratory host DNA and RNA research, including epigenetic analyses, may depend on the objective of the analyses (efficacy, safety, and PK) and possibly relevant genes at the time of analysis. Analyses are conducted at the sponsor's discretion, are under the sponsor's supervision, and results are presented either in the clinical study report or a separate report.

Host Biomarkers Analyses: Statistical approaches to explore correlations between clinical outcome and blood biomarkers vary and depend on the different data types of the applied technology platforms, as well as on the extent of observed differences between participants. Analyses are conducted at the sponsor's discretion, are under the sponsor's supervision, and results are presented either in the clinical study report or a separate report.

Interim Analysis: Interim analyses (IAs) are conducted to assess safety and evaluate the time course of different disease markers to support the sponsor's interactions with health authorities, as well as to inform internal decisions about additional studies and/or investigation of other treatment combinations.

Interim analyses are planned when all participants have reached (1) Week 96, (2) Week 144 (Arm 1) and Week 148 (Arm 2) (end of treatment [EOT]), and (3) Week 168 (Follow-up Week 24) (or discontinued earlier).

One additional IA may be performed by the sponsor when all participants have reached Week 120 to support interactions with health authorities.

An IDMC is established for continuous monitoring of SAEs, AEs leading to discontinuation, and ALT flares. The IDMC also reviews the unblinded results of the efficacy parameters measured by different HDV and HBV disease blood markers (e.g., HDV RNA, HBV DNA, HBsAg, etc).

In addition, a futility analysis is conducted by the IDMC to assess whether there is early evidence supporting the conclusion of no robust HBsAg decline in the HBV/HDV co-infected population.

The IDMC accesses and uses the totality of unblinded results to make recommendations, including all safety and efficacy assessments available at a given interim milestone. Possible recommendations include, but are not limited to, stopping the study for futility or for safety concerns. The Sponsor Committee reviews the time course of the different disease blood markers to make further decisions. Decision rules are detailed and listed in the IDMC charter and are nonbinding.

In addition, an Independent Flare Expert Panel (iFLEP) is appointed.

Futility Analysis: A futility analysis is conducted by the IDMC to assess whether there is early evidence supporting the conclusion of no robust HBsAg decline in this HBV/HDV co-infected population. The futility criterion is defined in terms of the efficacy response as measured by a predefined threshold of HBsAg reduction from baseline. This futility analysis is nonbinding and the IDMC decides based on the whole package of information, which also includes other efficacy and safety assessments.

In case lack of HBsAg decline is concluded:

Enrollment in the study is stopped.

Participants already enrolled are switched to a treatment regimen at the discretion of the investigator.

In case no lack of HBsAg decline is concluded:

Ongoing enrollment continues.

Details of the futility analysis (including classification of lack of HBsAg decline) and criterion are included in the IDMC charter and SAP. The futility analysis is implemented through an IDMC, providing recommendations to a Sponsor Committee.

IDMC: Yes

TABLE 3

| Treatments | | | | | |
|---|---|---|---|---|---|
| Intervention Name | RNAi component | Placebo for RNAi component | Entecavir (ETV) monohydrate | Tenofovir disoproxil | Tenofovir alafenamide (TAF) |
| Type | Drug | | Drug | Drug | Drug |
| Dosage Formulation | Solution for injection | Solution for injection | Film-coated tablets | Film-coated tablets | Film-coated tablets |
| Unit Dose Strength | 200 mg/ml | 0.9% saline | 0.5 mg | 245 mg | 25 mg |
| Dosage Level | 100 mg once every 4 weeks (Q4W) | Q4W | Nucleoside-naïve participants: 0.5 mg qd Lamivudine-refractory participants: 1 mg[a] qd (but should preferably be treated with tenofovir disoproxil or TAF instead) | 245 mg qd | 25 mg qd |
| Route of Administration | Subcutaneous injection (in abdomen) | Subcutaneous injection (in abdomen) | Oral | Oral | Oral |
| Use | Investigational intervention | Investigational intervention | Background intervention | Background intervention | Background intervention |
| Investigational Medicinal Product (IMP and Non-investigational medicinal product | IMP | IMP | IMP | IMP | IMP |

TABLE 3-continued

| Treatments | | | | | |
|---|---|---|---|---|---|
| Intervention Name | RNAi component | Placebo for RNAi component | Entecavir (ETV) monohydrate | Tenofovir disoproxil | Tenofovir alafenamide (TAF) |
| (NIMP) | | | | | |
| Sourcing | Provided by Sponsor | Provided by Sponsor | Provided by Sponsor | Provided by Sponsor | Provided by Sponsor |
| Packaging and Labeling | Each unit labeled with unique medication ID number | Each unit labeled with unique medication ID number | Commercial supplies sourced and a clinical study label applied In child-resistant packaging | Commercial supplies sourced and a clinical study label applied In child-resistant packaging | Commercial supplies sourced and a clinical study label applied In child-resistant packaging |
| | Labels contain information to meet the applicable regulatory requirements | | | | |
| Food/Fasting Instructions | Regardless of food intake | Regardless of food intake | Per the prescribing information | Per the prescribing information | Per the prescribing information |

Q4W: once every 4 weeks;
qd: once daily
[a]2 tablets of 0.5 mg

Schedule of Activities (SOA)

TABLE 4

Schedule of Activities - Screening and Double-blind study intervention phase (first 52 weeks): Arm 1 and Arm 2. For participants of Arm 1, assessments from week 52 until week 144 are described in Table 5. For participants of Arm 2, assessments from week 52 until week 144 are described in Table 6.

| | Study Phase | | | | | | | | | | | | | | |
|---|---|---|---|---|---|---|---|---|---|---|---|---|---|---|---|
| | Scr. | Double-Blind Study Intervention Visit Day (D)/Week (W) | | | | | | | | | | | | | |
| | W-4 to 0[b] | D1[c] | W2 | W4 | W8 | W12 | W16 | W20 | W24 | W28 | W32 | W36 | W40 | W44 | W48/ WD[a] |
| | Study Day (Window) | | | | | | | | | | | | | | |
| | −28 | 1 | 15 ± 2 | 29 ± 2 | 57 ± 2 | 85 ± 2 | 113 ± 3 | 141 ± 3 | 169 ± 3 | 197 ± 3 | 225 ± 3 | 253 ± 3 | 281 ± 3 | 309 ± 3 | 337 ± 3 |
| Screening/ Admin. | | | | | | | | | | | | | | | |
| ICF[d] | X | | | | | | | | | | | | | | |
| ICF for opt pharmacogenomic samp | X | | | | | | | | | | | | | | |
| Incl/Excl criteria[e] | X | | | | | | | | | | | | | | |
| Prestudy therapy (including prior anti-HBV therapy) | X | | | | | | | | | | | | | | |
| Medical/surg. hist. and demographics[f] | X | | | | | | | | | | | | | | |
| Preplanned surg/proced. | X | | | | | | | | | | | | | | |
| Fibroscan or liver biopsy[g] | X | | | | | | | | | | | | | | X |
| HLA testing | X | | | | | | | | | | | | | | |
| Abdominal ultrasound[h] | X | | | | | | | | | | | | | | |
| Serum IgM anti-HBc antibody test | X | | | | | | | | | | | | | | |
| Serum IgG anti-HDV antibody test | X | | | | | | | | | | | | | | |
| Testing for hepatitis A, B, | X | | | | | | | | | | | | | | |

TABLE 4-continued

Schedule of Activities - Screening and Double-blind study intervention phase (first 52 weeks): Arm 1 and Arm 2. For participants of Arm 1, assessments from week 52 until week 144 are described in Table 5. For participants of Arm 2, assessments from week 52 until week 144 are described in Table 6.

| | Study Phase | | | | | | | | | | | | | | |
|---|---|---|---|---|---|---|---|---|---|---|---|---|---|---|---|
| | Scr. | Double-Blind Study Intervention Visit Day (D)/Week (W) | | | | | | | | | | | | | |
| | W-4 to 0[b] | D1[c] | W2 | W4 | W8 | W12 | W16 | W20 | W24 | W28 | W32 | W36 | W40 | W44 | W48/ WD[a] |
| | Study Day (Window) | | | | | | | | | | | | | | |
| | −28 | 1 | 15 ± 2 | 29 ± 2 | 57 ± 2 | 85 ± 2 | 113 ± 3 | 141 ± 3 | 169 ± 3 | 197 ± 3 | 225 ± 3 | 253 ± 3 | 281 ± 3 | 309 ± 3 | 337 ± 3 |
| C, D, and E virus, HIV-1, HIV-2 | | | | | | | | | | | | | | | |
| FSH test (postmenopaus. women only)[k] | X | | | | | | | | | | | | | | |
| AFP | X | | | | | | | | | | | | | | |
| Hemoglobin A1c test | X | | | | | | | | | | | | | | |
| Serum pregnancy test (women of childbearing potential only) | X | | | | | | | | | | | | | | |
| HBV genotype[i] | | X | | | | | | | | | | | | | |
| HDV genotype[j] | | X | | | | | | | | | | | | | |
| Study Intervention Admin. | | | | | | | | | | | | | | | |
| Randomization | | X | | | | | | | | | | | | | |
| Administer RNAi component or placebo | | X | | X | X | X | X | X | X | X | X | X | X | X | (X) |
| Dispense NA | | X | | X | X | X | X | X | X | X | X | X | X | X | (X) |
| Intake of NA[l] | | X | X | X | X | X | X | X | X | X | X | X | X | X | (X) |
| NA accountability | | | X | X | X | X | X | X | X | X | X | X | X | X | X |
| Safety Evaluations | | | | | | | | | | | | | | | |
| Complete physical examination[m] | X | | | | | | | | | | | | | | X |
| Symptom-directed physical examination[o] | | X | X | X | X | X | X | X | X | X | X | X | X | X | |
| Liver ultrasound[n] | | X | | | | | | | X | | | | | | X |
| Vital signs[p] | X | X | X | X | X | X | X | X | X | X | X | X | X | X | X |
| Triplicate 12-lead ECG[q] | X | X | | X | | X | | | X | | | X | | | X |
| Injection site reactions | | | X | X | X | X | X | X | X | X | X | X | X | X | X |
| Clinical Laboratory Tests | | | | | | | | | | | | | | | |
| Hematology | X | X | X | X | X | X | X | X | X | X | X | X | X | X | X |
| Blood chemistry (including liver function)[r,s,t] | X | X | X | X | X | X | X | X | X | X | X | X | X | X | X |
| Blood coagulation | X | X | X | X | X | X | X | X | X | X | X | X | X | X | X |
| Urinalysis and urine chem.[u] | X | X | | X | X | X | X | X | X | X | X | X | X | X | X |

TABLE 4-continued

Schedule of Activities - Screening and Double-blind study intervention phase (first 52 weeks): Arm 1 and Arm 2. For participants of Arm 1, assessments from week 52 until week 144 are described in Table 5. For participants of Arm 2, assessments from week 52 until week 144 are described in Table 6.

| | Study Phase | | | | | | | | | | | | | | |
|---|---|---|---|---|---|---|---|---|---|---|---|---|---|---|---|
| | Scr. | Double-Blind Study Intervention Visit Day (D)/Week (W) | | | | | | | | | | | | | |
| | W-4 to 0[b] | D1[c] | W2 | W4 | W8 | W12 | W16 | W20 | W24 | W28 | W32 | W36 | W40 | W44 | W48/ WD[a] |
| | Study Day (Window) | | | | | | | | | | | | | | |
| | −28 | 1 | 15 ± 2 | 29 ± 2 | 57 ± 2 | 85 ± 2 | 113 ± 3 | 141 ± 3 | 169 ± 3 | 197 ± 3 | 225 ± 3 | 253 ± 3 | 281 ± 3 | 309 ± 3 | 337 ± 3 |
| Urine pregnancy test (women of childbearing potential) | | X | | X | X | X | X | X | X | X | X | X | X | X | X |
| Efficacy Evaluations | | | | | | | | | | | | | | | |
| Fibroscan | | X[v,w] | | | | | | | | | | | | | X[w] |
| HBV and HDV virology | | | | | | | | | | | | | | | |
| Blood sampling for HBV DNA and HDV RNA | X | X | X | X | X | X | X | X | X | X | X | X | X | X | X |
| Blood sampling for HBV RNA[x] | X | X | X | | X | X | | | X | | | X | | | X |
| Sampling for viral genome sequencing[y] | X | X | | | | X | | | X | | | X | | | X |
| HBV serology | | | | | | | | | | | | | | | |
| Blood sample for: | X | | | | | | | | | | | | | | |
| Anti-HBs (quantitative) and anti-HBe | X | | | | | | | | X | | | | | | X |
| HBsAg and HBeAg (qualitative) | X | | | | | | | | X | | | | | | X |
| HBsAg (quantitative) | X | X | X | X | X | X | X | X | X | X | X | X | X | X | X |
| HBeAg[z] | X | X | X | X | | X | | | X | | | X | | | X |
| HBcrAg[x] | X | X | X | X | | X | | | X | | | X | | | X |
| Exploratory serology[aa] | X | X | X | X | X | X | | | X | | | X | | | X |
| Pharmaco-kinetics | | | | | | | | | | | | | | | |
| Blood sampling for sparse PK of RNAi component and optionally NA[bb] | | X[cc] | | X[cc] | | X[cc] | | | X[cc] | | | | | | X[cc] |
| Blood sampling for intensive PK of RNAi component and opt. NA (PK subgroup)[dd] | | | | X[cc] | | | | | | | | | | | |
| Exploratory Biomarkers | | | | | | | | | | | | | | | |
| Whole blood RNA gene expression | | X | | | | X | | | X | | | | | | X |
| Whole blood single cell profiling | | X | | X | X | X | | | X | | X | | X | | X |
| Host serum proteins (e.g., cytokines) | | X | X | X | X | X | | | X | | X | | X | | X |

TABLE 4-continued

Schedule of Activities - Screening and Double-blind study intervention phase (first 52 weeks): Arm 1 and Arm 2. For participants of Arm 1, assessments from week 52 until week 144 are described in Table 5. For participants of Arm 2, assessments from week 52 until week 144 are described in Table 6.

| | Study Phase | | | | | | | | | | | | | | |
|---|---|---|---|---|---|---|---|---|---|---|---|---|---|---|---|
| | Scr. | Double-Blind Study Intervention Visit Day (D)/Week (W) | | | | | | | | | | | | | |
| | W-4 to 0[b] | D1[c] | W2 | W4 | W8 | W12 | W16 | W20 | W24 | W28 | W32 | W36 | W40 | W44 | W48/ WD[a] |
| | Study Day (Window) | | | | | | | | | | | | | | |
| | −28 | 1 | 15 ± 2 | 29 ± 2 | 57 ± 2 | 85 ± 2 | 113 ± 3 | 141 ± 3 | 169 ± 3 | 197 ± 3 | 225 ± 3 | 253 ± 3 | 281 ± 3 | 309 ± 3 | 337 ± 3 |
| Antidrug antibodies (to RNAi component) | | X | | | | | | | X | | | | | | X |
| Immune monitoring | | | | | | | | | | | | | | | |
| Immune cells (PBMCs) selected sites only | | X | | | | | | | X | | | | | | X |
| Pharmacogenomics (DNA) | | | | | | | | | | | | | | | |
| Exploratory host genotyping (optional)[gg] | | X | | | | | | | | | | | | | |
| Epigenetics | | X | | | | | | | X | | | | | | X |
| PRO Evaluations[hh] | | | | | | | | | | | | | | | |
| HBQOL | | X | | | | X | | | X | | | X | | | X |
| SF-36v2 | | X | | | | X | | | X | | | X | | | X |
| EQ-5D-5L | | X | | | | X | | | X | | | X | | | X |
| Ongoing participant review | | | | | | | | | | | | | | | |
| Concomitant therapy | X | X | X | X | X | X | X | X | X | X | X | X | X | X | X |
| Adverse Events | X | X | X | X | X | X | X | X | X | X | X | X | X | X | X |

General Note: The PRO assessments are preferably completed before any tests, procedures or other consultations for that visit to prevent influencing the participant's perceptions. AFP: alpha-fetoprotein; ALP: alkaline phosphatase; ALT: alanine aminotransferase; AST: aspartate aminotransferase; CKD-EPI: Chronic Kidney Disease Epidemiology Collaboration; CRF: case report form; CT: computed tomography; D/d: Day/days; DBP: diastolic blood pressure; DNA: deoxyribonucleic acid; ECG: electrocardiogram; eGFR: estimated glomerular filtration rate; FSH: follicle-stimulating hormone; HBc: hepatitis B core protein; HBe(Ag): hepatitis B e (antigen); HBcrAg: hepatitis B core-related antigen; HBQOL: Hepatitis B Quality of Life; HBs(Ag): hepatitis B surface (antigen); HBV: hepatitis B virus; HCC hepatocellular carcinoma; HDV: hepatitis D virus; HIV-1 (-2): human immunodeficiency virus type 1 (type 2); ICF: informed consent form; IgG: immunoglobulin G; IgM: immunoglobulin M; IWRS: interactive web response system; MRI: magnetic resonance imaging; NA: nucleos(t)ide analog; PBMC: peripheral blood mononuclear cells; PGIC: patient global impression of change; PK: pharmacokinetic; PRO: patient-reported outcome; RNA: ribonucleic acid; SBP: systolic blood pressure; ULN: upper limit of normal; W: Week.

a. Participants who discontinue RNAi component early have an early WD visit and enter follow-up unless they withdraw consent/assent. Participants who withdraw consent/assent are offered an optional safety follow-up visit.

b. If necessary (e.g., for operational reasons), the screening phase is extended up to a maximum of 6 weeks in agreement with the sponsor.

c. Day 1 samples are collected before the first dose of study intervention.

d. The ICF is signed before the first study-related activity.

e. Minimum criteria for the availability of documentation supporting the eligibility criteria are described in the protocol. Clinical status is checked at screening and again before first dose of study intervention. If a participant's clinical status changes (including any available laboratory results or receipt of additional medical records that becomes available during the screening phase) after screening but before the first dose of study intervention is given such that he or she no longer meets all eligibility criteria, then the participant is excluded from participation in the study.

f. Medical history also includes mode of HBV and HDV transmission and stage of liver fibrosis. Historical HDV RNA, anti-HDV antibodies, and HBV DNA are reported in the CRF. HBsAg, HBeAg and ALT data, if available, are recorded in Source docs, but not in the CRF.

g. Liver disease staging assessments are performed based on Fibroscan or liver biopsy results, obtained within 6 months (in case of Fibroscan) or within 1 year (in case of liver biopsy) prior to screening or at the time of screening.

h. Participants have absence of signs of HCC or clinically relevant renal abnormalities on an abdominal ultrasound performed within 6 months prior to screening or at the time of screening. In case of suspicious findings on conventional ultrasound the participant are still eligible if HCC or clinically relevant renal abnormalities are ruled out by a more specific imaging procedure (contrast enhanced ultrasound, CT or MRI).

i. HBV genotype is determined at baseline using standard genotyping assay if HBV DNA levels are sufficiently high. For participants with low HBV DNA levels, available historical data on previous HBV genotype assessment are collected in the CRF. Exploratory genotyping assays might be performed.

j. HDV genotype is determined by sequencing. For participants with low HDV RNA levels, available historical data on previous HDV genotype assessment is collected in the CRF. Exploratory genotyping assays might be performed.

k. For postmenopausal women only: an FSH level in the postmenopausal range is used to confirm a postmenopausal state in women not using hormonal contraception or hormonal replacement therapy. However, in the absence of 12 months of amenorrhea, a single FSH measurement is insufficient to confirm a woman is not of childbearing potential.

l. In between study visits, participants take NA at home and they bring their NA with them to each study visit.

m. Complete physical examination, including height (at screening only), body weight, skin examination, and other body systems.

n. A liver ultrasound is performed every 24 weeks from Day 1 for HCC screening in all participants.

o. Symptom-directed physical examination, including body weight.

p. Vital signs include supine SBP, DBP, pulse rate, and body temperature.

q. All ECGs are read centrally. On Day 1, pre-dose ECG assessment is done locally on site to determine eligibility.

r. Biochemistry samples are taken after fasting for at least 10 hours for measurement of phosphate, calcium, creatinine, and lipids.

s. Creatinine clearance (eGFR calculated by the CKD-EPI formula) is assessed.

t. Intervention-emergent ALT/AST elevations (i.e., ALT and/or AST≥3×ULN and ≥3× nadir [i.e., lowest value during study participation]), triggers an assessment of confounding factors (alcohol intake, change in concomitant medication, and comorbidities). Participants are also required to come for weekly visits until ALT and/or AST levels have returned to 50% of the maximal value and, if present, liver-related symptoms improve. At a minimum, the following blood chemistry parameters are assessed in the central laboratory at these weekly visits: ALT, AST, ALP, bilirubin (total and direct), albumin, coagulation, and HBV DNA.

u. Urine chemistry sample (quantitative measurement): creatinine, sodium, phosphate, glucose, protein, and albumin. Urinalysis by dipstick: specific gravity, pH, glucose, protein, blood, ketones, bilirubin, urobilinogen, nitrite, leukocyte esterase, and microscopic analysis if needed. In case of a positive dipstick result, a urine sample is set aside for additional examination of the positive parameter at the central laboratory (e.g., quantification as applicable).

v. Only applicable to participants who are enrolled at a site with an on-site Fibroscan device.

w. A Fibroscan assessment is only done at baseline if it was not done at screening.

x. HBcrAg and HBV RNA samples may be batched and only selected samples may be tested at the sponsor's discretion. Samples can be used for assessment of other serologic/virologic markers of HBV and HDV.

y. Sequencing at baseline (Day 1 predose) is performed by default if HBV DNA levels and HDV RNA levels are within the ranges required for the sequencing assay; other samples may be sequenced based on the sponsor virologist's request.

z. Quantitative HBeAg assessment is only performed in participants who are defined HBeAg-positive at screening based on a qualitative HBeAg assay.

aa. Exploratory serology samples may be analyzed at the sponsor's discretion. Samples may be used to assess virologic or serologic markers of HBV.

bb. All participants have sparse PK sampling. For all samples, the time of the preceding 2 intakes of NA and the time of PK sampling is recorded.

cc. One sample at any time between 2 and 8 hours after RNAi component dosing with collection of the time interval between last administration and blood draw. Before leaving the study site, the participant's wellbeing is confirmed.

dd. All participants who consent to participate in the intensive PK subgroup (optional) undergo intensive PK sampling at Week 4. If necessary (eg, for operational reasons), this visit may be scheduled at Week 8, 12, or 16. The study intervention is taken on site and time of dosing is recorded. Pharmacokinetic samples are taken predose and 15 minutes, 30 minutes, 1, 2, 3, 4, 6, 8,* 10,* and 24 hours post-dose (*the 8 and 10 hours postdose samples are optional). All efforts are made to obtain the PK samples at the exact nominal time relative to dosing. However, samples obtained within 20% of the nominal time from dosing (e.g., within 12 minutes of a 60-minute time point) are not captured as a protocol deviation if the exact time of the sample collection is noted on the source document and CRF.

ee. Sparse PK sampling is not required if the participant is part of the intensive PK subgroup and has an intensive PK sampling at the same visit.

ff. PBMC samples are collected at selected sites only. Additional PBMC samples may be taken in case of ALT flares, upon discussion with the sponsor, which may require an unscheduled visit.

gg. The pharmacogenomic (DNA) sample is preferably collected at baseline. This sample is optional and is only collected from participants who consent separately to this component of the study.

hh. PRO assessments are performed by participants at sites where appropriate translations are available.

TABLE 5

Schedule of Activities - Open-label Study Intervention Phase (Weeks 52-144): Arm 1. After Week 144 (or early discontinuation) visit, participants of Arm 1 enter the follow-up phase.

| | Study Phase Open-label Visit Day (D)/Week (W) | | | | | | | | | | | |
|---|---|---|---|---|---|---|---|---|---|---|---|---|
| | W52 | W56 | W60 | W64 | W68 | W72 | W76 | W80 | W84 | W88 | W92 | W96 |
| | Study Day (Window) | | | | | | | | | | | |
| | 365 ± 1 w | 393 ± 1 w | 421 ± 1 w | 449 ± 1 w | 477 ± 1 w | 505 ± 1 w | 533 ± 1 w | 561 ± 1 w | 589 ± 1 w | 617 ± 1 w | 645 ± 1 w | 673 ± 1 w |
| Study Intervention Admin. | | | | | | | | | | | | |
| Administer RNAi component | X | X | X | X | X | X | X | X | X | X | X | X |
| Dispense NA | X | X | X | X | X | X | X | X | X | X | X | X |
| Intake of NA[b] | X | X | X | X | X | X | X | X | X | X | X | X |
| NA accountability | X | X | X | X | X | X | X | X | X | X | X | X |
| Safety Evaluations | | | | | | | | | | | | |
| Symptom-directed physical examination[e] | X | X | X | X | X | X | X | X | X | X | X | X |
| Liver ultrasound[d] | | | | | | X | | | | | | X |
| Vital signs[f] | X | X | X | X | X | X | X | X | X | X | X | X |
| Triplicate 12-lead ECG[g] | | | X | | | X | | | X | | | X |
| Injection site reactions | X | X | X | X | X | X | X | X | X | X | X | X |
| Clinical Laboratory Tests | | | | | | | | | | | | |
| Hematology | X | X | X | X | X | X | X | X | X | X | X | X |
| Blood chemistry (including liver function tests)[h,i,j] | | | X | | | X | | | X | | | X |
| Blood coagulation | | | X | | | X | | | X | | | X |
| Urinalysis and urine chem.[k] | | | X | | | X | | | X | | | X |
| Urine pregnancy test (women of childbearing potential) | X | X | X | X | X | X | X | X | X | X | X | X |
| Efficacy Evaluations | | | | | | | | | | | | |
| Fibroscan | | | | | | | | | | | | |
| HBV and HDV virology | | | | | | | | | | | | |
| Blood sampling for HBV DNA and HDV RNA | X | X | X | X | X | X | X | X | X | X | X | X |
| Blood sampling for HBV RNA[m] | | | X | | | X | | | X | | | X |
| Sampling for viral genome sequencing[n] | | | X | | | X | | | X | | | X |
| HBV serology | | | | | | | | | | | | |
| Blood sampling for: | | | | | | | | | | | | |
| Anti-BBs and anti-HBe | | | | | | X | | | | | | X |
| HBsAg and HBeAg (qualitative) | | | | | | X | | | | | | X |
| HBsAg (quantitative) | X | X | X | X | X | X | X | X | X | X | X | X |
| HBeAg[o] (quantitative) | | | X | | | X | | | X | | | X |
| HBcrAgphu l | | | X | | | X | | | X | | | X |
| Exploratory serology[p] | | | X | | | X | | | X | | | X |
| Pharmaco-kinetics | | | | | | | | | | | | |
| Blood sampling for sparse PK of RNAi component and optionally NA[q] | X[r] | X[r] | | X[r] | | | X[r] | | | | | |
| Blood sampling for intensive PK of RNAi component and opt. | X[t] | | | | | | | | | | | |

TABLE 5-continued

Schedule of Activities - Open-label Study Intervention Phase (Weeks 52-144): Arm 1. After Week 144 (or early discontinuation) visit, participants of Arm 1 enter the follow-up phase.

| | Study Phase Open-label Visit Day (D)/Week (W) | | | | | | | | | | | |
|---|---|---|---|---|---|---|---|---|---|---|---|---|
| | W100 | W104 | W108 | W112 | W116 | W120 | W124 | W128 | W132 | W136 | W140 | W144/ WD[a] |
| | Study Day (Window) | | | | | | | | | | | |
| | 701 ± 1 w | 729 ± 1 w | 1 w | 785 ± 1 w | 813 ± 1 w | 841 ± 1 w | 869 ± 1 w | 897 ± 1 w | 925 ± 1 w | 953 ± 1w | 981 ± 1 w | 1009 ± 1 w |
| NA (PK subgroup)[s] | | | | | | | | | | | | |
| Exploratory Biomarkers | | | | | | | | | | | | |
| Whole blood RNA gene expression | | | | | | | | | | | | X |
| Whole blood single cell profiling | | | | | | | | | | | | X |
| Host serum proteins (e.g., cytokines) | | | | | | | | | | | | X |
| Antidrug antibodies (to RNAi component) | | | | | | X | | | | | | X |
| Immune monitoring | | | | | | | | | | | | |
| Immune cells (PBMCs) selected sites only[u] | | | | | | | | | | | | X |
| Pharmacogenomics (DNA) | | | | | | | | | | | | X |
| Epigenetics | | | | | | | | | | | | |
| PRO Evaluations[v] | | | | | | | | | | | | |
| HBQOL | | | X | | | X | | | X | | | X |
| SF-36v2 | | | X | | | X | | | X | | | X |
| EQ-5D-5L | | | X | | | X | | | X | | | X |
| Ongoing participant review | | | | | | | | | | | | |
| Concomitant therapy | X | X | X | X | X | X | X | X | X | X | X | X |
| Adverse Events | X | X | X | X | X | X | X | X | X | X | X | X |
| Study Intervention Admin. | | | | | | | | | | | | |
| Administer RNAi component | X | X | X | X | X | X | X | X | X | X | X | |
| Dispense NA | X | X | X | X | X | X | X | X | X | X | X | (X)[c] |
| Intake of NA[b] | X | X | X | X | X | X | X | X | X | X | X | (X) |
| NA accountability | X | X | X | X | X | X | X | X | X | X | X | (X) |
| Safety Evaluations | | | | | | | | | | | | |
| Symptom-directed X physical examination[e] | X | X | X | X | X | X | X | X | X | X | X | |
| Liver ultrasound[d] | | | | | | X | | | | | | X |
| Vital signs[f] | X | X | X | X | X | X | X | X | X | X | X | X |
| Triplicate 12-lead ECG[g] | | | X | | | X | | | X | | | X |
| Injection site reactions | X | X | X | X | X | X | X | X | X | X | X | X |
| Clinical Laboratory Tests | | | | | | | | | | | | |
| Hematology | X | X | X | X | X | X | X | X | X | X | X | X |
| Blood chemistry (including liver function tests)[h,i,j] | | | X | | | X | | | X | | | X |
| Blood coagulation | | | X | | | X | | | X | | | X |
| Urinalysis and urine chem.[k] | | | X | | | X | | | X | | | X |
| Urine pregnancy test (women of childbearing potential) | X | X | X | X | X | X | X | X | X | X | X | X |

TABLE 5-continued

Schedule of Activities - Open-label Study Intervention Phase (Weeks 52-144): Arm 1. After Week 144 (or early discontinuation) visit, participants of Arm 1 enter the follow-up phase.

| | | | | | | | | | | | | |
|---|---|---|---|---|---|---|---|---|---|---|---|---|
| Efficacy Evaluations | | | | | | | | | | | | |
| Fibroscan | | | | | | | | | | | | X |
| HBV and HDV virology | | | | | | | | | | | | |
| Blood sampling for HBV DNA and HDV RNA | X | X | X | X | X | X | X | X | X | X | X | X |
| Blood sampling for HBV RNA[m] | | | X | | | X | | | X | | | X |
| Sampling for viral genome sequencing’ | | | X | | | X | | | X | | | X |
| HBV serology | | | | | | | | | | | | |
| Blood sampling for: | | | | | | | | | | | | |
| Anti-BBs and anti-HBe | | | | | | X | | | | | | X |
| HBsAg and HBeAg (qualitative) | | | | | | X | | | | | | X |
| HBsAg (quantitative) | X | X | X | X | X | X | X | X | X | X | X | X |
| HBeAg[o] (quantitative) | | | X | | | X | | | X | | | X |
| HBcrAg[l] | | | X | | | X | | | X | | | X |
| Exploratory serology[p] | | | X | | | X | | | X | | | X |
| Pharmaco-kinetics | | | | | | | | | | | | |
| Blood sampling for sparse PK of RNAi component and optionally NA[q] | X[r] | | | | | | | | | | | |
| Blood sampling for intensive PK of RNAi component and opt. NA (PK subgroup)[s] | | | | | | | | | | | | |
| Exploratory Biomarkers | | | | | | | | | | | | |
| Whole blood RNA gene expression | | | | | | | | | | | | X |
| Whole blood single cell profiling | | | | | | | | | | | | X |
| Host serum proteins (e.g., cytokines) | | | | | | | | | | | | X |
| Antidrug antibodies (to RNAi component) | | | | | | X | | | | | | X |
| Immune monitoring | | | | | | | | | | | | |
| Immune cells (PBMCs) selected sites only[u] | | | | | | | | | | | | X |
| Pharmacogenomics (DNA) | | | | | | | | | | | | |
| Epigenetics | | | | | | | | | | | | X |
| PRO Evaluations[v] | | | | | | | | | | | | |
| HBQOL | | | X | | | X | | | X | | | X |
| SF-36v2 | | | X | | | X | | | X | | | X |
| EQ-5D-5L | | | X | | | X | | | X | | | X |
| Ongoing participant review | | | | | | | | | | | | |
| Concomitant therapy | X | X | X | X | X | X | X | X | X | X | X | X |
| Adverse Events | X | X | X | X | X | X | X | X | X | X | X | X |

General Note: The PRO assessments are preferably completed before any tests, procedures or other consultations for that visit to prevent influencing the participant's perceptions.

AFP: alpha-fetoprotein; ALP: alkaline phosphatase; ALT: alanine aminotransferase; AST: aspartate aminotransferase; CKD-EPI: Chronic Kidney Disease Epidemiology Collaboration; CRF: case report form; CT: computed tomography; D/d: Day/days; DBP: diastolic blood pressure; DNA: deoxyribonucleic acid; ECG: electrocardiogram; eGFR: estimated glomerular filtration rate; FSH: follicle-stimulating hormone; HBc: hepatitis B core protein; HBe(Ag): hepatitis B e (antigen); HBcrAg: hepatitis B core-related antigen; HBQOL: Hepatitis B Quality of Life; HBs(Ag): hepatitis B surface (antigen); HBV: hepatitis B virus; HCC hepatocellular carcinoma; HDV: hepatitis D virus; HIV-1 (-2): human immunodeficiency virus type 1 (type 2); ICF: informed consent form; IgM: immunoglobulin M; IWRS: interactive web response system; MRI: magnetic resonance imaging; NA: nucleos(t)ide analog; PBMC: peripheral blood mononuclear cells; PGIC: patient global impression of change; PK: pharmacokinetic; PRO: patient-reported outcome; RNA: ribonucleic acid; SBP: systolic blood pressure; ULN: upper limit of normal; W: Week; WD: withdrawal.

a. Participants who discontinue RNAi component early have an early WD visit and enter follow-up unless they withdraw consent/assent. Participants who withdraw consent/assent are offered an optional safety follow-up visit.

b. In between study visits, participants take NA at home and they bring their NA with them to each study visit.

c. NA continues to be dispensed at and after Week 144 for participants without cirrhosis at the investigator's discretion and for participants with cirrhosis.

d. A liver ultrasound is performed every 24 weeks from Day 1 for HCC screening in all participants.

e. Symptom-directed physical examination, including body weight.

f. Vital signs include supine SBP, DBP, pulse rate, and body temperature.

g. All ECGs are read centrally.

h. Biochemistry samples are taken after fasting for at least 10 hours for measurement of phosphate, calcium, creatinine, and lipids.

i. Creatinine clearance (eGFR calculated by the CKD-EPI formula) is assessed.

j. Intervention-emergent ALT/AST elevations (i.e., ALT and/or AST≥3×ULN and ≥3× nadir [i.e., lowest value during study participation]), triggers an assessment of confounding factors (alcohol intake, change in concomitant medication, and comorbidities). Participants are required to come for weekly visits until ALT and/or AST levels have returned to 50% of the maximal value and, if present, liver-related symptoms have improved. At a minimum, the following blood chemistry parameters are assessed in the central laboratory at these weekly visits: ALT, AST, ALP, bilirubin (total and direct), albumin, coagulation, and HBV DNA.

k. Urine chemistry sample (quantitative measurement): creatinine, sodium, phosphate, glucose, protein, and albumin. Urinalysis by dipstick: specific gravity, pH, glucose, protein, blood, ketones, bilirubin, urobilinogen, nitrite, leukocyte esterase, and microscopic analysis if needed. In case of a positive dipstick result, a urine sample is set aside for additional examination of the positive parameter at the central laboratory (eg, quantification as applicable).

l. Only applicable to participants who are enrolled at a site with an on-site Fibroscan device.

m. HBcrAg and HBV RNA samples may be batched and only selected samples may be tested at the sponsor's discretion. Samples can be used for assessment of other serologic/virologic markers of HBV and HDV.

n. Samples may be sequenced based on the sponsor virologist's request.

o. Quantitative HBeAg assessment is only performed in participants who are defined HBeAg-positive at screening based on a qualitative HBeAg assay.

p. Exploratory serology samples may be analyzed at the sponsor's discretion. Samples may be used to assess virologic or serologic markers of HBV.

q. All participants have sparse PK sampling. For all samples, the time of the preceding 2 intakes of NA and the time of PK sampling is recorded.

r. One sample at any time between 2 and 8 hours after RNAi component dosing with collection of the time interval between last administration and blood draw. Before leaving the study site, the participant's wellbeing is confirmed.

s. All participants who consent to participate in the intensive PK subgroup (optional) undergo intensive PK sampling at Week 52. If necessary (e.g., for operational reasons), this visit may be scheduled at Week 56, 60, or 64. The study intervention is taken on site and time of dosing is recorded. Pharmacokinetic samples are taken predose and 15 minutes, 30 minutes, 1, 2, 3, 4, 6, 8,* 10,* and 24 hours postdose (*the 8 and 10 hours postdose samples are optional). All efforts are made to obtain the PK samples at the exact nominal time relative to dosing. However, samples obtained within 20% of the nominal time from dosing (e.g., within 12 minutes of a 60-minute time point) are not captured as a protocol deviation if the exact time of the sample collection is noted on the source document and CRF.

t. Sparse PK sampling is not required if the participant is part of the intensive PK subgroup and has an intensive PK sampling at the same visit.

u. PBMC samples are collected at selected sites only. Additional PBMC samples may be taken in case of ALT flares, upon discussion with the sponsor, which may require an unscheduled visit.

v. PRO assessments are performed by participants at sites where appropriate translations are available.

TABLE 6

Schedule of Activities - Open-label Study Intervention Phase (Weeks 52-148): Arm 2. After Week 148 (or early discontinuation) visit, participants of Arm 2 enter the follow-up phase.

| | Study Phase Open-label Visit Day (D)/Week (W) | | | | | | | | | | | | | |
|---|---|---|---|---|---|---|---|---|---|---|---|---|---|---|
| | W52 | W54 | W56 | W60 | W64 | W68 | W72 | W76 | W80 | W84 | W88 | W92 | W96 | W100 |
| | Study Day (Window) | | | | | | | | | | | | | |
| | 365 ± 3 d | 379 ± 3 d | 393 ± 1 w | 421 ± 1 w | 449 ± 1 w | 477 ± 1 w | 505 ± 1 w | 533 ± 1 w | 561 ± 1 w | 589 ± 1 w | 617 ± 1 w | 645 ± 1 w | 673 ± 1 w | 701 ± 1 w |
| Study Intervention Admin. | | | | | | | | | | | | | | |
| Administer RNAi component | X | | X | X | X | X | X | X | X | X | X | X | X | X |
| Dispense NA | X | | X | X | X | X | X | X | X | X | X | X | X | X |
| Intake of NA[b] | X | X | X | X | X | X | X | X | X | X | X | X | X | X |
| NA accountability | X | X | X | X | X | X | X | X | X | X | X | X | X | X |
| Safety Evaluations | | | | | | | | | | | | | | |
| Symptom-directed physical examination[e] | X | X | X | X | X | X | X | X | X | X | X | X | X | X |
| Liver ultrasound[d] | | | | | | | | X | | | | | | X |
| Vital signs[f] | X | X | X | X | X | X | X | X | X | X | X | X | X | X |
| Triplicate 12-lead ECG[g] | X | | X | | X | | | X | | | X | | | X |
| Injection site reactions | X | X | X | X | X | X | X | X | X | X | X | X | X | x |
| Clinical Laboratory Tests | | | | | | | | | | | | | | |
| Hematology | X | X | X | X | X | X | X | X | X | X | X | X | X | X |
| Blood chemistry (including liver function tests)[h,i,j] | X | X | X | X | X | X | X | X | X | X | X | X | X | X |
| Blood coagulation | X | X | X | X | X | X | X | X | X | X | X | X | X | X |
| Urinalysis and X urine chem.[k] | X | X | X | X | X | X | X | X | X | X | X | X | | |
| Urine pregnancy test (women of childbearing potential) | X | X | X | X | X | X | X | X | X | X | X | X | X | X |
| Efficacy Evaluations | | | | | | | | | | | | | | |
| Fibroscan | | | | | | | | | | | | | | |
| HBV and HDV virology | | | | | | | | | | | | | | |
| Blood sampling for HBV DNA and HDV RNA | X | X | X | X | X | X | X | X | X | X | X | X | X | X |
| Blood sampling for HBV RNAm | X | X | | X | X | | | X | | | X | | | X |
| Sampling for viral genome sequencing[n] | X | | | | X | | | X | | | X | | | X |
| HBV serology Blood sampling for: | | | | | | | | | | | | | | |
| Anti-HBs and anti-HBe | X | | | | | | | X | | | | | | X |
| HBsAg and HBeAg (qual.) | | | | | | | | X | | | | | | X |
| HBsAg (quant.) | X | X | X | X | X | X | X | X | X | X | X | X | X | X |
| HBeAg[o] (quant.) X | X | X | | X | | | X | | | X | | | X | |
| HBcrAg[m] | X | X | X | | X | | | X | | | X | | | X |
| Exploratory serology[p] | X | X | X | X | X | | | X | | | X | | | X |

TABLE 6-continued

Schedule of Activities - Open-label Study Intervention Phase (Weeks 52-148): Arm 2. After Week 148 (or early discontinuation) visit, participants of Arm 2 enter the follow-up phase.

| | | | | | | | | | | | | | | |
|---|---|---|---|---|---|---|---|---|---|---|---|---|---|---|
| **Pharmacokinetics** | | | | | | | | | | | | | | |
| Blood sampling for sparse PK of RNAi component and optionally NA[q] | X[r] | | X[r] | | X[r] | | | X[r] | | | | | | X[r] |
| Blood sampling for intensive PK of RNAi component and opt. NA (PK subgroup)[s] | X[t] | | | | | | | | | | | | | |
| **Exploratory Biomarkers** | | | | | | | | | | | | | | |
| Whole blood RNA gene expression | X | | | | X | | | X | | | | | | X |
| Whole blood single cell profiling | X | | X | X | X | | | X | | X | | X | | X |
| Host serum proteins (e.g., cytokines) | X | X | X | X | X | | | X | | X | | X | | X |
| Antidrug antibodies (to RNAi component) | X | | | | | | | X | | | | | | X |
| **Immune monitoring** | | | | | | | | | | | | | | |
| Immune cells (PBMCs) selected sites only[u] | X | | | | | | | X | | | | | | X |
| **Pharmacogenomics (DNA)** | | | | | | | | | | | | | | |
| Epigenetics | X | | | | | | | X | | | | | | X |
| **PRO Evaluations[v]** | | | | | | | | | | | | | | |
| HBQOL | X | | | | X | | | X | | | X | | | X |
| SF-36v2 | X | | | | X | | | X | | | X | | | X |
| EQ-5D-5L | X | | | | X | | | X | | | X | | | X |
| **Ongoing participant review** | | | | | | | | | | | | | | |
| Concomitant therapy | X | X | X | X | X | X | X | X | X | X | X | X | X | X |
| Adverse Events | X | X | X | X | X | X | X | X | X | X | X | X | X | X |

| | Study Phase Open-label Visit Day (D)/Week (W) | | | | | | | | | | | |
|---|---|---|---|---|---|---|---|---|---|---|---|---|
| | W104 | W108 | W112 | W116 | W120 | W124 | W128 | W132 | W136 | W140 | W144 | W148/ WD[a] |
| | Study Day (Window) | | | | | | | | | | | |
| | 729 ± 1 w | 757 ± 1 w | 785 ± 1 w | 813 ± 1 w | 841 ± 1 w | 869 ± 1 w | 897 ± 1 w | 925 ± 1 w | 953 ± 1 w | 981 ± 1 w | 1009 ± 1 w | 1037 ± 1 w |
| **Study Intervention Admin.** | | | | | | | | | | | | |
| Administer RNAi component | X | X | X | X | X | X | X | X | X | X | X | |
| Dispense NA | X | X | X | X | X | X | X | X | X | X | X | (X)[c] |
| Intake of NA[b] | X | X | X | X | X | X | X | X | X | X | X | (X) |
| NA accountability | X | X | X | X | X | X | X | X | X | X | X | (X) |
| **Safety Evaluations** | | | | | | | | | | | | |
| Symptom-directed X physical examination[e] | X | X | X | X | X | X | X | X | X | X | X | |
| Liver ultrasound[d] | | | | | | X | | | | | | X |
| Vital signs[f] | X | X | X | X | X | X | X | X | X | X | X | X |
| Triplicate 12-lead ECG[g] | | | X | | | X | | | X | | | X |

TABLE 6-continued

Schedule of Activities - Open-label Study Intervention Phase (Weeks 52-148): Arm 2. After Week 148 (or early discontinuation) visit, participants of Arm 2 enter the follow-up phase.

| | | | | | | | | | | | | |
|---|---|---|---|---|---|---|---|---|---|---|---|---|
| Injection site reactions | X | X | X | X | X | X | X | X | X | X | X | X |
| Clinical Laboratory Tests | | | | | | | | | | | | |
| Hematology | X | X | X | X | X | X | X | X | X | X | X | X |
| Blood chemistiy (including liver function tests)[h,i,j] | | | X | | | X | | | X | | | X |
| Blood coagulation | | | X | | | X | | | X | | | X |
| Urinalysis and urine chem.[k] | | | X | | | X | | | X | | | X |
| Urine pregnancy test (women of childbearing potential) | X | X | X | X | X | X | X | X | X | X | X | X |
| Efficacy Evaluations | | | | | | | | | | | | |
| Fibroscan | | | | | | | | | | | | X[1] |
| HBV and HDV virology | | | | | | | | | | | | |
| Blood sampling for HBV DNA and HDV RNA | X | X | X | X | X | X | X | X | X | X | X | X |
| Blood sampling for HBV RNA[m] | | | X | | | X | | | X | | | X |
| Sampling for viral genome sequencing[n] | | | X | | | X | | | X | | | X |
| HBV serology | | | | | | | | | | | | |
| Blood sampling for: | | | | | | | | | | | | |
| Anti-HBs and anti-HBe | | | | | | X | | | | | | X |
| HBsAg and HBeAg (qualitative) | | | | | | X | | | | | | X |
| HBsAg (quantitative) | X | X | X | X | X | X | X | X | X | X | X | X |
| HBeAg[o] (quant.) | | | X | | | X | | | X | | | X |
| HBcrAg[l] | | | X | | | X | | | X | | | X |
| Exploratory serology[p] | | | X | | | X | | | X | | | X |
| Pharmaco-kinetics | | | | | | | | | | | | |
| Blood sampling for sparse PK of RNAi component and optionally NA[q] | | | | | | | | | | | | |
| Blood sampling for intensive PK of RNAi component and opt. NA (PK subgroup)[s] | | | | | | | | | | | | |
| Exploratory Biomarkers | | | | | | | | | | | | |
| Whole blood RNA gene expression | | | | | | | | | | | | X |
| Whole blood single cell profiling | | | | | | | | | | | | X |
| Host serum proteins (e.g., cytokines) | | | | | | | | | | | | X |
| Antidrug antibodies (to RNAi component) | | | | | | X | | | | | | X |
| Immune monitoring | | | | | | | | | | | | |
| Immune cells (PBMCs) selected sites only[u] | | | | | | | | | | | | X |
| Pharmacogenomics (DNA) | | | | | | | | | | | | |
| Epigenetics | | | | | | | | | | | | X |
| PRO Evaluations[v] | | | | | | | | | | | | |
| HBQOL | | | X | | | X | | | X | | | X |
| SF-36v2 | | | X | | | X | | | X | | | X |
| EQ-5D-5L | | | X | | | X | | | X | | | X |

TABLE 6-continued

| Schedule of Activities - Open-label Study Intervention Phase (Weeks 52-148): Arm 2. After Week 148 (or early discontinuation) visit, participants of Arm 2 enter the follow-up phase. | | | | | | | | | | | | |
|---|---|---|---|---|---|---|---|---|---|---|---|---|
| Ongoing participant review | | | | | | | | | | | | |
| Concomitant therapy | X | X | X | X | X | X | X | X | X | X | X | X |
| Adverse Events | X | X | X | X | X | X | X | X | X | X | X | X |

General Note: The PRO assessments are preferably completed before any tests, procedures or other consultations for that visit to prevent influencing the participant's perceptions. AFP: alpha-fetoprotein; ALP: alkaline phosphatase; ALT: alanine aminotransferase; AST: aspartate aminotransferase; CKD-EPI: Chronic Kidney Disease Epidemiology Collaboration; CRF: case report form; CT: computed tomography; D/d: Day/days; DBP: diastolic blood pressure; DNA: deoxyribonucleic acid; ECG: electrocardiogram; eGFR: estimated glomerular filtration rate; FSH: follicle-stimulating hormone; HBc: hepatitis B core protein; HBe(Ag): hepatitis B e (antigen); HBcrAg: hepatitis B core-related antigen; HBQOL: Hepatitis B Quality of Life; HBs(Ag): hepatitis B surface (antigen); HBV: hepatitis B virus; HCC hepatocellular carcinoma; HDV: hepatitis D virus; HIV-1 (-2): human immunodeficiency virus type 1 (type 2); ICF: informed consent form; IgM: immunoglobulin M; IWRS: interactive web response system; MRI: magnetic resonance imaging; NA: nucleos(t)ide analog; PBMC: peripheral blood mononuclear cells; PGIC: patient global impression of change; PK: pharmacokinetic; PRO: patient-reported outcome; RNA: ribonucleic acid; SBP: systolic blood pressure; ULN: upper limit of normal; W: Week; WD: withdrawal.

a. Participants who discontinue RNAi component early have an early WD visit and enter follow-up unless they withdraw consent/assent. Participants who withdraw consent/assent are offered an optional safety follow-up visit.
b. In between study visits, participants take NA at home and they bring their NA with them to each study visit.
c. NA continues to be dispensed at and after Week 148 for participants without cirrhosis at the investigator's discretion and for participants with cirrhosis.
d. A liver ultrasound is performed every 24 weeks from Day 1 for HCC screening in all participants.
e. Symptom-directed physical examination, including body weight.
f. Vital signs include supine SBP, DBP, pulse rate, and body temperature.
g. All ECGs are read centrally. On Day 1, pre-dose ECG assessment is also done locally on site to determine eligibility.
h. Biochemistry samples are taken after fasting for at least 10 hours for measurement of phosphate, calcium, creatinine, and lipids.
i. Creatinine clearance (eGFR calculated by the CKD-EPI formula) is assessed.
j. Intervention-emergent ALT/AST elevations (i.e., ALT and/or AST≥3×ULN and ≥3× nadir [i.e., lowest value during study participation]), triggers an assessment of confounding factors (alcohol intake, change in concomitant medication, and comorbidities). Participants are required to come for weekly visits until ALT and/or AST levels have returned to 50% of the maximal value and, if present, liver-related symptoms have improved. At a minimum, the following blood chemistry parameters are assessed in the central laboratory at these weekly visits: ALT, AST, ALP, bilirubin (total and direct), albumin, coagulation, and HBV DNA.
k. Urine chemistry sample (quantitative measurement): creatinine, sodium, phosphate, glucose, protein, and albumin. Urinalysis by dipstick: specific gravity, pH, glucose, protein, blood, ketones, bilirubin, urobilinogen, nitrite, leukocyte esterase, and microscopic analysis if needed. In case of a positive dipstick result, a urine sample is set aside for additional examination of the positive parameter at the central laboratory (e.g., quantification as applicable).
l. Only applicable to participants who are enrolled at a site with an on-site Fibroscan device.
m. HBcrAg and HBV RNA samples may be batched and only selected samples may be tested at the sponsor's discretion. Samples can be used for assessment of other serologic/virologic markers of HBV and HDV.
n. Samples may be sequenced based on the sponsor virologist's request.
o. Quantitative HBeAg assessment is only performed in participants who are defined HBeAg-positive at screening based on a qualitative HBeAg assay.
p. Exploratory serology samples may be analyzed at the sponsor's discretion. Samples may be used to assess virologic or serologic markers of HBV.
q. All participants have sparse PK sampling. For all samples, the time of the preceding 2 intakes of NA and the time of PK sampling is recorded.
r. One sample at any time between 2 and 8 hours after RNAi component dosing with collection of the time interval between last administration and blood draw. Before leaving the study site, the participant's wellbeing is confirmed.
s. All participants who consent to participate in the intensive PK subgroup (optional) undergo intensive PK sampling at Week 52. If necessary (e.g., for operational reasons), this visit may be scheduled at Week 56, 60, or 64. The study intervention is taken on site and time of dosing is recorded. Pharmacokinetic samples are taken predose and 15 minutes, 30 minutes, 1, 2, 3, 4, 6, 8,* 10,* and 24 hours postdose (*the 8 and 10 hours postdose samples are optional). All efforts are made to obtain the PK samples at the exact nominal time relative to dosing. However, samples obtained within 20% of the nominal time from dosing (e.g., within 12 minutes of a 60-minute time point) are not captured as a protocol deviation if the exact time of the sample collection is noted on the source document and CRF.
t. Sparse PK sampling is not required if the participant is part of the intensive PK subgroup and has an intensive PK sampling at the same visit.
u. PBMC samples are collected at selected sites only. Additional PBMC samples may be taken in case of ALT flares, upon discussion with the sponsor, which may require an unscheduled visit.
v. PRO assessments are performed by participants at sites where appropriate translations are available.

TABLE 7

Schedule of Activities-Follow-up Phase. After completion of the study intervention phase (or early discontinuation), all participants enter the 48-week follow-up phase (unless they withdraw consent).

| | Study Phase Follow-up[a,b] Follow-up (FU) Week (W) | | | | | | | | | | | |
|---|---|---|---|---|---|---|---|---|---|---|---|---|
| | FU W2 | FU W4 | FU W6 | FU W8 | FU W12 | FU W16 | FU W20 | FU W24 | FU W30 | FU W36 | FU W42 | FU W48 EOS |
| | FU Study Day (Window) | | | | | | | | | | | |
| **Study Intervention Admin.** | | | | | | | | | | | | |
| Administer/Dispense NA[c] | (X) | (X) | (X) | (X) | (X) | (X) | (X) | (X) | (X) | (X) | (X) | (X) |
| NA accountability[d] | (X) | (X) | (X) | (X) | (X) | (X) | (X) | (X) | (X) | (X) | (X) | (X) |
| **Safety Evaluations** | | | | | | | | | | | | |
| Symptom-directed physical examination[e] | X | X | X | X | X | X | X | X | X | X | X | X |
| Liver ultrasound[f] | | | | | | | | X | | | | X |
| Vital signs[g] | X | X | | X | | X | | X | X | | X | X |
| Triplicate 12-lead ECG[h] | | X | | | | | | | | | | |
| **Clinical Laboratory Tests** | | | | | | | | | | | | |
| Hematology | X | X | | X | | X | | X | | X | | X |
| Blood chemistry (including liver function tests)[i,j,k] | X | X | X[l] | X[l] | X | X[l] | X[l] | X | X[l] | X | X | X |
| Blood coagulation | X | X | | X | | X | | X | | X | | X |
| Urinalysis and urine chem.[m] | | X | | | | | | | | | | |
| Urine pregnancy test (women of childbearing potential) | | X | | X | X | X | X | X[n] | X[n] | X[n] | X[n] | X |
| **Efficacy Evaluations** | | | | | | | | | | | | |
| Fibroscan[o] | | | | | | | | X | | | | X |
| **HBV and HDV virology** | | | | | | | | | | | | |
| Blood sampling for HBV DNA and HDV RNA | X | X | X | X | X | X | X | X | X | X | X | X |
| Blood sampling for HBV RNA[p] | | | | | X | | | X | | X | | |
| Sampling for viral genome sequencing[q] | | X | | | X | | X | | X | | X | |
| **HBV serology Blood sampling for:** | | | | | | | | | | | | |
| Anti-HBs and anti-HBe | | | | | X | | | X | | X | | X |
| HBsAg and HBeAg (qual.) | | | | | | | | X | | | | X |
| HBsAg and HBeAg (quant.) | X | X | X | X | X | X | X | X | X | X | X | X |
| HBcrAg[p] | | X | | | X | | | X | | X | | X |
| Exploratory serology[r] | X | X | | X | X | X | | X | | X | | X |
| **Exploratory Biomarkers** | | | | | | | | | | | | |
| Whole blood RNA gene expression | | X | | | | | | X | | | | X |
| Whole blood single cell profiling | | X | | X | X | X | | X | | X | | X |
| Host serum proteins (e.g., cytokines) | | X | | X | X | X | | X | | X | X | |
| Antidrug antibodies (to RNAi component) | | | | | | | | X | | | | X |
| **Immune monitoring** | | | | | | | | | | | | |
| Immune cells (PBMCs) selected sites only[s] | | | | | X | | | X | | | | X |

TABLE 7-continued

Schedule of Activities-Follow-up Phase. After completion of the study intervention phase (or early discontinuation), all participants enter the 48-week follow-up phase (unless they withdraw consent).

| | Study Phase Follow-up[a,b] Follow-up (FU) Week (W) | | | | | | | | | | | |
|---|---|---|---|---|---|---|---|---|---|---|---|---|
| | FU W2 | FU W4 | FU W6 | FU W8 | FU W12 | FU W16 | FU W20 | FU W24 | FU W30 | FU W36 | FU W42 | FU W48 EOS |
| | FU Study Day (Window) | | | | | | | | | | | |
| PRO Evaluations[t] | | | | | | | | | | | | |
| HBQOL | | | | | X | | | X | | X | | X |
| SF-36v2 | | | | | X | | | X | | X | | X |
| EQ-5D-5L | | | | | X | | | X | | X | | X |
| Ongoing participant review | | | | | | | | | | | | |
| Concomitant therapy | X | X | X | X | X | X | X | X | X | X | X | X |
| Adverse Events | X | X | X | X | X | X | X | X | X | X | X | X |

General Note: The PRO assessments should preferably be completed before any tests, procedures or other consultations for that visit to prevent influencing the participant's perceptions.

ALP: alkaline phosphatase; ALT: alanine aminotransferase; AST: aspartate aminotransferase; CKD-EPI: Chronic Kidney Disease Epidemiology Collaboration; D/d: Day/days; DBP: diastolic blood pressure; DNA: deoxyribonucleic acid; ECG: electrocardiogram; eGFR: estimated glomerular filtration rate; EOS: end of study; Ext FU: extended follow-up; FU: follow-up; HBcrAg: hepatitis B core-related antigen; HBe(Ag): hepatitis Be (antigen); HBQOL: Hepatitis B Quality of Life; HBs(Ag): hepatitis B surface (antigen); HBV: hepatitis B virus; HDV: hepatitis D virus; NA: nucleos(t)ide analog; PBMC: peripheral blood mononuclear cells; PGIC: patient global impression of change; PRO: patient-reported outcome; RNA: ribonucleic acid; SBP: systolic blood pressure; ULN: upper limit of normal; W: Week.

a. All follow-up study visits are scheduled relative to the last dose of RNAi component. An unscheduled visit can be performed upon the investigator's discretion, in case of HBV DNA elevations, ALT elevations, other signs of worsening of liver disease, or for any other reason during follow-up.
b. Participants who withdraw consent/assent during follow-up are offered an optional safety follow-up visit.
c. No RNAi component is administered or dispensed during follow-up. Administration/Dispensation of NA is only applicable for participants who continue NA treatment at the investigator's discretion and participants with cirrhosis.
d. For participants who take NA during follow-up.
e. Symptom-directed physical examination, including body weight.
f. A liver ultrasound is performed every 24 weeks from start of FU for HCC screening in all participants.
g. Vital signs include supine SBP, DBP, pulse rate, and body temperature.
h. All ECGs will be read centrally.
i. Biochemistry samples must be taken after fasting for at least 10 hours for measurement of phosphate, calcium, creatinine, and lipids.
j. Creatinine clearance (eGFR calculated by the CKD-EPI formula) will be assessed.
k. ALT/AST elevations (i.e., ALT and/or AST≥3×ULN and ≥3× nadir [i.e., lowest value during study participation]), trigger an assessment of confounding factors (alcohol intake, change in concomitant medication, and comorbidities). Participants are also required to come for weekly visits until ALT and/or AST levels have returned to 50% of the maximal value and, if present, liver-related symptoms have improved. At a minimum, the following blood chemistry parameters are assessed in the central laboratory at these weekly visits: ALT, AST, ALP, bilirubin (total and direct), albumin, coagulation, and HBV DNA.
l. Liver function tests only.
m. Urine chemistry sample (quantitative measurement): creatinine, sodium, phosphate, glucose, protein, and albumin. Urinalysis by dipstick: specific gravity, pH, glucose, protein, blood, ketones, bilirubin, urobilinogen, nitrite, leukocyte esterase, and microscopic analysis if needed. In case of a positive dipstick result, a urine sample is set aside for additional examination of the positive parameter at the central laboratory (e.g., quantification as applicable).
n. Urine pregnancy tests for at-home use are provided to the participants from Follow-up Week 24 onwards. Results are reported at the next visit.
o. Only applicable to participants who are enrolled at a site with an on-site Fibroscan device.
p. HBcrAg and HBV RNA samples may be batched and only selected samples may be tested at the sponsor's discretion. Samples can be used for assessment of other serologic/virologic markers of HBV.
q. Samples may be sequenced based on the sponsor virologist's request.
r. Exploratory serology samples may be analyzed at the sponsor's discretion. Samples may be used to assess virologic or serologic markers of HBV.
s. PBMC samples may be collected at selected sites only. Additional PBMC samples may be taken in case of ALT flares, upon discussion with the sponsor, which may require an unscheduled visit.
t. PRO assessments are performed by participants at sites where appropriate translations are available.

We claim:

1. A method of treating a Hepatitis D Virus infection in a human subject in need thereof, comprising administering a pharmaceutical composition comprising an RNAi component, wherein the RNAi component comprises:

(i) a first RNAi agent comprising: an antisense strand comprising a modified nucleotide sequence of asGfsasAfaAfuUfgAfgAfgAfaGfuCfcasc (SEQ ID NO:2) and a sense strand comprising a modified nucleotide sequence of (NAG37)s-(invAb)sguggacuuCfUfCfucaauuuucus(invAb) (SEQ ID NO:11); and (ii) a second RNAi agent comprising: an antisense strand comprising a modified nucleotide sequence of usAfscsCfaAfuUfuAfuGfcCfuAfcAfgcsg (SEQ ID NO:8) and a sense strand comprising a modified nucleotide sequence of (NAG37)s-(invAb)scgcuguagGfCfAfuaaauugguas(invAb) (SEQ ID NO:16), wherein (NAG37) s has the structure:

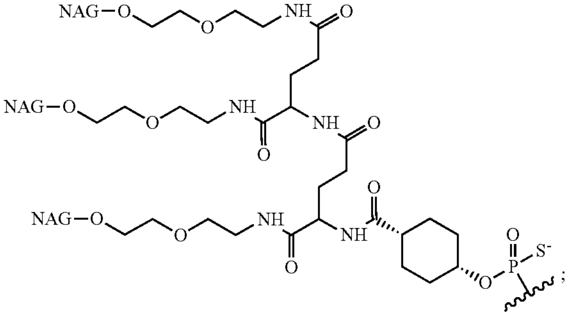

wherein (invAb) is an inverted (3'-3' linked) abasic deoxyribonucleotide;

wherein (invAb) s is an inverted abasic deoxyribonucleotide-5'-phosphorothioate;

wherein a, g, c and u are 2'-O-methyl modified nucleotides;

wherein Af, Cf, Gf, and Uf are 2'-fluoro modified nucleotides;

wherein s is a phosphorothioate linkage; and wherein the RNAi component is administered to the human subject via intravenous or subcutaneous injection and in a dose of 40-200 mg once monthly or once every four weeks.

2. The method of claim 1, wherein the treatment further comprises administering an effective amount of a nucleoside analog or a nucleotide analog.

3. The method of claim 1, wherein the human subject further comprises cirrhosis.

4. The method of claim 1, wherein the human subject is a patient without cirrhosis.

5. The method of claim 2, wherein the administration of the nucleoside analog or nucleotide analog is continued after stopping the administration of the effective amount of the RNAi component.

6. The method of claim 1, wherein the pharmaceutical composition further comprises a pharmaceutically acceptable carrier, diluent, excipient, or a combination of any of the foregoing.

7. The method of claim 1, wherein the first and second RNAi agents in the RNAi component are administered in a ratio of about 2:1.

8. The method of claim 1, wherein the RNAi component is administered at about 50 mg per dose.

9. The method of claim 1, wherein the RNAi component is administered at about 200 mg per dose.

10. The method of claim 6, wherein the pharmaceutical composition is a sterile aqueous solution.

11. The method of claim 6, wherein the pharmaceutical composition is a sterile powder for the extemporaneous preparation of a sterile injectable solution or dispersion.

* * * * *